(12) United States Patent
Catcheside

(10) Patent No.: US 6,232,112 B1
(45) Date of Patent: May 15, 2001

(54) REAGENTS AND METHODS FOR DIVERSIFICATION OF DNA

(75) Inventor: David E. Catcheside, Bellevue Heights (AU)

(73) Assignee: Flinders Technologies Pty Ltd of Flinders University (AU)

( * ) Notice: Subject to any disclaimer, the term of this patent is extended or adjusted under 35 U.S.C. 154(b) by 0 days.

(21) Appl. No.: 08/977,171

(22) Filed: Nov. 24, 1997

(51) Int. Cl.$^7$ .................................................. C12N 1/14

(52) U.S. Cl. ............................................... 435/254.4
(58) Field of Search ....................... 435/6, 7.31, 254.4, 435/254.1, 255.2

(56) References Cited

PUBLICATIONS

Kowalczykowski et al., Microbiological Reviews, 58(3):401–65, Sep. 1994.*

Smyth, D.R., "Genetic Control of Recombination in the Amination–1 Region of Neurospora Crassa," Thesis submitted for the degree of Doctor of Philosophy in the Australian National University, Canberra, Australia, 257 pages (Apr. 1970).

Alani, E. et al., "Interaction Between Mismatch Repair and Genetic Recombination in Saccharomyces cerevisiae," Genetics, 137:19–39 (May 1994).

Borts, R. et al., "Meiotic Recombination in Yeast: Alteration by Multiple Heterozygosities," Science, 237(4821):1459–1465 (Sep. 18, 1997).

Borts, R. et al., "Length and Distribution of Meiotic Gene Conversion Tracts and Crossovers in Saccharomyces cerevisiae," Genetics, 123:69–80 (Sep.–Dec., 1989).

Bowring, F. et al., "The orientation of gene maps by recombination of flanking markers for the am locus of Neurospora crassa," Current Genetics, 29(1):27–33 (1995).

Detloff, P. et al., "Analysis of a Gene Conversion Gradient at the HIS4 Locus in Saccharomyces cerevisiae," Genetics, 132:113–123 (Sep.–Dec., 1992).

Fogel, S. et al., "Meiotic Gene Conversion: A Signal of the Basic Recombination Event in Yeast," Cold Spring Harbor Symposia on Quantitative Biology, vol. XLIII, DNA: Replication and Recombination, pp. 1325–1341 (1979).

Foss, E. et al., "Chiasma Interference as a Function of Genetic Distance," Genetics, 133:681–691 (Jan.–Apr., 1993).

Gilbertson, L. et al., "A Test of the Double–Strand Break Repair Model for Meiotic Recombination in Saccharomyces cerevisiae," Genetics, 144(1):27–41 (Sep., 1996).

Grimm, C. et al., "M26 Recombinational Hotspot and Physical Conversion Tract Analysis in the ade6 Gene of Schizosaccharomyces pombe," Genetics, 136:41–51 (Jan.–Apr., 1994).

Hurst, D. et al., "Conversion–Associated Recombination in Yeast," Proc. Nat. Acad. Sci. USA, 69(1):101–105 (Jan., 1972).

Judd, S. et al., "Physical Lengths of Meiotic and Mitotic Gene Conversion Tracts in Saccharomyces cerevisiae," Genetics, 118:401–410 (Jan.–Apr., 1988).

Kinnaird, J. et al., The complete nucleotide sequence of the Neurospora crassa am (NADP–specific glutamate dehydrogenase) gene, Gene, 24:253—260 (1983).

(List continued on next page.)

Primary Examiner—Scott W. Houtteman
(74) Attorney, Agent, or Firm—Merchant & Gould P.C.

(57) ABSTRACT

The present invention provides methods and compositions for diversification of heterologous DNA sequences in vivo. The present invention employs a recombination hotspot functionally coupled to the heterologous DNA. The process of recombination generates new versions of the foreign sequences by recombining their differences in new combinations. Errors in recombination generate additional sequence diversity.

69 Claims, 23 Drawing Sheets

Map of the *his–3, cog, lpl* region of Linkage Group I of *Neurospora crassa* Vertical bars, triangles and hairpins show the location of sequence differences that distinguish the St Lawrence and Lindegren wild type strains. The corresponding full DNA sequences are given in Fig. 7 and Fig. 8. Vertical slashes indicate one to seven base substitutions per 10 base pairs. Triangles indicate short sequence insertions and the hairpin a 101 base pair inverted repeat transposon fragment present in St Lawrence.

OTHER PUBLICATIONS

Malone, R. et al., "Analysis of a Recombination Hotspot for Gene Conversion Occurring at the HIS2 Gene of *Saccharomyces cerevisiae*," *Genetics*, 137(1):5–18 (May, 1994).

Modrich, P., "Mechanisms and Biological Effects of Mismatch Repair," *Annual Reviews of Genetics*, 25:229–253 (1991).

Nicolas, A. et al., "An initiation site for meiotic gene conversion in the yeast *Saccharomyces cerevisiae*," *Nature*, 338(6210):35–39 (Mar. 2, 1989).

Orr–Weaver, T. et al., "Fungal Recombination," *Microbiological Reviews*, 49(1):33–58 (Mar., 1985).

Perkins, D., "Estimates of the Proportion of Recombination Intermediates That Are Resolved With Crossing Over in *Neurospora crassa*," *Genetics*, 133:690–691 (Jan.–Apr., 1993).

Porter, S. et al., "Genetics Evidence That the Meiotic Recombination Hotspot at the HIS4 Locus of *Saccharomyces cerevisiae* Does Not Represent a Site for a Symmetrically Processed Double–Strand Break," *Genetics*, 134:5–19 (May–Aug., 1993).

Reenan, R. et al., "Characterization of Insertion Mutations in the *Saccharomyces cerevisiae* MSH1 and MSH2 Genes: Evidence for Separate Mitochondrial and Nuclear Functions," *Genetics*, 132:975–985 (Sep.–Dec., 1992).

Schultes, N. et al., "Decreasing Gradients of Gene Conversion on Both Sides of the Initiation Site for Meiotic Recombination at the ARG4 Locus in Yeast," *Genetics*, 126:813–822 (Sep.–Dec., 1990).

Smyth, D., "A New Map of the amination–I Locus of Neurospora Crassa, and the Effect of the recombination–3 Gene," *Aust. J. Biol. Sci.*, 26:1355–1370 (1973).

Stadler, D., "The Mechanism of Intragenic Recombination," *Annual Review of Genetics*, 7:113–127 (1973).

* cited by examiner

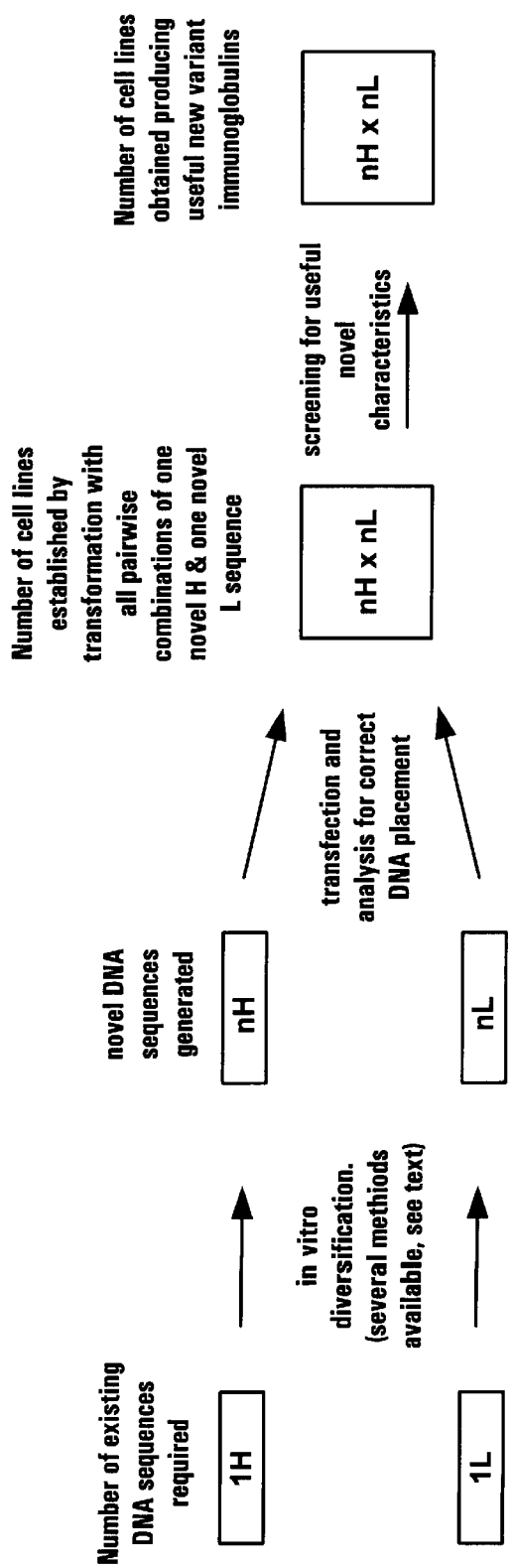

FIG. 2A

Methods for the diversification of DNA sequences coding subunits of heteropolymeric proteins and testing for superior variants.

The example given for immunoglobulins is for illustrative purposes only and is not intended to limit application of the present invention to this specific heteromeric protein. H = heavy chain genes, L = light chain genes Existing protocol: *Number of transfections needed to generate 1024 new combinations: 2048*

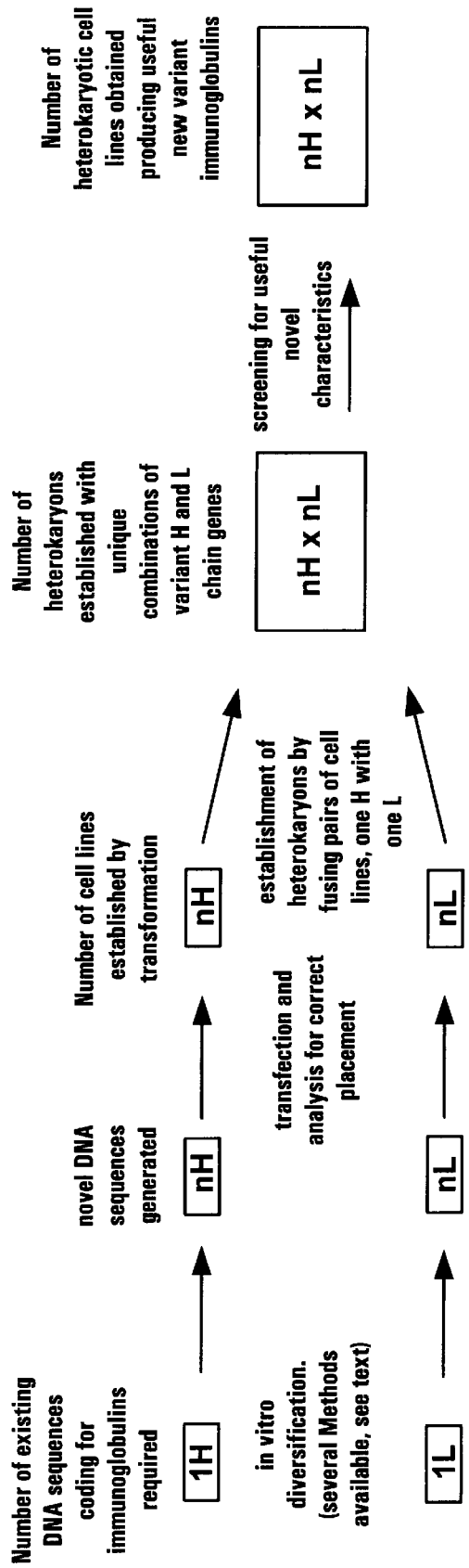

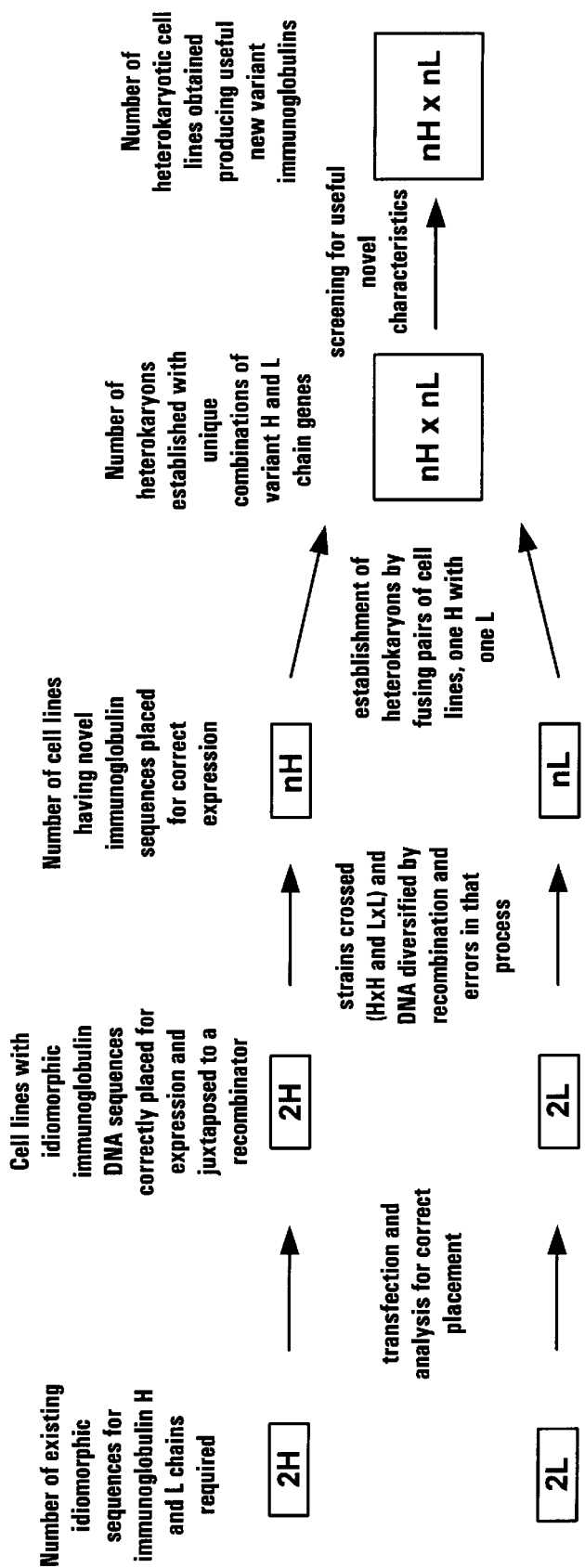
FIG. 2C  A protocol enabled by the present invention
Number of transfections needed to generate 1024 new combinations: 4

Fig. 3

The modified double strand break repair model for meiotic recombination. After H Sun *et al* Cell 64: 1155-1161, 1991

(a) A double strand break (DSB) is made in one DNA duplex. (b) A long 3' overhanging single strand tail is generated either side of the break by resection. (c) One 3' end invades a homologous duplex forming a D loop. (d) the D loop is enlarged by repair synthesis and anneals to the second 3' end (e) Repair synthesis occurs at the second 3' end and two intermolecular junctions (Holliday junctions) are formed. Resolution of the junctions by cutting inner and outer strands can give rise to non-crossover (f) and crossover (g) chromosomes. If there are base mismatches in the heteroduplex regions (duplex molecules with thick and thin lines) there will be gene conversion. If mismatch repair does not occur there will be post meiotic segregation of new sequence combinations.

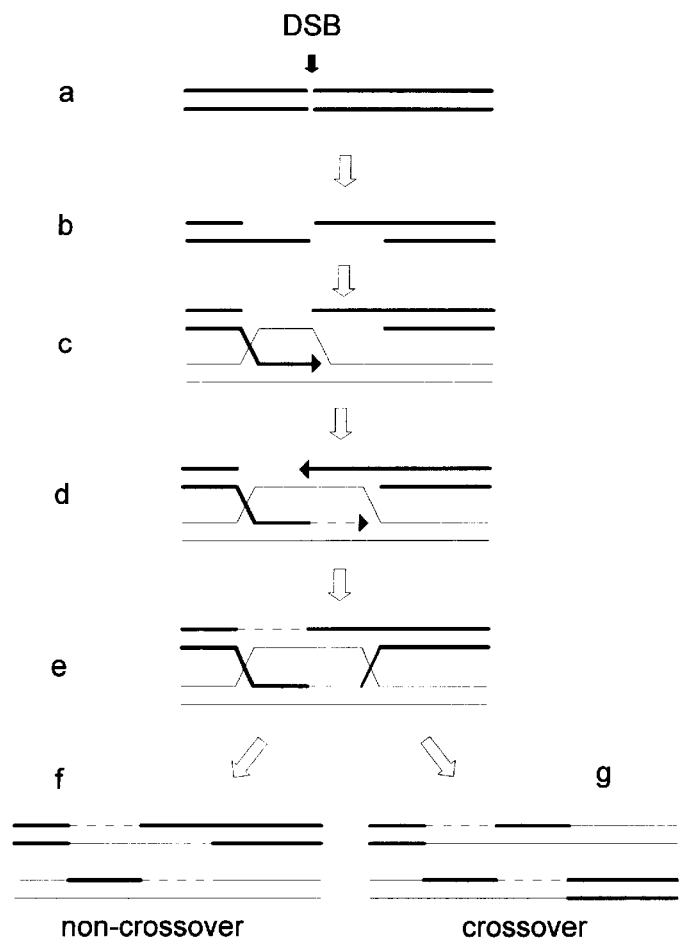

Life cycle of *Neurospora crassa* after JRS Fincham (Genetics, Wright 1983). Microconidia having one nucleus are not shown but can be generated as described in the text. Perithecia and protoperithecia are shown in section.

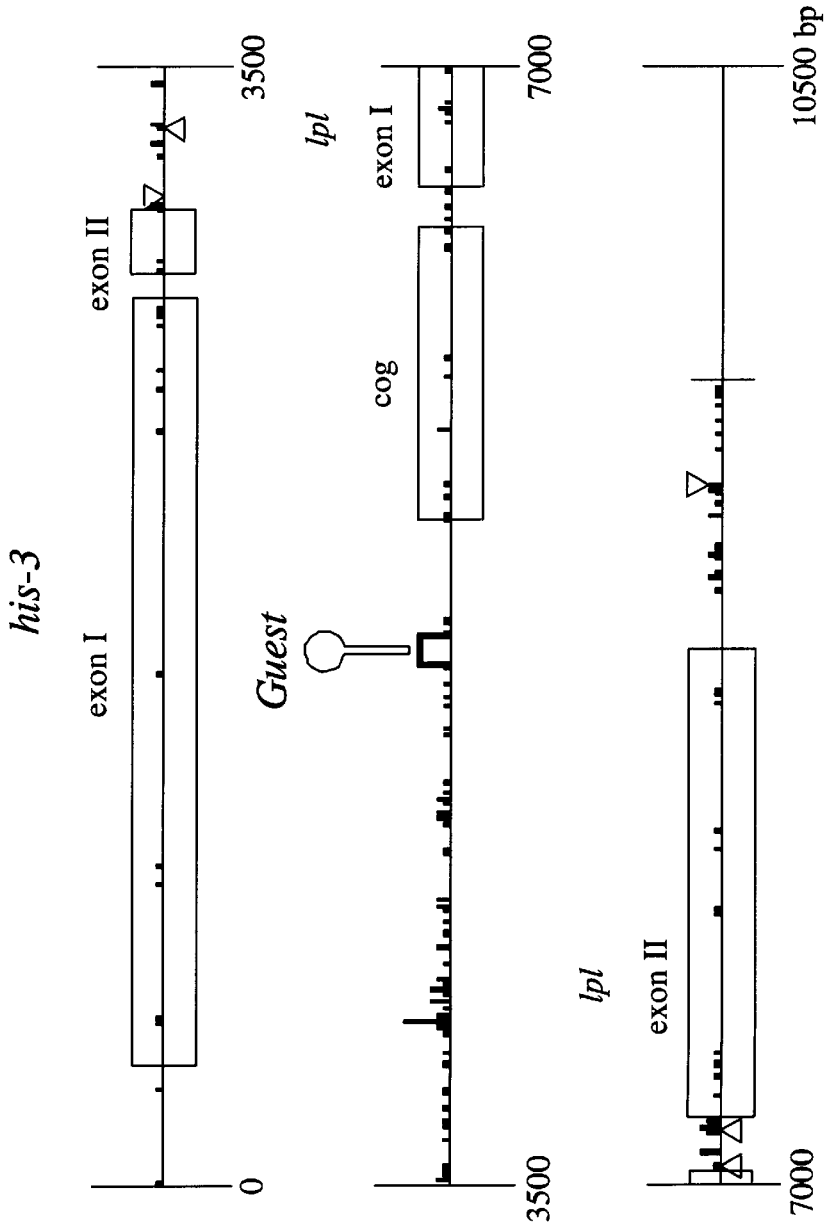

FIG. 5 Map of the *his-3, cog, lpl* region of Linkage Group I of *Neurospora crassa* Vertical bars, triangles and hairpins show the location of sequence differences that distinguish the St Lawrence and Lindegren wild type strains. The corresponding full DNA sequences are given in Fig. 7 and Fig. 8. Vertical slashes indicate one to seven base substitutions per 10 base pairs. Triangles indicate short sequence insertions and the hairpin a 101 base pair inverted repeat transposon fragment present in St Lawrence.

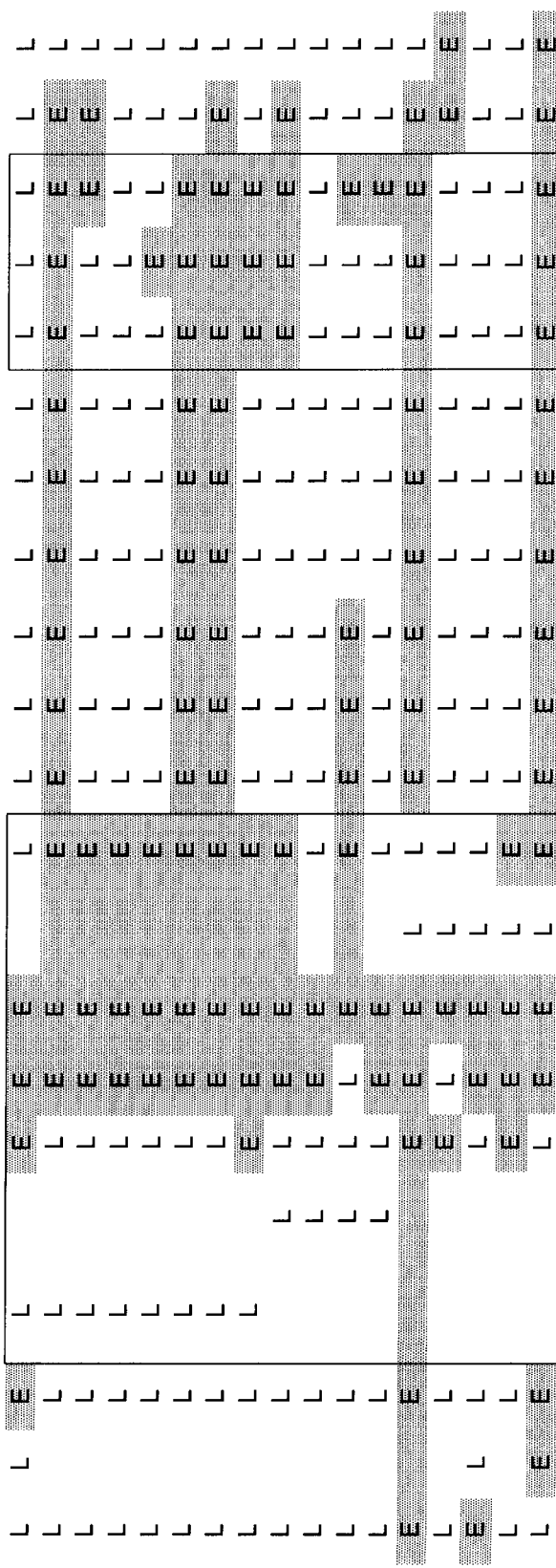

FIG. 6  Discontinuity in the parental origin of DNA sequences in progeny from crosses between pairs of *his-3* alleles. In most cases this reflects discontinuity of conversion tracts, in some cases crossovers near the ends of conversion tracts. Markers are specific DNA sequence differences that distinguish the parents. These were all E (Emerson wild type origin) or all L (Lindegren wild type origin) in the parental strains. Recombinants carry both E and L markers. Marker position is given in base pairs from the first base of the first codon of the *his-3* gene. Each line of the table shows the parental origin of the markers inherited by one of the progeny.

FIG. 7

Nucleotide sequence of the *his-3 cog$^L$ lpl* region of linkage group I in the Lindegren wild type strain of *Neurospora crassa*. This differs from that in the StLawrence strain in many positions, summarised in figure 5. The coordinates of relevant features are given in the text. This sequence contains the high frequency recombinator *cog$^L$* which is active providing the cross in which meiosis occurs is homozygous*rec-2*.

```
   1 GATCGCAACT GGAGATCACT CGCACCGTGC CGCAGAACAA GGGCGACGAG CCTCAGGGCA
  61 GTTTAGCCTG CCGTAACAGC ACAGACCATA GCTTATTTTC ACCTGGGCGG GCGGGCGACG
 121 GCGGCACTGA CATCGGCAAG GCGGCATCAA GCAACCCCTC TGTTGCTTGC CAGCTGCCGG
 181 CCAACGTCAG CGGTACAAGG AGAAATCTGG AAGGAAAGAC TTCTGGCACC GACAGGATGG
 241 CACGCGGGAA AAGTTCCCAA TGCATGAGAT GAGGGGCATT TGCATTGCCT CCCGTCACAC
 301 TGCCCGCGAA CCCCAACCCC ACCATAGCGT CTGTCGATAC ATGGAGCGCG AAGTCGAGAA
 361 ACCTGTAATT CCTGGTAACT TTCAGGTACA CAGTACGTAC TGATCCTGGT ATCAAACCTT
 421 GCCTGCCGAG TTTTCGACGG AAAGAGGTGT GAATTGTGAA AGAGTCATAC CAAATCACCC
 481 GATTTTCATA AAGCCCGAGT CTTTTCTGTA CATAAGCGAC ACTCGAAGCG GCCTCATCT
 541 TCATAGCCTG ATAGCTTGTA ATACTCCATC CTCGTATCTC ACTTGACCTT GAGTTCAACC
 601 CCACGTCAGA CTTCACCCGA CACATCGACG GATTGGGGAA CAGCACAATA CCTGAAAAGC
 661 GAGAAAACCA AACAGAGGAA AACACCATGG AGACAACACT TCCCCTCCCC TTCCTCGTCG
 721 GTGTCAGTGT TCCTCCCGGA CTGAATGACA TCAAGGAGGG CCTCAGCCGG GAGGAAGTCT
 781 CGTGTCTTGG CTGCGTCTTC TTCGAGGTCA AGCCCAAGAC CCTTGAGAAA ATCGTGCGAT
 841 TCCTCAAGCG TCACAATGTC GAATTTGAGC CCTACTTCGA TGTAACAGCC CTCGAGTCTA
 901 TCGATGATAT TATCACTCTT CTGGACGCCG GCGCCCGCAA GGTGTTTGTC AAGACCGAGC
 961 AGTTGGCCGA CCTCTCCGCA TATGGCTCCC GCGTTGCCCC CATTGTCACT GGAAGCAGCG
1021 CTGCTTTGCT TTCCTCCGCC ACCGAGAGCG GCCTTTTGCT CTCCGGCTTC GATCAGACTG
1081 CCTCCGAGGC TGCACAGTTT CTGGAGGAGG CCAGAGACAA GAAAATTACC CCCTTCTTCA
1141 TCAAGCCCGT TCCTGGGGCC GATCTCGAAC AGTTCATCCA GGTCGCCGCC AAGGCTAACG
1201 CCATCCCCAT CCTGCCATCC ACTGGCTTGA CAACAAAGAA GGACGAGGCC GGAAAGCTTG
1261 CCATCTCCAC CATCCTCTCG AGCGTCTGGA AGTCTGACCG TCCCGATGGT CTGCTCCCCA
1321 CCGTTGTCGT TGATGAGCAC GACACTGCTC TGGGTCTGGT CTACAGCAGT GCCGAGAGTG
1381 TGAACGAGGC CCTCAGGACA CAGACTGGTG TCTATCAGAG CCGGAAGCGC GGTCTCTGGT
1441 ACAAGGGTGC TACTTCCGGA GACACTCAGG AGCTCGTCCG CATCTCGCTT GACTGCGATA
1501 ACGATGCTCT CAAGTTTGTC GTGAAGCAGA AGGGTCGTTT CTGCCACCTC GATCAGTCCG
1561 GCTGCTTTGG TCAGCTCAAA GGCCTTCCCA AGCTCGAGCA GACTTTGATT TCGAGGAAAC
1621 AGTCTGCCCC CGAGGGCTCC TACACTGCCC GTCTCTTCTC CGATGAGAAG CTAGTCCGGG
1681 CCAAGATCAT GGAGGAGGCT GAGGAGCTCT GCACCGCTCA GACCCCCCAG GAAATCGCCT
1741 TTGAGGCTGC CGATCTCTTC TACTTTGCTC TTACCAGGGC CGTTGCTGCC GGCGTTACTC
1801 TTGCCGATAT CGAAAGGAGC CTTGACGCCA AGAGCTGGAA GGTCAAGCGC AGGACTGGAG
1861 ATGCTAAGGG TAAGTGGGCT GAGAAGGAGG GCATCAAGCC TGCGGCGTCC GCTCCCGCTG
1921 CCACTTCGGC CCTGTCACC AAGGAGGCCG CCCAGGAGAC CACCCCTGAG AAGATCACCA
1981 TGAGACGTTT CGACGCCTCC AAGGTCTCTA CCGAGGAGCT CGATGCTGCT CTCAAGCGTC
2041 CTGCGCAAAA GTCGTCCGAT GCCATCTACA AGATCATTGT CCCCATCATC GAGGACGTCC
2101 GCAAGAACGG CGACAAGGCT GTTCTGTCGT ACACTCACAA GTTCGAGAAG GCTACCTCTC
2161 TTACTAGCCC CGTCCTGAAG GCGCCCTTCC CCAAGGAGCT TATGCAGCTC CCTGAGGAGA
2221 CCATTGCTGC CATCGACGTG TCCTTCGAGA ACATCCGCAA GTTCCACGCC GCCCAGAAGG
2281 AGGAGAAGCC CCTCCAGGTC GAGACCATGC CCGGTGTTGT CTGCAGCCGT TTCTCTCGTC
2341 CCATCGAGGC CGTCGGCTGC TACATCCCCG GCGGTACCGC CGTTCTCCCC AGCACTGCCC
2401 TTATGCTGGG TGTTCCCGCC ATGGTCGCCG GCTGCAACAA GATTGTGTTC GCCTCTCCTC
2461 CCCGCGCCGA CGGAACCATC ACTCCCGAGA TTGTCCACGT CGCTCACAAG GTTGGGGCCG
2521 AGTCCATCGT GCTTGCCGGC GGTGCCCAGG CCGTAGCTGC CATGGCCTAC GGCACCGAGA
2581 GCATCACCAA GGTCGACAAG ATTCTCGGCC CCGGTAACCA GTTCGTCACT GCTGCCAAGA
2641 TGTTCGTCAG CAACGACACC AACGCTGCCG TTGGGATTGA CATGCCCGCT GGCCCGTCCG
2701 AGGTGCTGGT CATCGCTGAC AAGGACGCCA ACCCCGCGTT CGTTGCCTCG GATCTCCTGT
2761 CCCAGGCTGA GCACGGCGTT GACAGTCAGG TCATCCTGAT CGCTATTAAC CTCGACGAGG
```

FIG. 7 continued

```
2821 AGCATCTTCA GGCTATTGAG GACGAGGTTC ACCGTCAGGC TATGGAGCTT CCTCGCGTCC
2881 AGATTGTCCG TGGCTCCATC GCCCACTCGA TCACCGTGCA GGTCAAGACC GTCGAGGAGG
2941 CCATGGAGCT CAGCAACAAG TACGCTCCTG AGCACTTGAT CCTCCAGATC AAGGAGGCCG
3001 AGAAAGCTGT CGATCTTGTC ATGAACGCTG GTAGTGTCTT CATTGGCGCT TGGACTCCTG
3061 AGTCCGTTGG CGATTACTCT GCTGGTGTTA ACCACTCGCT GCGTAAGTTA CATATCATAA
3121 ATAGCCCCGC TTCACAGATT CTTCTGCTAA CGTCAAGACA CATAGCTACC TATGGTTTTG
3181 GCAAGCAGTA CTCTGGCGTC AATCTCGCCT CGTTCGTCAA GCACATTACC AGCTCCAACT
3241 TGACTGCCGA GGGTCTCAAA AACGTCGGCC AGGCTGTCAT GCAGTTGGCT AAGGTTGAGG
3301 AGCTCGAGGC TCACAGAAGG GCGGTCAGCA TCCGTCTTGA GCACATGAGC AAGAGCAACT
3361 AGACGGAAAT TCTTTTTCGA AGTTGCAAAA AAAACAAGAA CAAAAGGATG TAGTGGGTTG
3421 ATGTATATCT GGGTCATTTT GGGCACATAG AGTAATGATA ACGAGTTTTG ACATTGTAC
3481 TGTTCTGTAC AGGCTGAAGA TCAGTACATG AATCTGTTGG TAAGTGTAGA GACCCAAACG
3541 TCCCTTGAGT TTTTCTCCCT GTTCCAGAGA GGTGCTCGTC CCTGGGTGTT TATTTTCATT
3601 ATTACATCAA CCTTTTATTT TATTTTATTT TTTATTTTAC TTTTTTTTCC TTTTTTTCAG
3661 ATCATGCGTA CATGAACGGG GGAAGCACAG ACGATCGAAA CGTGGATGTC ACAATGTCGC
3721 TGCAGTGATG CTGCATTGCA TGAAGCGCCC ATCTCAATAT ACTTGCAGTC TTGCGCGTTG
3781 CACGTGAACT TCCCAAACAA CCGAATAAAA GACGGCGAAA AATGAAGATA AAAAAAAACC
3841 ATAATAAAAA TCGGAGGGAG TGTGGGAAAT GGTTTCTTTT AGCATTAGA CCCCATAGCC
3901 GTGCACGCCC GGGTACAGAC AGGTTCATCG ATGTTGACAT TGACTGGGAC ACCAGGTCTA
3961 TCTATTTCAT CTCCTGTCCT CTACCATACA TCGGGACATC GGACATCTCG CTGTACCCCC
4021 CACACCCACA AAGTCTTATA AAAGCGCCAC ACCCGAGGAG GTTCGGTCGG CCCCACGAAC
4081 TCCGTGCCTC CCTGCCTGTT TACAGGGACC GAACGCTGGA GAAGCTTAGT TTCCTGACAT
4141 CCGGCCTACC CGAGCAGGAA AAGGGACAGC TCATAGGCGA GGAGGGATTT GAAGATGGGG
4201 ACATTTTGGA TGATTCGAGA GGAGGAACTA GGTACTGTAT CATGATAGTT CGGGGCAGCA
4261 TCTTGGCTGG GACATTGTTA ATACCTCGAT ATGATGAAGT GGGAGGGAGT TTTTTCATGT
4321 CTTGCCCAAG TCCCACTAAT CTTTTTTTTT TTTTGTACCA ACACCCAAGA TTCGGAGAAT
4381 AGTGTAAGGA TTCGCATTCA CAAGTGGAAG TCTGAGGATC TTTTTATATC TTTGTCTTCC
4441 GCGGACTGTT AACGATCCTA CAGCGAGCGA GCGAGCGGTC GGATGCGCTG ATCTGATAGG
4501 TGCAATATAC GGCCGCTTTC TCCGGTCGTG TAGTGTAAGC TCTGTCGGCA TAGTAGTACA
4561 CTAAAAAAAC CCTTGCATTT CATGATCTGC TTGCTATTCA TTCCGAGTTA TTTCAGTGGT
4621 CACATTTCGA GATTCACAGC CATCCATCCA TATGGAAAAA TCCATTCCCA TGCTTCCTCC
4681 CCCCCACTAT GTATGTGACC ACACGCTGCT GTCAGAATGC CAACGGTCTC AGGTACCCTC
4741 GTCCGACTGT TTGGCATGGA GTTACATACA CTACTAGTGT AGCCCCGGGC CAAGCTACCC
4801 CGTCAAATCT ATACATATCT ATAATGGGTT TCAGGTGTTT CGTTCGCTGT CAATCAAGTT
4861 TGAAACATCA CTGGGCCGT TGGACGGTGT ATTAGACCAT TGGCTCCCTC AGCTGGCGGC
4921 TGGGCGGTTG GGTCGGCAAT AACGGGACTG GACTTGAGAG GGACGAGGAG AGTCGGTTGG
4981 CTGCCTACAC TACACTACAA GCGTTCCCAC CTAACCGACG AGTCCCGTTT TCCATTTGTG
5041 TGCCTTAACC ATCATCTAGG GATGTCAGGG TTTGGCCGGA TCAGGGTATG TTTGGTTGAC
5101 TGTTGTCATG TCTGATTGGG TACATATCAT GGTAGGTGTC TCGAGAACAG TAGAGTACTC
5161 GGGCCTAGCG TTTGGATGAT TACGCGAGAT ATGAGTTGTA GGCCGCCATG CAGTTGCTTG
5221 CCCATAAGCA GAAGTTGCTT TGGGATATAT TTCTCGTCTT TCAAAGGTCA CGAGGTCCTG
5281 GGACGAGCGG CATCGCCATC CAAAGGGTTG AACATGAGAA ACCGGAATGG CCTTTGCGTT
5341 GAAATACAAA AAGTCAAGAA TAAATCGCT TGAGGATAGG GACGTGGAAG CAAGCAAATA
5401 TGGTAAGGGA GGTACTGCTA TGTAGGTGCT CAGCAAACTG CCAATTTCTT GGCCCCCAAG
5461 CAGCAGTTTG CTGTCAGTGC TGCTCGTGTC AGCCTTGGTA GTGGAACCTA AACTGCTAAC
5521 ACAGCGCAAG TGCGCATGTA AAGATATTGT GGGAGGATCT GTATGGATGG ATGAGATTAC
5581 TGCTTGGTGT TGGTTGCGAG GCACTGCGGC TGTTAGGCTT TGCTGTGCCC CGTTCGACGA
5641 AGAAATACGC GGAACTATAA ATTGGATACC TAGACTTACT GCCTATGGGA GGTATCTACC
5701 GACGTAGCCG ACGGATTCTA GCAACATCCC GACTTTGCTT GTAGTGTACT ATGATAGCAG
5761 CACAGTGGGG TGTTGCTCCT TGTGAGCATG GGCTCTTTTT TTTTTTTTCC CCCTTCCCTA
5821 GGGCGTTGAC TGGACTTGCT CTATCGTTCC CAAGGTAGGT GCCCGTCATC GATTTTCCCA
5881 AGCCGTCTCC CGCCAGATTG TCGTCATAGT GTCATGATGA CCTCGGTCGC TGGGCTGCG
5941 TGGTTACGGG GAGCTGGGAC CGCTAGGCCT CAGTGGTTGT GCCATTCAGC GTGGGTGTGT
6001 GGAGTAGCGG TAGAGGCGCT TGGAAGTTGT GCTAGCGGAA ACCCTGGAAT ATCTTGTACC
```

FIG. 7 continued

```
6061 CTTCGATTCC TTCTCGGGCT GCCCATGTGC TGAGGTGATG CCGGGGATCT GGCGCCAATC
6121 ATCCATTGAG GTTCCCGCAG CTTCCGGTG CCGCGCGCGG GCGCAGTTGC TCACAGGACA
6181 CACCTAGACG CAGGGGCACA GGGGCACCGT TTGGTGTGCA ACTGGGTACC TGGTAGCTGT
6241 AGCAAGCACT CCACCGTCTG TGCAATCCCC CAATCCACGG CAGGAACTTA GCACCGCCGC
6301 GGCACCGAGT GAGCGAATCC ATCCGCATTG GATCCCAATT CTTGCCCTTG CCATCCTTCT
6361 TTCTTCCCAC TTGGCGCAAC CAACACTTCC CTTGGTCTGG GTACTCGTGT TGATCTTCAC
6421 TCTCTTTTTT TCTTGGGCGA CCGACTTTTT ATATCCGTCC TTGCTTCCCC CTGGCCGTTG
6481 TCGTTCTTTC TACAACTACC TTCCGTTCAT TATCCCCTTT CTTGGTTCGG TCGAGGACCC
6541 AAAAACAGAA CAATTCCGGC TCTTCCAGGT GGCTTGGGTG CGACTGTTTA GCTCTTGACC
6601 ACTAGCCGCT TACCTTCTCT TGATGTTTAT ATTTGGATAT CATTGAACTA CTCTTTCTTG
6661 AAACGGCAGA CGAACGGAAC AGTCCCTACG GTTATTAGC GATATACGTT GTACTGATAT
6721 CCTGAGCAAG AAGAGGCAAA TTATCAATTA TGCATCTCCC ATCGTCGCTG CTCATCGCAG
6781 CTCCCTTGCT CGCCAATGTA TCGGCCGAAC CGATTAGGAT ACCCCAACGC GATGTTCTCC
6841 GTGGTATCAA CATCACAGCA ACTTGCCGTT CGAGCACTAC CGAATTCGCC CAGCGGTGGA
6901 TATGCCCCTG CCGTTGTAGA CTGTCCCAAG ACCAAGCCGA CGCTCCGGAA GGCCGTGGAT
6961 TTGTCGAACG AGGAGAAGAA CTGGTTGTCG ATCCGGAGGA AGAACACCAT CCAGCCCATG
7021 AGGGACCTAC TGAAGAGGGC CAACATCACT GGGTTCGATT CCGAAACTTT CATGAATGAG
7081 GCCGCCAACA ACGTCTCGCA ACTGCCCAAT GTCGCCATTG CCATTTCAGG AGGCGGCTAT
7141 CGTGCCCTCA TGAACGGCGC CGGCTTCGTT GCTGCTGCGG ATAACCGGAT TCAAAATACC
7201 ACGGGCGCAG GTGGTATTGG AGGCTTGTTG CAGTCCAGCA CATATTTGTA TGTAAAACCA
7261 TGCCTTCTTG TGGTTCTTCT TATCTCGTTT TCGAGTGTCA ACTGCGCCAG TTCGACGTTG
7321 GGCGGCTGTG GACGACCTTG CTGGTGAACA TGTCTTGGAC TCCATGCCCC TTTTTTCGTT
7381 CCCTAAAATC CCAAAAAAAA AAAAAAAAAA AAAAAAAAAA AAAAAAAAAA AAAATTCGAG
7441 GACCGTGACT GTAAATTGCT AACGCAACTC TAGGGCCGGA CTTTCTGGTG GTGGCTGGCT
7501 TGTCGGCAGT TTGTTCTCCA ACAACTTCAG TAGCATTGAG ACCCTGCTGA GCGAGAACAA
7561 AGTCTGGGAC TTTGAGAACT CCATCTTTAA AGGACCCAAG GAGGCTGGCC TTAGTACTGT
7621 CAACCGTATC CAGTACTGGT CCGAAGTGGC AAAGGAAGTT GCGAAGAAGA AGGATGCTGG
7681 CTTCGAGACA AGTATAACAG ACTACTGGGG CCGAGCATTG AGTTACCAAC TGATCGGAGC
7741 CGATATGGGC GGCCCGGCTT ACACCTTCTC CAGCATTGCC CAGACCGACA ACTTCCAGAA
7801 GGCCGAAACG CCGTTCCCTA TTCTGGTAGC TGACGGCCGC GCGCCTGGAG ACACCATCAT
7861 CTCCCTCAAT GCTACCAACT ACGAGTTCAA CCCGTTCGAG ACGGGTAGCT GGGACCCGAC
7921 CGTCTATGGC TTTGCGCCGA CCAAGTACCT CGGCGCCAAC TTCAGCAACG GCGTGATCCC
7981 ATCGGGAGGC AAGTGCGTTG AGGGTCTCGA CCAAGCCGGC TTCGTCATGG GCACCAGCAG
8041 CACGCTCTTC AACCAGTTCC TTTTGGCCAA CATCTCCAGC TACGACGGTG TTGCCAGACG
8101 TGCTCATCGA GGCCGTGACT TCTGTCCTCA AGGAAATCGG CGCCAAGAGG ACGACGTCTC
8161 CCAAATCATC CCTAATCCGT TCCTGGACTG GAACAACCGG ACCAACCCCA ACGCCGACAC
8221 GCTCGAGCTC GACCTGGTCG ACGGCGGCGA AGATCTGCAG AATATTCCGC TCAACCCGCT
8281 CACCCAACCC GTGCGCGCCG TCGACGTCAT CTTCGCTGTC GACTCGTCCG CCGACGTGAC
8341 AAACTGGCCC AATGGCACCG CCTGCGCGC CACCTACGAG CGCACTTTCG GCTCTATTTC
8401 CAACGGGACA CTCTTCCCCT CGATCCCCGA CGACTGGACG TTTATAAACC TAGGCCTCAA
8461 CAACCGCCCC TCTTTCTTCG GCTGCGATGT TAAGAACTTT ACCTTGAACG CCAACCAAAA
8521 GGTTCCCCCC TTAATCGTCT ATGTCCCCAA CGCGCCCTAT ACCGCGCTGA GCAACGTGTC
8581 CACCTTCGAT CCGTCATACA CGATGTCTCA GCGCAACGAC ATCATCGGCA ACGGATGGAA
8641 CTCAGCCACG CAGGGAAACG GCACGCTGGA TTCGGAGTGG CCCACTTGCG TCGCCTGCGC
8701 GGTTATCAGC AGGAGCTTAG ATCGGTTGGG CAGGCAGACG CCAGCCGCGT GCAAGACTTG
8761 CTTTGACAGG TATTGCTGGA ATGGCACAGT GAACTCCAAA GATACGGGGG TTTACATGCC
8821 TGAGTTCAAG ATTGCGGATG CGCATGCCCT GGACTCGGGT GCTGTTGCTA TCGGAAAGAT
8881 GGTGAATGTC TGGTCGTCGG TTGTGGTGGG AGTTGTGGCG GCTACTTTGT TGTTGTAGGG
8941 GTAGGGGAGA CGTGATGATA TTCCAGTCTG ATGAAGTTGA GACTGGACTG GAGATCGCCA
9001 AGGATGCGGA GGGAAAGGAA TGCGTGGTGT TAATGTCATG ATGGATGAAG AGTCATGGAT
9061 CATGGAACGA CGGGGCGGGG ATATTGGATG ATGGATATAC CACACTGCAT GCATGCTCTA
9121 TTGATAGTAT GCTTTGGCAT TTACGTTTAA CAATCAATTG CTCCATCCTG ATGTTCTATC
9181 TTTTTCGACA ATGGATTGAT ACTACTCCTG TTGCTTCGCT CTTGAGGTTG GAAGGACTTG
9241 AGGTTGGAAG GACTTGAGGT TGTTTGTTCT GAGGGAGGTT ATCGAAGTAT CATCTGTGCT
```

FIG. 7 continued

```
9301 GATGCCGATT GATAGACTGT CCTCTTCTTC GAGGCAACGA ACGGTCGGAT GAGCCTCTTT
9361 AATCATGATG CTCAGTGCCA CAAAAAGGCT CCAGCACAGC TGCCCACACC TTTCTTGCCT
9421 CGCCGTTCCT TCCTTTTTCT TTTCCCTGT  TTCCTTTCTT CCTTTCCATC TCATCCCGTA
9481 CCAGAGTGCC CACCGGGTAT ATATATTACC TCCTTGGCCG TTCTCCTTTG ACCAATAAAT
9541 CGCTTGGTCG AGTGGCGTAA CGGTTTACCG TCTACACTTA TCACTCAAAC CAAACCAAAC
9601 CATCGAAGAA GTGACCTATC GGTTCGAGGG AACGGTGATG TTCTTACGAC CAAGTTAACC
9661 CAAAGAGCGT TCCACATCGT TGAACCGTCT CCTCCAGTTG GATCTGTTTA ACTTCCGCAG
9721 CGACTGAAGA AGGTATCACT TTTTTTTTGG TTCCAAAAAA AAAAAAAAA  ATTAC
```

FIG. 8

Nucleotide sequence of the *his-3 cog^E lpl* region of linkage group I in the StLawrence wild type strain of *Neurospora crassa*. This differs from that in the Lindegren strain in many positions, summarised in figure 5. The coordinates of relevant features are given in the text. This sequence contains the weak recombinator *cog^E* and also the remnant of a transposable element *Guest* within the replaceable sequence 3' of *his-3*. StLawrence strains carry *rec-2⁺* which prevents the initiation of recombination at *cog*.

```
   1 ACCGGGAATC GTAGCGGGCG CTAAGGCCAA GCCGCGGCAC GGGTCACTGA CCCAATGCAG
  61 CGCATTCCGT CAGCAACTGA AGTGGATGTA CAAGTACATA GTAGTAGATC GCAACTGGAG
 121 ATCACTCGCA CCGTGCCGCA GAACAAGGGC GACGAGCCTC AGGGCAGTTT AGCCTGCCGT
 181 AACAGCACAG ACCATAGCTT ATTTTCACCT GGGCGGGCGG GCGACGGCGG CACTGACATC
 241 GGCAAGGCGG CATCAAGCAA CCCCTCTGTT GCTTGCCAGC TGCCGGCCAA CGTCAGCGGT
 301 ACAAGGAGAA ATCTGGAAGG AAAGACTTCT GGCACCGACA GGATGGCACG CGGGAAAAGT
 361 TCCCAATGCA TGAGATGAGG GGCATTTGCA TTGCCTCCCG TCACCCAGTG CGAACCCCAA
 421 CCCCACCATA GCGTCTGTCG ATACATGGAG CGCGAAGTCG AGAAACCTGT AATTCCTGGT
 481 AACTTTCAGG TACACAGTAC GTACTGATCC TGGTATCAAA CCTTGCCTGC CGAGTTTTCG
 541 ACGGAAAGAG GTGTGAATTG TGAAAGAGTC ATACCAAATC ACCCGATTTT CATAAAGCCC
 601 GAGTCTTTTC TGTACATAAG CGACACTCGA AGCGGGCCTC ATCTTCATAG CCTGATAGCT
 661 TGTAATACTC CATCCTCGTA TCTCACTTGA CCTTGAGTTC AACCCCACGT CAAACTTCAC
 721 CCGACACATC GACGGATTGG GGAACAGCAC AATACCTGAA AAGCGAGAAA ACCAAACAGA
 781 GGAAAACACC ATGGAGACAA CACTTCCCCT CCCCTTCCTC GTCGGTGTCA GTGTTCCTCC
 841 CGGACTGAAT GACATCAAGG AGGGCCTCAG CCGGGAGGAA GTCTCGTGTC TTGGCTGCGT
 901 CTTCTTCGAG GTCAAGCCCC AGACCCTTGA GAAAATCCTG CGATTCCTCA AGCGTCACAA
 961 TGTCGAATTT GAGCCCTACT TCGATGTAAC AGCCCTCGAG TCTATCGATG ATATTATCAC
1021 TCTTCTGGAC GCCGGCGCCC GCAAGGTGTT TGTCAAGACC GAGCAGTTGG CCGACCTCTC
1081 CGCATATGGC TCCCGCGTTG CCCCCATTGT CACTGGAAGC AGCGCTGCTT TGCTTTCCTC
1141 CGCCACCGAG AGCGGCCTTT TGCTCTCCGG CTTCGATCAG ACTGCCTCCG AGGCTGCACA
1201 GTTTCTGGAG GAGGCCAGAG ACAAGAAAAT TACCCCCTTC TTCATCAAGC CCGTTCCTGG
1261 GGCCGATCTC GAACAGTTCA TCCAGGTCGC CGCCAAGGCT AACGCCATCC CCATCCTGCC
1321 ATCCACTGGC TTGACAACAA AGAAGGACGA GGCCGGCAAG CTTGCCATCT CCACCATCCT
1381 CTCGAGCGTC TGGAAGTCTG ACCGTCCCGA TGGTCTTCTC CCCACCGTTG TCGTTGATGA
1441 GCACGACACT GCTCTGGGTC TGGTCTACAG CAGTGCCGAG AGTGTGAACG AGGCCCTCAG
1501 GACACAGACT GGTGTCTATC AGAGCCGGAA GCGCGGTCTC TGGTACAAGG GTGCTACTTC
1561 CGGAGACACT CAGGAGCTCG TCCGCATCTC GCTTGACTGC GATAACGATG CTCTCAAGTT
1621 TGTCGTGAAG CAGAAGGGTC GTTTCTGCCA CCTCGATCAG TCCGGCTGCT TTGGTCAGCT
1681 CAAAGGCCTT CCCAAGCTCG AGCAGACTTT GATTTCGAGG AAACAGTCTG CCCCCGAGGG
1741 CTCCTACACT GCCCGTCTCT TCTCCGATGA GAAGCTAGTC CGGGCCAAGA TCATGGAGGA
1801 GGCTGAGGAG CTCTGCACCG CTCAGACCCC CCAGGAAATC GCCTTTGAGG CTGCCGATCT
1861 CTTCTACTTT GCTCTTACCA GGGCCGTTGC TGCCGGCGTT ACTCTTGCCG ATATCGAAAG
1921 GAGCCTTGAC GCCAAGAGCT GGAAGGTCAA GCGCAGGACT GGAGATGCTA AGGGTAAGTG
1981 GGCTGAGAAG GAGGGCATCA AGCCTGCGGC GTCCGCTCTC GCTGCCACTT CGGCCCCTGT
2041 CACCAAGGAG GCCGCCCAGG AGACCACCCC TGAGAAGATC ACCATGAGAC GTTTCGACGC
2101 CTCCAAGGTC TCTACCGAGG AGCTCGATGC TGCTCTCAAG CGTCCTGCGC AAAAGTCGTC
2161 CGATGCCATC TACAAGATCA TTGTCCCCAT CATCGAGGAC GTCCGCAAGA ACGGCGACAA
2221 GGCTGTTCTG TCGTACACTC ACAAGTTCGA GAAGGCTACC TCTCTTACTA GCCCCGTCCT
2281 GAAGGCGCCC TTCCCCAAGG AGCTTATGCA GCTCCCTGAG GAGACCATTG CTGCCATCGA
2341 CGTGTCCTTC GAGAACATCC GCAAGTTCCA CGCCGCCCAG AAGGAGGAGA AGCCCCTCCA
2401 GGTCGAGACC ATGCCCGGTG TTGTCTGCAG CCGTTTCTCT CGTCCCATCG AGGCCGTCGG
2461 CTGCTACATC CCCGGCGGTA CCGCCGTTCT CCCCAGCACT GCCCTTATGC TGGGTGTTCC
2521 CGCCATGGTC GCCGGCTGCA ACAAGATTGT GTTCGCCTCT CCTCCCCGCG CCGACGGAAC
2581 CATCACTCCC GAGATTGTCC ACGTCGCTCA CAAGGTTGGG GCCGAGTCCA TCGTGCTTGC
2641 CGGCGGTGCC CAGGCCGTAG CTGCCATGGC CTACGGCACC GAGAGCATCA CCAAGGTCGA
2701 CAAGATTCTC GGCCCCGGTA ACCAGTTCGT CACTGCTGCC AAGATGTTCG TCAGCAACGA
```

FIG. 8 continued

```
2761 CACCAACGCT GCCGTTGGTA TTGACATGCC CGCTGGCCCG TCCGAGGTGC TGGTCATCGC
2821 TGACAAGGAC GCCAACCCCG CGTTCGTTGC CTCGGATCTC CTGTCCCAGG CTGAGCACGG
2881 CGTTGACAGT CAGGTCATCC TGATCGCTAT TGACCTCGAC GAGGAGCATC TTCAGGCTAT
2941 TGAGGACGAG GTTCACCGTC AGGCTACGGA GCTTCCTCGC GTCCAGATTG TCCGTGGCTC
3001 CATCGCCCAC TCGATCACCG TGCAGGTCAA GACCGTCGAG GAGGCCATGG AGCTCAGCAA
3061 CAAGTACGCT CCTGAGCACT TGATCCTCCA GATCAAGGAG GCCGAGAAGG CTGTCGATCT
3121 TGTCATGAAC GCCGGTAGTG TCTTCATTGG CGCCTGGACT CCTGAGTCCG TTGGCGATTA
3181 CTCTGCTGGT GTTAACCACT CGCTGCGTAA GTTACATATC ATAAATAGCC CCGCTTCACA
3241 GATTCTTCTG CTAACGTCAA GACACATAGC TACCTATGGC TTTGGCAAGC AGTACTCTGG
3301 CGTCAATTTC GCCTCGTTCG TCAAGCACAT TACCAGCTCC AACTTGACTG CCGAGGGTCT
3361 CAAAAACGTC GGCCAGGCTG TCATGCAGTT GGCTAAGGTT GAGGAGCTCG AGGCTCACAG
3421 AAGGGCGGTC AGCATCCGTC TTGAGCACAT GAGCAAGAGC AACTAAACGG AAATTCTTTT
3481 CGAAGTAGCA AAAAAAAAAA AAAAAAACAA GAACAAAAGG ATGTAGTGGG TTGATGTATA
3541 TCTGGGTCAT TTGGGCACA TAGAGTAATG ATAACGAGTT TTGGACATTG TACTGTTCTG
3601 TACAGGCTGA AGATCAGTAC ATGAATCTGT TGGTAAGTGT GGAGACCCAA ACGTCCCTTG
3661 AGTTTTTCTC CCTATTCCAG AGGTGCTCGT CCCTGGGTGT TTATTTTCAT TATTACATCA
3721 ACCTTTTTTT TTTTTTTTTT TTTTTCAGAT CATGCGTACA TGAACGGGGG AAGCACAGAC
3781 GATCGAAACG TGGATGTCAC AATGTCGCTG CAGTGATGCT GCATTGCATG AAGCGCCCAT
3841 CTCAATATAC TTGCAGTCTT GCACGTTGCA TGTGAACTTC CCAAACAACC GAATAAAAGA
3901 CGGCGAAAAA TGAAGATAAA AAAAAACCAT AAAAAAAATC AGAGGGAGTG TGGGAAATGG
3961 TGTCTTTTAG CATTCAGACC CCATAGCCGT GCACGCCCGG GTACAGACAG GTTCATCGAT
4021 GTTGACATTG ACTGGGACAC CAGGTCTATC TATTTTATCT CCTGTCCTCT ACCATACATC
4081 GGGACATCGG ACATCTTGCT GTACCCCCCA CACCCACAAA GCCTTATAAA AGCGCCACAC
4141 CCGAGGAGGT TCGGTCGGCC CCACGAACTC TGTGCCTCCC TGCCTGTTTA CAGGGACCGA
4201 ACGCTGGAGA ATCTTACTAG TTTCCTGACA TCCGGCCTAC CCGAGCAGGA AAAGGGACAG
4261 CTCATAGGCG AGGAGGGATT TGAAGATGGG AACATTTTGG GTGATTCGAG AGGAGGAACT
4321 AGGTACTGCA TCATGATAGT TCGGGCAGC ATCTTGGCTG GACATTGTT AATACCTCGA
4381 TATGATGAAG TAGGAGGGAG TTTTTGCGTG TCTTGCCGAA GTCCAGAGAT CTGTTTTATT
4441 TTATTTTTA TGGATGTAGT GTATCAACAC CCAAGATTCG GAGAATAGTA CTAGGATTCG
4501 CATTTACAAG TGGAAGTCTT GAGAATCGTT GTATATCCTT GTCTTCCTCG GAATGTTAAC
4561 AATCCTACAG CGAGCGAGCG AGCGGTCGGA TGCGCTGATC TGATAGGCGC AATATACGGC
4621 CGCTTTCTCC GGTCGTGTAG TGTAAGCTCT GTGGGCATAG TACACTAAAA AAACCCTTGC
4681 ATTTCATGAT CTGCCTGCTA TTCATTCCGA GCTATTTCAG TGGTCACATT TCGAGGAAGA
4741 AAGAAAGCAA CTAAGATTCA CAGCCATCCA TCCATCCATA TGGAAGAATA ATCCATTCCC
4801 ATGTTCCCTC CCCCCCACTA TGTATGTGAC CACACGCTGC TGTCAGAATG CCAACGGTCT
4861 CAGGTACCCT CGTCCGACTG TTTGGCATGG AGTTACATAC ACTACTAGTG TAGCCCCGGG
4921 CCAAGCTACC CCGTCAAATC TATACATATC TATAACGGGT TTCAGGGGTT TCGTTCGCTG
4981 TCAATCAAGT TTGAAACATC ACTGGGGCCC TTGGACGGTG TATTAGACCA TTGGCTCCCT
5041 CAGCTGTTTG GCGGCTGGGC GGCTGGGTCA AACGGCAATA ACGGGACTCG AGAGGGACGA
5101 GGAGAGTCGG TTGGCTGGCT GCAATACAAG CGTTCCCACC TAACCAACGA GTCCCGTTTT
5161 CCATTTGTGT GCCTAACCAT CATCTAGGGA TGTCAGGGTT TGGCCGGATC AGGGTATGTT
5221 TGGTTGACTG TTGTCATGTC TGATTGGGTA CATATTATGG TAGGTGTCTC GAGAACAGTA
5281 GAGTACTCGG GCCTAGCGTT TGGATGATTA CGCGAGATAT GAGTTGTGGG CCGCCATGCA
5341 GTTGCTTGTC CATAAGCAGA AGTTGCTTTG GGATATATTT CTCGTCTTTC AAAGGTCACG
5401 AGGTCCTGGG ACGAACGGCA TCGCCATCCA AAGGGTTGAA CATGAGAAAC CTGAATGGCC
5461 TTTGCGTTGA ATACAAAAA GTCAAGAACA AAATCGCTTG AGGATAGGGA CGTGGAAGCA
5521 AGCAAATATG GTAAGAGAGG TATACATCAA CCCTGGTTCA ATTGTTAGCG TGGTTCTTCC
5581 TCCACGTCCT CGTTCATGAC GGTTAACAGT ACCAGGCTAA CAATTAAACC AGGGTTGATG
5641 TGTACTGATA TGTAGGTGCT CAGCAAACTG CCAATTTCTT TGGCCCCAAG CAGCAGTTTG
5701 CTGTCAGTGC TGCTCGTGTC AGCCTTGGTA GTGGAACCTA AACTGCTAAC ACAGCGCAAG
5761 TGCGCATGTA AAGATATTGT GGGAGGATCT GTATGGATGG ATGAGATTAC TGCTTGGTGT
5821 TGGTTGCGAG GCACTGCGGC TGTTAGGCTT TGCTGTGCCC CGTTCGACGA AGAAATACGC
5881 GGAACTATAA ATTGGATACC TAGACTTACT GCCTATGGGA GGTATCTACC GACGTAGCCG
5941 ACGGATTCTA GCAACATCCC GACTTTGCTT GTAGTGTACT ATGATAGCAG CACAGTGTTG
```

FIG. 8 continued

```
6001 CTCCTTGTGA GAATGGGCTC TTTTTTTTTT TCCCCCTTCC CTAGGGCGTT GACTGGACTT
6061 GCTCTATTGT TCCCAAGGTA GGTGCCCGTC ATCGATTTTC CCAAGTCTCC CGCCAGATTG
6121 TCGTCATAGT GTCATGATGA CCTCGGTCGC TGGGGCTGCG TGGTTACGGG GAGCTGGGAC
6181 CGCTAGGCCT CAGTGGTTGT GCCATTCAGC GTGGGTGTGT GGAGTAGCGG TAGAGGCGCT
6241 TGGAAGTTGT GCTAGCGGAA ACCCTGGAAT ATCTTCTACC CTCGATTCCT TCTCGGGCTG
6301 CCCATGTGCT GAGGTGATGC CGGGGATCTG GCGCCAATCA TCCATTGAGG TTCCCGCAGC
6361 TTCCCGGTGC CGCGCGCGGG CGCAGTTGCT CACAGGACAC ACCTAGACGC AGGGGCACAG
6421 GGGCACCGTT TGGTGTGCAA CTGGGTACCT AGCTGTAGCA AGCACTCCAC CGTCTGTGCA
6481 ATCCCCCAAT CCACGGCAGG AACTTCGCAC CGCCGCGGCA CCGAGTGAGC GAATCCATCC
6541 GCATTGGATC CCAATTCTTG CCCTTGCCAT CCTTCTTTCT TCCCACTTGG CGCAACCAAC
6601 ACTTCCCTTG GTCTGGGTAC TCGTGTTGAT CTTCACTCTC TTTTTTTCTT GGGCGACCGA
6661 CTTTTTATAT CCGTCCTTGC TTCCCCCTGG CCGTTGTCGT TCTTTCTACA ACTACCTTCC
6721 GTTCATTATC CCCTTTCTTG GTTCGGTCGA GGACCCAAAA ACAGAACAAT TCCGGCTCTT
6781 CCAGGTGGCT TGGGTGCGAC TGTTTAGCTC TTGACCACTA GCCGCTTACC TTCTCTTGAT
6841 GTTTTTATTT GGATATCATT AAACTACTCT TTCTTGAAAC GGCAGACGAA CGGAACAGTT
6901 CCTACGGTAT ATTAGCGATA TACGTTGTAC TGATATTCTG AGCAAGAAGA GGCAAATTAT
6961 CAATTATGCA TCTCCCTTCG TCGCTGCTCA TCGCAGCTCC CTTGCTCGCC AATGTATCGG
7021 CCGAACCCAT TAGGATACCC CAACGCGATG TTCTCCGTGG TATCAACATC ACAGCAACTT
7081 GCCGTTCGAG CACTACCGGA TTCGCCCAGC GGTGGATATG CCCCTGCCGT TGTAGACTGT
7141 CCCAAGACCA AGCCGACGCT CCGGAAGGCC GTGGATTGT CGAACGAGGA GAAGAACTGG
7201 TTGTCGATCC GGAGGAAGAA CACCATCCAG CCCATGAGGG ACCTCCTGAA GAGGGCCAAC
7261 ATCACTGGGT TCGATTCCGA GACATTATG AATGAGGCCG CCAACAACAT CTCGCAACTG
7321 CCCAATGTCG CCATTGCCAT TTCAGGAGGC GGCTATCGTG CCCTCATGAA CGGCGCCGGC
7381 TTCGTTGCTG CTGCGGATAA CCGAATTCAA AATACCACGG GCGCAGGTGG TATTGGAGGC
7441 TTGTTGCAGT CCAGCACATA TTTGTATGTA AAGTGGTTCT TCTTATCTCG TTTTCGAGTG
7501 TCAACTGCGC CAGTTCAGAG TTGGGCGGCT GTGGACGACC TTGCTGGTGA ACATGTCTTG
7561 GACTCCATGC CCCTTCTTCG TTTCCTCAAA TCAAGAAGTC GAGGACCGTG ACCGTAAATC
7621 GCTAACGCAA CTCTAGGGCC GGACTTTCTG GTGGTGGCTG GCTTGTCGGC AGTTTGTTCT
7681 CCAACAACTT CAGCAGCATT GAGACCCTGC TGAGCGAGAA CAAAGTCTGG GACTTTGAGA
7741 ACTCCATCTT TAAAGGGCCC AAGGAGGCTG GCCTTAGTAC TGTCAACCGC ATTCAGTACT
7801 GGTCCGAAGT GGCAAAGGAA GTTGCCAAGA AGAAGGATGC TGGCTTCGAG ACAAGTATAA
7861 CAGACTACTG GGGCCGAGCA TTGAGTTACC AACTGATCGG AGCCGATATG GGCGGCCCGG
7921 CTTACACCTT CTCCAGCATT GCCCAGACCG ACAACTTCCA GAAGGCCGAA ACGCCGTTCC
7981 CTATTCTGGT AGCTGACGGC CGCGCGCCTG GAGACACCAT CATCTCCCTC AATGCTACCA
8041 ACTACGAGTT CAACCCGTTC GAGACGGGTA GCTGGGACCC GACCGTCTAT GGCTTTGCGC
8101 CGACCAAGTA CCTCGGCGCC AACTTCAGCA ACGGCGTGAT CCCATCGGGA GGCAAGTGCG
8161 TTGAGGGTCT CGACCAAGCC GGCTTCGTCA TGGGCACCAG CAGCACGCTC TTCAACCAGT
8221 TCCTTTTGGC CAACATCTCC AGCTACGACG GTGTTGCCCG ACGTGCTCAT CGAAGCCGTG
8281 ACTTCTGTCC TCAAGGAAAT CGGCGCCAAG AGGACGACGT CTCCCAAATC ATCCCTAATC
8341 CGTTCCTGGA CTGGAACAAC CGGACCAACC CCAACGCCGA CACGCTCGAG CTCGACCTGG
8401 TCGACGGCGG CGAAGATCTG CAGAATATTC CGCTCAACCC GCTCACCCAA CCCGTGCGCG
8461 CCGTGGACGT CATCTTCGCT GTCGACTCGT CCGCCGACGT GACAAACTGG CCCAATGGCA
8521 CCGCCCTGCG AGCCACCTAC GAGCGCACTT TCGGCTCTAT TTCCAACGGG ACACTCTTCC
8581 CCTCGATCCC CGACGACTGG ACGTTTATAA ACCTAGGCCT CAACAACCGC CCCTCTTTCT
8641 TCGGCTGCGA TGTTAAGAAC TTTACCTTGA ACGCCAACCA AAAGGTTCCC CCCTTAATCG
8701 TCTATGTCCC CAACGCGCCC TATACCGCGC TGAGCAACGT GTCCACCTTC GATCCGTCAT
8761 ACACCATGTC TCAGCGCAAC GACATCATCG GCAACGGATG GAACTCAGCC ACGCAGGGAA
8821 ACGGCACGCT GGATTCGGAG TGGCCCACTT GCGTCGCCTG CGCGGTTATC AGCAGGAGCT
8881 TAGATCGGTT GGGCAGGCAG ACGCCAGCCG CGTGCAAGAC TTGCTTTGAG AGGTATTGCT
8941 GGAATGGCAC AGTGAACTCA AAAGATACAG GGGTTTACAT GCCTGAGTTC AAGATTGCGG
9001 ATGCGCATGC CCTGGACTCG GGTGCTGTTG CTATCGGAAA GATGGTGAAT GTCTGGTCGT
9061 CGGTTGTGGT GGGAGTTGTG GCGGCTACTT TGTTGTTGTA GGGGTAGGGG AGACGTGATG
9121 ATATTCCAGT CTGATGAAGT TGAGACTGGA CTGGAGATCG CCAAGGATGC GGAGGGAAAG
9181 GAATGCGTGG TGTTAATGTC ATGATGGATG AAGGGTCATG GATCATGGAA CGACGGGGCG
```

FIG. 8 continued

```
9241 GGGATATTGG ATGATGGATA TACCACACTG CATGCATGCT CTATTGATAA TATGCTTTGG
9301 CATTTACGTT TAACAATCAA TTGCTCCATC CTGATGTTCT ATCTTTCGAC ACTGGATTGA
9361 TACTACTCCT GTTGCTTCCC TCTTGAAGTT GGAAGGACTT GAGGTTGGAA GGACTTGAGG
9421 TTGTTTGTTC TGAGGGAGGT TATCGAAGTA TCATCTGTGC TGATGCCGAT CGATAGACTG
9481 CCCTCTTCTT CGAGGCAACG AACGGTCGGA TGAGCCTCTA ATCATGATGC TCAGTGCCAC
9541 AAAAAGGCTC CAGCACAGCT GCCCACACCT TTTTTGCCTC GTCGCTCCTT CCTTTTTTTC
9601 CCCCCCTTTC TTCCTTTCCA TCTCATCCCG TACCAGAGTG CCCACCGGGT ATATATATTA
9661 CCTCCTTGGC CGTTCTCCTT TGACCAATAA ATCGCTTGGT CGAGTGGCGT AACCGTTTAC
9721 CGTCTACACT TATCACTCAA ACCAAACCAA ACCATCGAAG AAGTTACCTA TCGGTTCGAG
9781 GGAACGGTGA TGTTCTTACG TTCAAGTTAA CCCAAAGAGC GTTCCACATC GTTGAACCGT
9841 CTCCTCCAGT TCTTGGATCT GTTTAACTTC CGCAGCGACT GAAGAAGTAA TCACTTTTTT
9901 TTTTTTTGGT TCCAAAAAAA AAAAAAAAAA TTAC
```

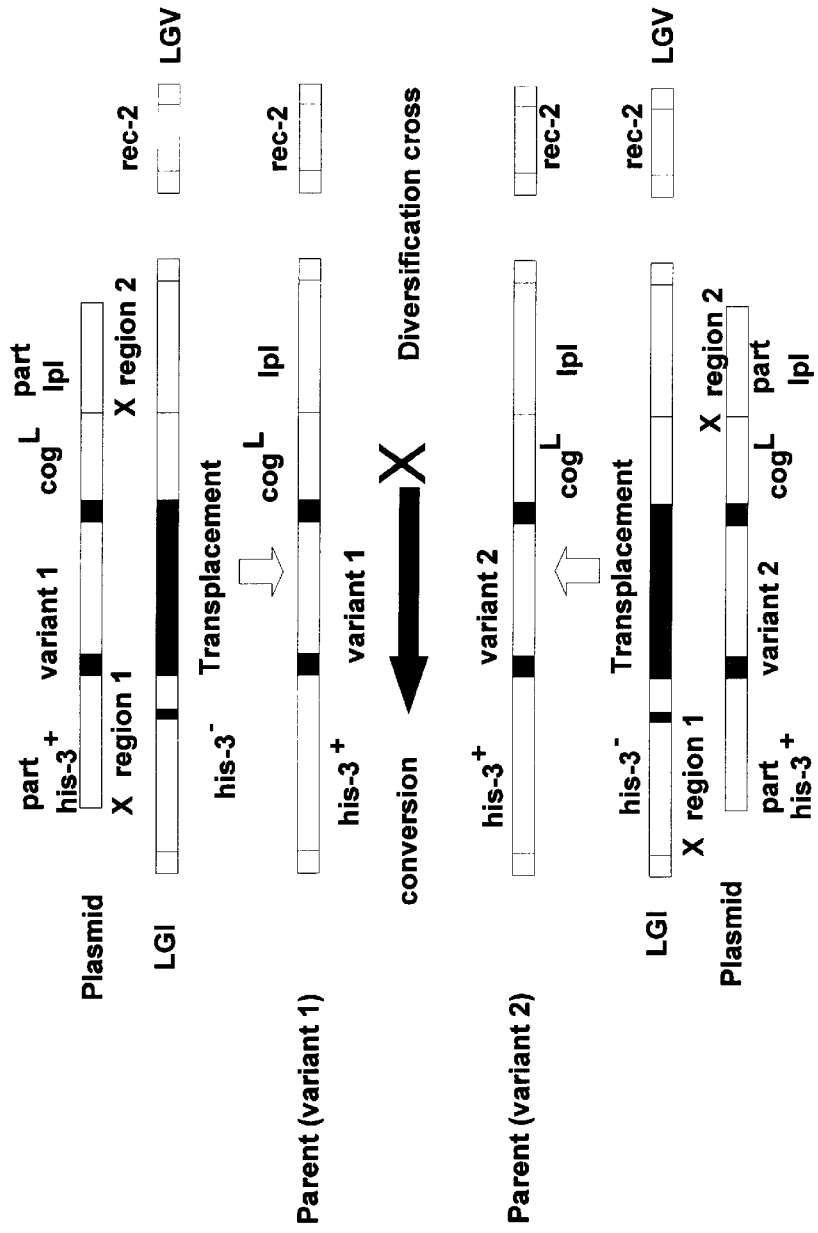

FIG. 9

Construction of the components of the sequence diversification cross: Parent (variant 1) and Parent (variant 2). For convenience, plasmid sequences are shown as linear. The cross hatched region in the chromosome is dispensible. Stippled sequence in the plasmid indicate the multiple cloning site for inserting foreign DNA. Crossovers in region 1 and region 2 insert the foreign sequence to be diversified into chromosome 1 of *Neurospora crassa* adjacent to the recombination hotspot *cog*. Parent (variant 2) containing a version of the foreign sequence with multiple differences from that in parent (variant1) is simularly constructed. Parent (variant 1) and parent (variant 2) are crossed and conversion events (stippled arrow) initiated (X) at $cog^-$ recombine the sequence differences in variant 1 and variant 2 to form new combinations. Sequences are identical except for those that distinguish variant 1 and variant 2. *rec-2* on linkage group V permits $cog^L$ to be active. For simplicity, genes not directly related to the diversification are omitted. See text for further details.

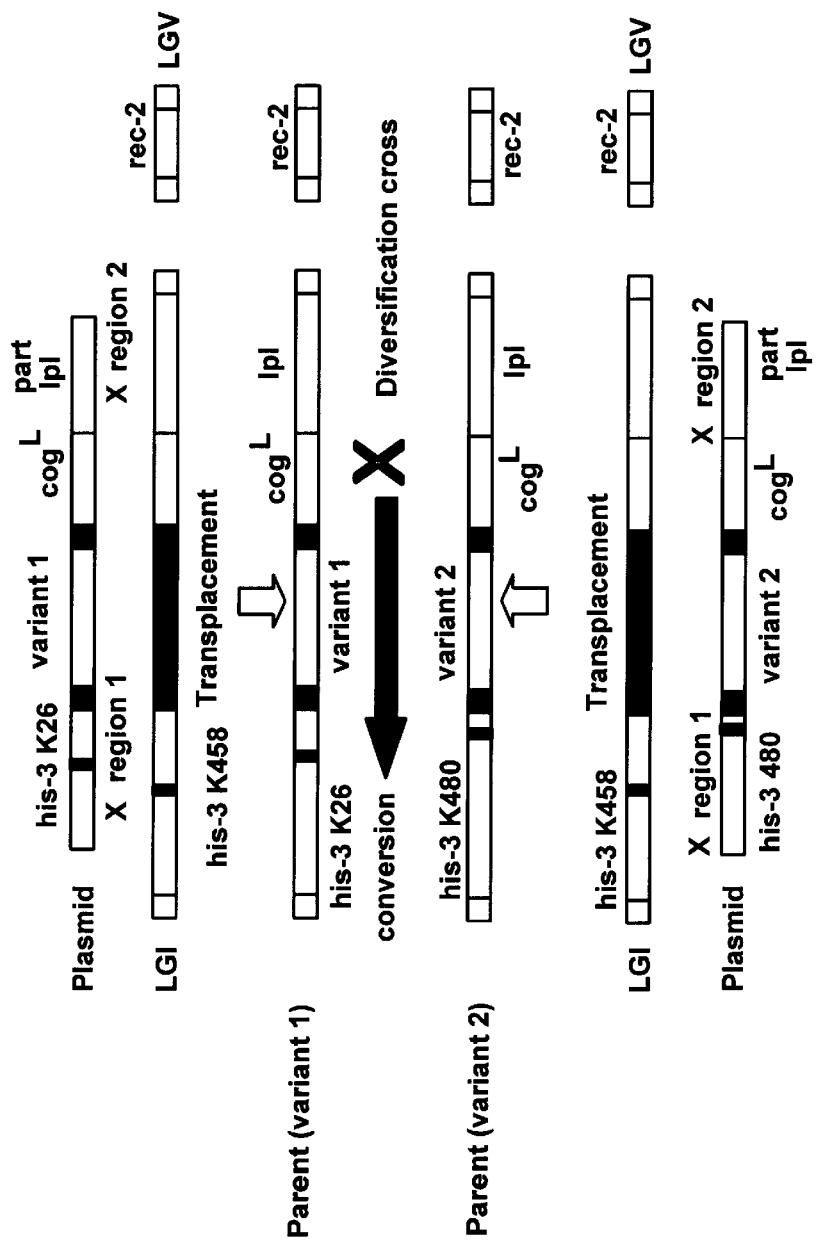

FIG. 10

Construction of parent (variant 1) and parent (variant 2) enabling selection of progeny that have experienced conversion in the foreign DNA. Complementing pairs of *his-3* alleles are used to obtain parent (variant 1) and a different pair of complementing *his-3* alleles are used to obtain parent (variant 2) as explained in the text. Parent (variant 1) and parent (variant 2) are crossed and *his+* recombinants are selected. These must all have experienced conversion events affecting the foreign DNA since the events begin at *cog^L*. The *his-3* alleles in parent (variant 1) and parent (variant 2) are non complementing to ensure that selection yields recombinants and not aneuploid progeny having two copies of all or part of linkage group I.

FIG. 12

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 9775 base pairs
      (B) TYPE: nucleic acid
      (C) STRANDEDNESS: single
      (D) TOPOLOGY: linear (ii) MOLECULE TYPE: Genomic DNA (xi) SEQUENCE DESCRIPTION: SEQ ID NO:1:

```
GATCGCAACT GGAGATCACT CGCACCGTGC CGCAGAACAA GGGCGACGAG CCTCAGGGCA      60

GTTTAGCCTG CCGTAACAGC ACAGACCATA GCTTATTTTC ACCTGGGCGG GCGGGCGACG     120

GCGGCACTGA CATCGGCAAG GCGGCATCAA GCAACCCCTC TGTTGCTTGC CAGCTGCCGG     180

CCAACGTCAG CGGTACAAGG AGAAATCTGG AAGGAAAGAC TTCTGGCACC GACAGGATGG     240

CACGCGGGAA AAGTTCCCAA TGCATGAGAT GAGGGGCATT TGCATTGCCT CCCGTCACAC     300

TGCCCGCGAA CCCCAACCCC ACCATAGCGT CTGTCGATAC ATGGAGCGCG AAGTCGAGAA     360

ACCTGTAATT CCTGGTAACT TTCAGGTACA CAGTACGTAC TGATCCTGGT ATCAAACCTT     420

GCCTGCCGAG TTTTCGACGG AAAGAGGTGT GAATTGTGAA AGAGTCATAC CAAATCACCC     480

GATTTTCATA AAGCCCGAGT CTTTTCTGTA CATAAGCGAC ACTCGAAGCG GGCCTCATCT     540

TCATAGCCTG ATAGCTTGTA ATACTCCATC CTCGTATCTC ACTTGACCTT GAGTTCAACC     600

CCACGTCAGA CTTCACCCGA CACATCGACG GATTGGGGAA CAGCACAATA CCTGAAAAGC     660

GAGAAAACCA AACAGAGGAA AACACCATGG AGACAACACT TCCCCTCCCC TTCCTCGTCG     720

GTGTCAGTGT TCCTCCCGGA CTGAATGACA TCAAGGAGGG CCTCAGCCGG GAGGAAGTCT     780

CGTGTCTTGG CTGCGTCTTC TTCGAGGTCA AGCCCAAGAC CCTTGAGAAA ATCGTGCGAT     840

TCCTCAAGCG TCACAATGTC GAATTTGAGC CCTACTTCGA TGTAACAGCC CTCGAGTCTA     900

TCGATGATAT TATCACTCTT CTGGACGCCG CGCCCGCAA GGTGTTTGTC AAGACCGAGC     960

AGTTGGCCGA CCTCTCCGCA TATGGCTCCC GCGTTGCCCC CATTGTCACT GGAAGCAGCG    1020

CTGCTTTGCT TTCCTCCGCC ACCGAGAGCG GCCTTTTGCT CTCCGGCTTC GATCAGACTG    1080

CCTCCGAGGC TGCACAGTTT CTGGAGGAGG CCAGAGACAA GAAAATTACC CCCTTCTTCA    1140

TCAAGCCCGT TCCTGGGGCC GATCTCGAAC AGTTCATCCA GGTCGCCGCC AAGGCTAACG    1200

CCATCCCCAT CCTGCCATCC ACTGGCTTGA CAACAAAGAA GGACGAGGCC GGAAAGCTTG    1260

CCATCTCCAC CATCCTCTCG AGCGTCTGGA AGTCTGACCG TCCCGATGGT CTGCTCCCCA    1320

CCGTTGTCGT TGATGAGCAC GACACTGCTC TGGGTCTGGT CTACAGCAGT GCCGAGAGTG    1380

TGAACGAGGC CCTCAGGACA CAGACTGGTG TCTATCAGAG CCGGAAGCGC GGTCTCTGGT    1440

ACAAGGGTGC TACTTCCGGA GACACTCAGG AGCTCGTCCG CATCTCGCTT GACTGCGATA    1500

ACGATGCTCT CAAGTTTGTC GTGAAGCAGA AGGGTCGTTT CTGCCACCTC GATCAGTCCG    1560

GCTGCTTTGG TCAGCTCAAA GGCCTTCCCA AGCTCGAGCA GACTTTGATT TCGAGGAAAC    1620

AGTCTGCCCC CGAGGGCTCC TACACTGCCC GTCTCTTCTC CGATGAGAAG CTAGTCCGGG    1680

CCAAGATCAT GGAGGAGGCT GAGGAGCTCT GCACCGCTCA GACCCCCCAG GAAATCGCCT    1740

TTGAGGCTGC CGATCTCTTC TACTTTGCTC TTACCAGGGC CGTTGCTGCC GGCGTTACTC    1800

TTGCCGATAT CGAAAGGAGC CTTGACGCCA AGAGCTGGAA GGTCAAGCGC AGGACTGGAG    1860

ATGCTAAGGG TAAGTGGGCT GAGAAGGAGG GCATCAAGCC TGCGGCGTCC GCTCCCGCTG    1920

CCACTTCGGC CCCTGTCACC AAGGAGGCCG CCCAGGAGAC CACCCCTGAG AAGATCACCA    1980

TGAGACGTTT CGACGCCTCC AAGGTCTCTA CCGAGGAGCT CGATGCTGCT CTCAAGCGTC    2040

CTGCGCAAAA GTCGTCCGAT GCCATCTACA AGATCATTGT CCCCATCATC GAGGACGTCC    2100

GCAAGAACGG CGACAAGGCT GTTCTGTCGT ACACTCACAA GTTCGAGAAG CTACCTCTC     2160

TTACTAGCCC CGTCCTGAAG GCGCCCTTCC CCAAGGAGCT TATGCAGCTC CCTGAGGAGA    2220

CCATTGCTGC CATCGACGTG TCCTTCGAGA ACATCCGCAA GTTCCACGCC GCCCAGAAGG    2280
```

```
AGGAGAAGCC CCTCCAGGTC GAGACCATGC CCGGTGTTGT CTGCAGCCGT TTCTCTCGTC    2340

CCATCGAGGC CGTCGGCTGC TACATCCCCG GCGGTACCGC CGTTCTCCCC AGCACTGCCC    2400

TTATGCTGGG TGTTCCCGCC ATGGTCGCCG GCTGCAACAA GATTGTGTTC GCCTCTCCTC    2460

CCCGCGCCGA CGGAACCATC ACTCCCGAGA TTGTCCACGT CGCTCACAAG GTTGGGGCCG    2520

AGTCCATCGT GCTTGCCGGC GGTGCCCAGG CCGTAGCTGC CATGGCCTAC GGCACCGAGA    2580

GCATCACCAA GGTCGACAAG ATTCTCGGCC CCGGTAACCA GTTCGTCACT GCTGCCAAGA    2640

TGTTCGTCAG CAACGACACC AACGCTGCCG TTGGGATTGA CATGCCCGCT GGCCCGTCCG    2700

AGGTGCTGGT CATCGCTGAC AAGGACGCCA ACCCCGCGTT CGTTGCCTCG GATCTCCTGT    2760

CCCAGGCTGA GCACGGCGTT GACAGTCAGG TCATCCTGAT CGCTATTAAC CTCGACGAGG    2820

AGCATCTTCA GGCTATTGAG GACGAGGTTC ACCGTCAGGC TATGGAGCTT CCTCGCGTCC    2880

AGATTGTCCG TGGCTCCATC GCCCACTCGA TCACCGTGCA GGTCAAGACC GTCGAGGAGG    2940

CCATGGAGCT CAGCAACAAG TACGCTCCTG AGCACTTGAT CCTCCAGATC AAGGAGGCCG    3000

AGAAAGCTGT CGATCTTGTC ATGAACGCTG GTAGTGTCTT CATTGGCGCT GGACTCCTG    3060

AGTCCGTTGG CGATTACTCT GCTGGTGTTA ACCACTCGCT GCGTAAGTTA CATATCATAA    3120

ATAGCCCCGC TTCACAGATT CTTCTGCTAA CGTCAAGACA CATAGCTACC TATGGTTTTG    3180

GCAAGCAGTA CTCTGGCGTC AATCTCGCCT CGTTCGTCAA GCACATTACC AGCTCCAACT    3240

TGACTGCCGA GGGTCTCAAA AACGTCGGCC AGGCTGTCAT GCAGTTGGCT AAGGTTGAGG    3300

AGCTCGAGGC TCACAGAAGG GCGGTCAGCA TCCGTCTTGA GCACATGAGC AAGAGCAACT    3360

AGACGGAAAT TCTTTTTCGA AGTTGCAAAA AAAACAAGAA CAAAAGGATG TAGTGGGTTG    3420

ATGTATATCT GGGTCATTTT GGGCACATAG AGTAATGATA ACGAGTTTTG GACATTGTAC    3480

TGTTCTGTAC AGGCTGAAGA TCAGTACATG AATCTGTTGG TAAGTGTAGA GACCCAAACG    3540

TCCCTTGAGT TTTTCTCCCT GTTCCAGAGA GGTGCTCGTC CCTGGGTGTT TATTTTCATT    3600

ATTACATCAA CCTTTTATTT TATTTTATTT TTTATTTTAC TTTTTTTTCC TTTTTTTCAG    3660

ATCATGCGTA CATGAACGGG GGAAGCACAG ACGATCGAAA CGTGGATGTC ACAATGTCGC    3720

TGCAGTGATG CTGCATTGCA TGAAGCGCCC ATCTCAATAT ACTTGCAGTC TTGCGCGTTG    3780

CACGTGAACT TCCCAAACAA CCGAATAAAA GACGGCGAAA AATGAAGATA AAAAAAAACC    3840

ATAATAAAAA TCGGAGGGAG TGTGGGAAAT GGTTTCTTTT AGCATTTAGA CCCCATAGCC    3900

GTGCACGCCC GGGTACAGAC AGGTTCATCG ATGTTGACAT TGACTGGGAC ACCAGGTCTA    3960

TCTATTTCAT CTCCTGTCCT CTACCATACA TCGGGACATC GGACATCTCG CTGTACCCCC    4020

CACACCCACA AAGTCTTATA AAAGCGCCAC ACCCGAGGAG GTTCGGTCGG CCCCACGAAC    4080

TCCGTGCCTC CCTGCCTGTT TACAGGGACC GAACGCTGGA GAAGCTTAGT TTCCTGACAT    4140

CCGGCCTACC CGAGCAGGAA AAGGGACAGC TCATAGGCGA GGAGGGATTT GAAGATGGGG    4200

ACATTTGGA TGATTCGAGA GGAGGAACTA GGTACTGTAT CATGATAGTT CGGGGCAGCA    4260

TCTTGGCTGG GACATTGTTA ATACCTCGAT ATGATGAAGT GGGAGGGAGT TTTTCATGT    4320

CTTGCCCAAG TCCCACTAAT CTTTTTTTTT TTTTGTACCA ACACCCAAGA TCGGAGAAT    4380

AGTGTAAGGA TTCGCATTCA CAAGTGGAAG TCTGAGGATC TTTTTATATC TTTGTCTTCC    4440

GCGGACTGTT AACGATCCTA CAGCGAGCGA GCGAGCGGTC GGATGCGCTG ATCTGATAGG    4500

TGCAATATAC GGCCGCTTTC TCCGGTCGTG TAGTGTAAGC TCTGTCGGCA TAGTAGTACA    4560

CTAAAAAAAC CCTTGCATTT CATGATCTGC TTGCTATTCA TTCCGAGTTA TTTCAGTGGT    4620

CACATTTCGA GATTCACAGC CATCCATCCA TATGGAAAAA TCCATTCCCA TGCTTCCTCC    4680
```

```
CCCCCACTAT GTATGTGACC ACACGCTGCT GTCAGAATGC AACGGTCTC  AGGTACCCTC      4740

GTCCGACTGT TTGGCATGGA GTTACATACA CTACTAGTGT AGCCCCGGGC CAAGCTACCC      4800

CGTCAAATCT ATACATATCT ATAATGGGTT TCAGGTGTTT CGTTCGCTGT CAATCAAGTT      4860

TGAAACATCA CTGGGGCCGT TGGACGGTGT ATTAGACCAT TGGCTCCCTC AGCTGGCGGC      4920

TGGGCGGTTG GGTCGGCAAT AACGGGACTG GACTTGAGAG GGACGAGGAG AGTCGGTTGG      4980

CTGCCTACAC TACACTACAA GCGTTCCCAC CTAACCGACG AGTCCCGTTT TCCATTTGTG      5040

TGCCTTAACC ATCATCTAGG GATGTCAGGG TTTGGCCGGA TCAGGGTATG TTTGGTTGAC      5100

TGTTGTCATG TCTGATTGGG TACATATCAT GGTAGGTGTC TCGAGAACAG TAGAGTACTC      5160

GGGCCTAGCG TTTGGATGAT TACGCGAGAT ATGAGTTGTA GGCCGCCATG CAGTTGCTTG      5220

CCCATAAGCA GAAGTTGCTT TGGGATATAT TTCTCGTCTT TCAAAGGTCA CGAGGTCCTG      5280

GGACGAGCGG CATCGCCATC CAAAGGGTTG AACATGAGAA ACCGGAATGG CCTTTGCGTT      5340

GAAATACAAA AAGTCAAGAA TAAAATCGCT TGAGGATAGG GACGTGGAAG CAAGCAAATA      5400

TGGTAAGGGA GGTACTGCTA TGTAGGTGCT CAGCAAACTG CCAATTTCTT GGCCCCCAAG      5460

CAGCAGTTTG CTGTCAGTGC TGCTCGTGTC AGCCTTGGTA GTGGAACCTA AACTGCTAAC      5520

ACAGCGCAAG TGCGCATGTA AAGATATTGT GGGAGGATCT GTATGGATGG ATGAGATTAC      5580

TGCTTGGTGT TGGTTGCGAG GCACTGCGGC TGTTAGGCTT TGCTGTGCCC CGTTCGACGA      5640

AGAAATACGC GGAACTATAA ATTGGATACC TAGACTTACT GCCATGGGA  GGTATCTACC      5700

GACGTAGCCG ACGGATTCTA GCAACATCCC GACTTTGCTT GTAGTGTACT ATGATAGCAG      5760

CACAGTGGGG TGTTGCTCCT TGTGAGCATG GGCTCTTTTT TTTTTTTCC  CCCTTCCCTA      5820

GGGCGTTGAC TGGACTTGCT CTATCGTTCC CAAGGTAGGT GCCCGTCATC GATTTTCCCA      5880

AGCCGTCTCC CGCCAGATTG TCGTCATAGT GTCATGATGA CCTCGGTCGC TGGGGCTGCG      5940

TGGTTACGGG GAGCTGGGAC CGCTAGGCCT CAGTGGTTGT GCCATTCAGC GTGGGTGTGT      6000

GGAGTAGCGG TAGAGGCGCT TGGAAGTTGT GCTAGCGGAA ACCCTGGAAT ATCTTGTACC      6060

CTTCGATTCC TTCTCGGGCT GCCCATGTGC TGAGGTGATG CCGGGGATCT GGCGCCAATC      6120

ATCCATTGAG GTTCCCGCAG CTTCCCGGTG CCGCGCGCGG GCGCAGTTGC TCACAGGACA      6180

CACCTAGACG CAGGGGCACA GGGGCACCGT TTGGTGTGCA ACTGGGTACC TGGTAGCTGT      6240

AGCAAGCACT CCACCGTCTG TGCAATCCCC CAATCCACGG CAGGAACTTA GCACCGCCGC      6300

GGCACCGAGT GAGCGAATCC ATCCGCATTG GATCCCAATT CTTGCCCTTG CCATCCTTCT      6360

TTCTTCCCAC TTGGCGCAAC CAACACTTCC CTTGGTCTGG GTACTCGTGT TGATCTTCAC      6420

TCTCTTTTTT TCTTGGGCGA CCGACTTTTT ATATCCGTCC TTGCTTCCCC CTGGCCGTTG      6480

TCGTTCTTTC TACAACTACC TTCCGTTCAT TATCCCCTTT CTTGGTTCGG TCGAGGACCC      6540

AAAAACAGAA CAATTCCGGC TCTTCCAGGT GGCTTGGGTG CGACTGTTTA GCTCTTGACC      6600

ACTAGCCGCT TACCTTCTCT TGATGTTTAT ATTTGGATAT CATTGAACTA CTCTTTCTTG      6660

AAACGGCAGA CGAACGGAAC AGTCCCTACG GTTTATTAGC GATATACGTT GTACTGATAT      6720

CCTGAGCAAG AAGAGGCAAA TTATCAATTA TGCATCTCCC ATCGTCGCTG CTCATCGCAG      6780

CTCCCTTGCT CGCCAATGTA TCGGCCGAAC CGATTAGGAT ACCCCAACGC GATGTTCTCC      6840

GTGGTATCAA CATCACAGCA ACTTGCCGTT CGAGCACTAC CGAATTCGCC CAGCGGTGGA      6900

TATGCCCCTG CCGTTGTAGA CTGTCCCAAG ACCAAGCCGA CGCTCCGGAA GGCCGTGGAT      6960

TTGTCGAACG AGGAGAAGAA CTGGTTGTCG ATCCGGAGGA AGAACACCAT CCAGCCCATG      7020
```

-continued

```
AGGGACCTAC TGAAGAGGGC CAACATCACT GGGTTCGATT CCGAAACTTT CATGAATGAG    7080

GCCGCCAACA ACGTCTCGCA ACTGCCCAAT GTCGCCATTG CCATTTCAGG AGGCGGCTAT    7140

CGTGCCCTCA TGAACGGCGC CGGCTTCGTT GCTGCTGCGG ATAACCGGAT TCAAAATACC    7200

ACGGGCGCAG GTGGTATTGG AGGCTTGTTG CAGTCCAGCA CATATTTGTA TGTAAAACCA    7260

TGCCTTCTTG TGGTTCTTCT TATCTCGTTT TCGAGTGTCA ACTGCGCCAG TTCGACGTTG    7320

GGCGGCTGTG GACGACCTTG CTGGTGAACA TGTCTTGGAC TCCATGCCCC TTTTTTCGTT    7380

CCCTAAAATC CCAAAAAAAA AAAAAAAAA AAAAAAAAA AAAAAAAAAA AAAATTCGAG     7440

GACCGTGACT GTAAATTGCT AACGCAACTC TAGGGCCGGA CTTTCTGGTG GTGGCTGGCT    7500

TGTCGGCAGT TTGTTCTCCA ACAACTTCAG TAGCATTGAG ACCCTGCTGA GCGAGAACAA    7560

AGTCTGGGAC TTTGAGAACT CCATCTTTAA AGGACCCAAG GAGGCTGGCC TTAGTACTGT    7620

CAACCGTATC CAGTACTGGT CCGAAGTGGC AAAGGAAGTT GCGAAGAAGA AGGATGCTGG    7680

CTTCGAGACA AGTATAACAG ACTACTGGGG CCGAGCATTG AGTTACCAAC TGATCGGAGC    7740

CGATATGGGC GGCCCGGCTT ACACCTTCTC CAGCATTGCC CAGACCGACA ACTTCCAGAA    7800

GGCCGAAACG CCGTTCCCTA TTCTGGTAGC TGACGGCCGC GCGCCTGGAG ACACCATCAT    7860

CTCCCTCAAT GCTACCAACT ACGAGTTCAA CCCGTTCGAG ACGGGTAGCT GGGACCCGAC    7920

CGTCTATGGC TTTGCGCCGA CCAAGTACCT CGGCGCCAAC TTCAGCAACG GCGTGATCCC    7980

ATCGGGAGGC AAGTGCGTTG AGGGTCTCGA CCAAGCCGGC TTCGTCATGG GCACCAGCAG    8040

CACGCTCTTC AACCAGTTCC TTTTGGCCAA CATCTCCAGC TACGACGGTG TTGCCAGACG    8100

TGCTCATCGA GGCCGTGACT TCTGTCCTCA AGGAAATCGG CGCCAAGAGG ACGACGTCTC    8160

CCAAATCATC CCTAATCCGT TCCTGGACTG GAACAACCGG ACCAACCCCA ACGCCGACAC    8220

GCTCGAGCTC GACCTGGTCG ACGGCGGCGA AGATCTGCAG AATATTCCGC TCAACCCGCT    8280

CACCCAACCC GTGCGCGCCG TCGACGTCAT CTTCGCTGTC GACTCGTCCG CCGACGTGAC    8340

AAACTGGCCC AATGGCACCG CCCTGCGCGC CACCTACGAG CGCACTTTCG GCTCTATTTC    8400

CAACGGGACA CTCTTCCCCT CGATCCCCGA CGACTGGACG TTTATAAACC TAGGCCTCAA    8460

CAACCGCCCC TCTTTCTTCG GCTGCGATGT TAAGAACTTT ACCTTGAACG CCAACCAAAA    8520

GGTTCCCCCC TTAATCGTCT ATGTCCCCAA CGCGCCCTAT ACCGCGCTGA GCAACGTGTC    8580

CACCTTCGAT CCGTCATACA CGATGTCTCA GCGCAACGAC ATCATCGGCA ACGGATGGAA    8640

CTCAGCCACG CAGGGAAACG GCACGCTGGA TTCGGAGTGG CCCACTTGCG TCGCCTGCGC    8700

GGTTATCAGC AGGAGCTTAG ATCGGTTGGG CAGGCAGACG CCAGCCGCGT GCAAGACTTG    8760

CTTTGACAGG TATTGCTGGA ATGGCACAGT GAACTCCAAA GATACGGGGG TTTACATGCC    8820

TGAGTTCAAG ATTGCGGATG CGCATGCCCT GGACTCGGGT GCTGTTGCTA TCGGAAAGAT    8880

GGTGAATGTC TGGTCGTCGG TTGTGGTGGG AGTTGTGGCG GCTACTTTGT TGTTGTAGGG    8940

GTAGGGGAGA CGTGATGATA TTCCAGTCTG ATGAAGTTGA GACTGGACTG GAGATCGCCA    9000

AGGATGCGGA GGGAAAGGAA TGCGTGGTGT TAATGTCATG ATGGATGAAG AGTCATGGAT    9060

CATGGAACGA CGGGGCGGGG ATATTGGATG ATGGATATAC CACACTGCAT GCATGCTCTA    9120

TTGATAGTAT GCTTTGGCAT TTACGTTTAA CAATCAATTG CTCCATCCTG ATGTTCTATC    9180

TTTTTCGACA ATGGATTGAT ACTACTCCTG TTGCTTCGCT CTTGAGGTTG GAAGGACTTG    9240

AGGTTGGAAG GACTTGAGGT TGTTTGTTCT GAGGGAGGTT ATCGAAGTAT CATCTGTGCT    9300

GATGCCGATT GATAGACTGT CCTCTTCTTC GAGGCAACGA ACGGTCGGAT GAGCCTCTTT    9360

AATCATGATG CTCAGTGCCA CAAAAAGGCT CCAGCACAGC TGCCCACACC TTTCTTGCCT    9420
```

```
CGCCGTTCCT TCCTTTTTCT TTTCCCCTGT TTCCTTTCTT CCTTTCCATC TCATCCCGTA      9480

CCAGAGTGCC CACCGGGTAT ATATATTACC TCCTTGGCCG TTCTCCTTTG ACCAATAAAT      9540

CGCTTGGTCG AGTGGCGTAA CGGTTTACCG TCTACACTTA TCACTCAAAC CAAACCAAAC      9600

CATCGAAGAA GTGACCTATC GGTTCGAGGG AACGGTGATG TTCTTACGAC CAAGTTAACC      9660

CAAAGAGCGT TCCACATCGT TGAACCGTCT CCTCCAGTTG GATCTGTTTA ACTTCCGCAG      9720

CGACTGAAGA AGGTATCACT TTTTTTTTGG TTCCAAAAAA AAAAAAAAAA ATTAC           9775
```

(2) INFORMATION FOR SEQ ID NO:2:

(i) SEQUENCE CHARACTERISTICS:
        (A) LENGTH: 9934 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:2:

```
ACCGGGAATC GTAGCGGGCG CTAAGGCCAA GCCGCGGCAC GGGTCACTGA CCCAATGCAG        60

CGCATTCCGT CAGCAACTGA AGTGGATGTA CAAGTACATA GTAGTAGATC GCAACTGGAG       120

ATCACTCGCA CCGTGCCGCA GAACAAGGGC GACGAGCCTC AGGGCAGTTT AGCCTGCCGT       180

AACAGCACAG ACCATAGCTT ATTTTCACCT GGGCGGGCGG GCGACGGCGG CACTGACATC       240

GGCAAGGCGG CATCAAGCAA CCCCTCTGTT GCTTGCCAGC TGCCGGCCAA CGTCAGCGGT       300

ACAAGGAGAA ATCTGGAAGG AAAGACTTCT GGCACCGACA GGATGGCACG CGGGAAAAGT       360

TCCCAATGCA TGAGATGAGG GGCATTTGCA TTGCCTCCCG TCACCCAGTG CGAACCCCAA       420

CCCCACCATA GCGTCTGTCG ATACATGGAG CGCGAAGTCG AGAAACCTGT AATTCCTGGT       480

AACTTTCAGG TACACAGTAC GTACTGATCC TGGTATCAAA CCTTGCCTGC CGAGTTTTCG       540

ACGGAAAGAG GTGTGAATTG TGAAAGAGTC ATACCAAATC ACCCGATTTT CATAAAGCCC       600

GAGTCTTTTC TGTACATAAG CGACACTCGA AGCGGGCCTC ATCTTCATAG CCTGATAGCT       660

TGTAATACTC CATCCTCGTA TCTCACTTGA CCTTGAGTTC AACCCCACGT CAAACTTCAC       720

CCGACACATC GACGGATTGG GGAACAGCAC AATACCTGAA AAGCGAGAAA ACCAAACAGA       780

GGAAAACACC ATGGAGACAA CACTTCCCCT CCCCTTCCTC GTCGGTGTCA GTGTTCCTCC       840

CGGACTGAAT GACATCAAGG AGGGCCTCAG CCGGGAGGAA GTCTCGTGTC TTGGCTGCGT       900

CTTCTTCGAG GTCAAGCCCC AGACCCTTGA GAAAATCCTG CGATTCCTCA AGCGTCACAA       960

TGTCGAATTT GAGCCCTACT TCGATGTAAC AGCCCTCGAG TCTATCGATG ATATTATCAC      1020

TCTTCTGGAC GCCGGCGCCC GCAAGGTGTT TGTCAAGACC GAGCAGTTGG CCGACCTCTC      1080

CGCATATGGC TCCCGCGTTG CCCCCATTGT CACTGGAAGC AGCGCTGCTT TGCTTTCCTC      1140

CGCCACCGAG AGCGGCCTTT TGCTCTCCGG CTTCGATCAG ACTGCCTCCG AGGCTGCACA      1200

GTTTCTGGAG GAGGCCAGAG ACAAGAAAAT TACCCCCTTC TTCATCAAGC CGTTCCTGG       1260

GGCCGATCTC GAACAGTTCA TCCAGGTCGC CGCCAAGGCT AACGCCATCC CCATCCTGCC      1320

ATCCACTGGC TTGACAACAA AGAAGGACGA GGCCGGCAAG CTTGCCATCT CCACCATCCT      1380

CTCGAGCGTC TGGAAGTCTG ACCGTCCCGA TGGTCTTCTC CCCACCGTTG TCGTTGATGA      1440

GCACGACACT GCTCTGGGTC TGGTCTACAG CAGTGCCGAG AGTGTGAACG AGGCCCTCAG      1500

GACACAGACT GGTGTCTATC AGAGCCGGAA GCGCGGTCTC TGGTACAAGG GTGCTACTTC      1560

CGGAGACACT CAGGAGCTCG TCCGCATCTC GCTTGACTGC GATAACGATG CTCTCAAGTT      1620
```

-continued

```
TGTCGTGAAG CAGAAGGGTC GTTTCTGCCA CCTCGATCAG TCCGGCTGCT TTGGTCAGCT    1680
CAAAGGCCTT CCCAAGCTCG AGCAGACTTT GATTTCGAGG AAACAGTCTG CCCCCGAGGG    1740
CTCCTACACT GCCCGTCTCT TCTCCGATGA GAAGCTAGTC CGGGCCAAGA TCATGGAGGA    1800
GGCTGAGGAG CTCTGCACCG CTCAGACCCC CCAGGAAATC GCCTTTGAGG CTGCCGATCT    1860
CTTCTACTTT GCTCTTACCA GGGCCGTTGC TGCCGGCGTT ACTCTTGCCG ATATCGAAAG    1920
GAGCCTTGAC GCCAAGAGCT GGAAGGTCAA GCGCAGGACT GGAGATGCTA AGGGTAAGTG    1980
GGCTGAGAAG GAGGGCATCA AGCCTGCGGC GTCCGCTCTC GCTGCCACTT CGGCCCCTGT    2040
CACCAAGGAG GCCGCCCAGG AGACCACCCC TGAGAAGATC ACCATGAGAC GTTTCGACGC    2100
CTCCAAGGTC TCTACCGAGG AGCTCGATGC TGCTCTCAAG CGTCCTGCGC AAAAGTCGTC    2160
CGATGCCATC TACAAGATCA TTGTCCCCAT CATCGAGGAC GTCCGCAAGA ACGGCGACAA    2220
GGCTGTTCTG TCGTACACTC ACAAGTTCGA GAAGGCTACC TCTCTTACTA GCCCCGTCCT    2280
GAAGGCGCCC TTCCCCAAGG AGCTTATGCA GCTCCCTGAG GAGACCATTG CTGCCATCGA    2340
CGTGTCCTTC GAGAACATCC GCAAGTTCCA CGCCGCCCAG AAGGAGGAGA AGCCCCTCCA    2400
GGTCGAGACC ATGCCCGGTG TTGTCTGCAG CCGTTTCTCT CGTCCCATCG AGGCCGTCGG    2460
CTGCTACATC CCCGGCGGTA CCGCCGTTCT CCCCAGCACT GCCCTTATGC TGGGTGTTCC    2520
CGCCATGGTC GCCGGCTGCA ACAAGATTGT GTTCGCCTCT CCTCCCCGCG CCGACGGAAC    2580
CATCACTCCC GAGATTGTCC ACGTCGCTCA CAAGGTTGGG GCCGAGTCCA TCGTGCTTGC    2640
CGGCGGTGCC CAGGCCGTAG CTGCCATGGC CTACGGCACC GAGAGCATCA CCAAGGTCGA    2700
CAAGATTCTC GGCCCCGGTA ACCAGTTCGT CACTGCTGCC AAGATGTTCG TCAGCAACGA    2760
CACCAACGCT GCCGTTGGTA TTGACATGCC CGCTGGCCCG TCCGAGGTGC TGGTCATCGC    2820
TGACAAGGAC GCCAACCCCG CGTTCGTTGC CTCGGATCTC CTGTCCCAGG CTGAGCACGG    2880
CGTTGACAGT CAGGTCATCC TGATCGCTAT TGACCTCGAC GAGGAGCATC TTCAGGCTAT    2940
TGAGGACGAG GTTCACCGTC AGGCTACGGA GCTTCCTCGC GTCCAGATTG TCCGTGGCTC    3000
CATCGCCCAC TCGATCACCG TGCAGGTCAA GACCGTCGAG GAGGCCATGG AGCTCAGCAA    3060
CAAGTACGCT CCTGAGCACT TGATCCTCCA GATCAAGGAG GCCGAGAAGG CTGTCGATCT    3120
TGTCATGAAC GCCGGTAGTG TCTTCATTGG CGCCTGGACT CCTGAGTCCG TTGGCGATTA    3180
CTCTGCTGGT GTTAACCACT CGCTGCGTAA GTTACATATC ATAAATAGCC CCGCTTCACA    3240
GATTCTTCTG CTAACGTCAA GACACATAGC TACCTATGGC TTTGGCAAGC AGTACTCTGG    3300
CGTCAATTTC GCCTCGTTCG TCAAGCACAT TACCAGCTCC AACTTGACTG CCGAGGGTCT    3360
CAAAAACGTC GGCCAGGCTG TCATGCAGTT GGCTAAGGTT GAGGAGCTCG AGGCTCACAG    3420
AAGGGCGGTC AGCATCCGTC TTGAGCACAT GAGCAAGAGC AACTAAACGG AAATTCTTTT    3480
CGAAGTAGCA AAAAAAAAA AAAAAACAA GAACAAAAGG ATGTAGTGGG TTGATGTATA    3540
TCTGGGTCAT TTTGGGCACA TAGAGTAATG ATAACGAGTT TTGGACATTG TACTGTTCTG    3600
TACAGGCTGA AGATCAGTAC ATGAATCTGT TGGTAAGTGT GGAGACCCAA ACGTCCCTTG    3660
AGTTTTCTC CCTATTCCAG AGGTGCTCGT CCCTGGGTGT TTATTTTCAT TATTACATCA    3720
ACCTTTTTTT TTTTTTTTT TTTTTCAGAT CATGCGTACA TGAACGGGGG AAGCACAGAC    3780
GATCGAAACG TGGATGTCAC AATGTCGCTG CAGTGATGCT GCATTGCATG AAGCGCCCAT    3840
CTCAATATAC TTGCAGTCTT GCACGTTGCA TGTGAACTTC CCAAACAACC GAATAAAAGA    3900
CGGCGAAAAA TGAAGATAAA AAAAAACCAT AAAAAAAATC AGAGGGAGTG TGGGAAATGG    3960
```

-continued

```
TGTCTTTTAG CATTCAGACC CCATAGCCGT GCACGCCCGG GTACAGACAG GTTCATCGAT    4020
GTTGACATTG ACTGGGACAC CAGGTCTATC TATTTTATCT CCTGTCCTCT ACCATACATC    4080
GGGACATCGG ACATCTTGCT GTACCCCCCA CACCCACAAA GCCTTATAAA AGCGCCACAC    4140
CCGAGGAGGT TCGGTCGGCC CCACGAACTC TGTGCCTCCC TGCCTGTTTA CAGGGACCGA    4200
ACGCTGGAGA ATCTTACTAG TTTCCTGACA TCCGGCCTAC CCGAGCAGGA AAAGGGACAG    4260
CTCATAGGCG AGGAGGGATT TGAAGATGGG AACATTTTGG GTGATTCGAG AGGAGGAACT    4320
AGGTACTGCA TCATGATAGT TCGGGGCAGC ATCTTGGCTG GACATTGTT AATACCTCGA     4380
TATGATGAAG TAGGAGGGAG TTTTTGCGTG TCTTGCCGAA GTCCAGAGAT CTGTTTTATT    4440
TTATTTTTTA TGGATGTAGT GTATCAACAC CCAAGATTCG GAGAATAGTA CTAGGATTCG    4500
CATTTACAAG TGGAAGTCTT GAGAATCGTT GTATATCCTT GTCTTCCTCG GAATGTTAAC    4560
AATCCTACAG CGAGCGAGCG AGCGGTCGGA TGCGCTGATC TGATAGGCGC AATATACGGC    4620
CGCTTTCTCC GGTCGTGTAG TGTAAGCTCT GTGGGCATAG TACACTAAAA AAACCCTTGC    4680
ATTTCATGAT CTGCCTGCTA TTCATTCCGA GCTATTTCAG TGGTCACATT TCGAGGAAGA    4740
AAGAAAGCAA CTAAGATTCA CAGCCATCCA TCCATCCATA TGGAAGAATA ATCCATTCCC    4800
ATGTTCCCTC CCCCCCACTA TGTATGTGAC CACACGCTGC TGTCAGAATG CCAACGGTCT    4860
CAGGTACCCT CGTCCGACTG TTTGGCATGG AGTTACATAC ACTACTAGTG TAGCCCCGGG    4920
CCAAGCTACC CCGTCAAATC TATACATATC TATAACGGGT TTCAGGGGTT TCGTTCGCTG    4980
TCAATCAAGT TTGAAACATC ACTGGGGCCG TTGGACGGTG TATTAGACCA TTGGCTCCCT    5040
CAGCTGTTTG GCGGCTGGGC GGCTGGGTCA AACGGCAATA ACGGGACTCG AGAGGGACGA    5100
GGAGAGTCGG TTGGCTGGCT GCAATACAAG CGTTCCCACC TAACCAACGA GTCCCGTTTT    5160
CCATTTGTGT GCCTAACCAT CATCTAGGGA TGTCAGGGTT TGGCCGGATC AGGGTATGTT    5220
TGGTTGACTG TTGTCATGTC TGATTGGGTA CATATTATGG TAGGTGTCTC GAGAACAGTA    5280
GAGTACTCGG GCCTAGCGTT TGGATGATTA CGCGAGATAT GAGTTGTGGG CCGCCATGCA    5340
GTTGCTTGTC CATAAGCAGA AGTTGCTTTG GGATATATTT CTCGTCTTTC AAAGGTCACG    5400
AGGTCCTGGG ACGAACGGCA TCGCCATCCA AAGGGTTGAA CATGAGAAAC CTGAATGGCC    5460
TTTGCGTTGA AATACAAAAA GTCAAGAACA AAATCGCTTG AGGATAGGGA CGTGGAAGCA    5520
AGCAAATATG GTAAGAGAGG TATACATCAA CCCTGGTTCA ATTGTTAGCG TGGTTCTTCC    5580
TCCACGTCCT CGTTCATGAC GGTTAACAGT ACCAGGCTAA CAATTAAACC AGGGTTGATG    5640
TGTACTGATA TGTAGGTGCT CAGCAAACTG CCAATTTCTT TGGCCCCAAG CAGCAGTTTG    5700
CTGTCAGTGC TGCTCGTGTC AGCCTTGGTA GTGGAACCTA AACTGCTAAC ACAGCGCAAG    5760
TGCGCATGTA AAGATATTGT GGGAGGATCT GTATGGATGG ATGAGATTAC TGCTTGGTGT    5820
TGGTTGCGAG GCACTGCGGC TGTTAGGCTT TGCTGTGCCC CGTTCGACGA AGAAATACGC    5880
GGAACTATAA ATTGGATACC TAGACTTACT GCCTATGGGA GGTATCTACC GACGTAGCCG    5940
ACGGATTCTA GCAACATCCC GACTTTGCTT GTAGTGTACT ATGATAGCAG CACAGTGTTG    6000
CTCCTTGTGA GAATGGGCTC TTTTTTTTTT TCCCCCTTCC CTAGGGCGTT GACTGGACTT    6060
GCTCTATTGT TCCAAGGTA GGTGCCCGTC ATCGATTTTC CCAAGTCTCC CGCCAGATTG     6120
TCGTCATAGT GTCATGATGA CCTCGGTCGC TGGGGCTGCG TGGTTACGGG GAGCTGGGAC    6180
CGCTAGGCCT CAGTGGTTGT GCCATTCAGC GTGGGTGTGT GGAGTAGCGG TAGAGGCGCT    6240
TGGAAGTTGT GCTAGCGGAA ACCCTGGAAT ATCTTCTACC CTCGATTCCT TCTCGGGCTG    6300
CCCATGTGCT GAGGTGATGC CGGGGATCTG GCGCCAATCA TCCATTGAGG TTCCCGCAGC    6360
```

```
TTCCCGGTGC CGCGCGCGGG CGCAGTTGCT CACAGGACAC ACCTAGACGC AGGGGCACAG      6420

GGGCACCGTT TGGTGTGCAA CTGGGTACCT AGCTGTAGCA AGCACTCCAC CGTCTGTGCA      6480

ATCCCCCAAT CCACGGCAGG AACTTCGCAC CGCCGCGGCA CCGAGTGAGC GAATCCATCC      6540

GCATTGGATC CCAATTCTTG CCCTTGCCAT CCTTCTTTCT TCCCACTTGG CGCAACCAAC      6600

ACTTCCCTTG GTCTGGGTAC TCGTGTTGAT CTTCACTCTC TTTTTTTCTT GGGCGACCGA      6660

CTTTTTATAT CCGTCCTTGC TTCCCCCTGG CCGTTGTCGT TCTTTCTACA ACTACCTTCC      6720

GTTCATTATC CCCTTTCTTG GTTCGGTCGA GGACCCAAAA ACAGAACAAT TCCGGCTCTT      6780

CCAGGTGGCT TGGGTGCGAC TGTTTAGCTC TTGACCACTA GCCGCTTACC TTCTCTTGAT      6840

GTTTTTATTT GGATATCATT AAACTACTCT TTCTTGAAAC GGCAGACGAA CGGAACAGTT      6900

CCTACGGTAT ATTAGCGATA TACGTTGTAC TGATATTCTG AGCAAGAAGA GGCAAATTAT      6960

CAATTATGCA TCTCCCTTCG TCGCTGCTCA TCGCAGCTCC CTTGCTCGCC AATGTATCGG      7020

CCGAACCCAT TAGGATACCC CAACGCGATG TTCTCCGTGG TATCAACATC ACAGCAACTT      7080

GCCGTTCGAG CACTACCGGA TTCGCCCAGC GGTGGATATG CCCCTGCCGT TGTAGACTGT      7140

CCCAAGACCA AGCCGACGCT CCGGAAGGCC GTGGATTTGT CGAACGAGGA GAAGAACTGG      7200

TTGTCGATCC GGAGGAAGAA CACCATCCAG CCCATGAGGG ACCTCCTGAA GAGGGCCAAC      7260

ATCACTGGGT TCGATTCCGA GACATTTATG AATGAGGCCG CCAACAACAT CTCGCAACTG      7320

CCCAATGTCG CCATTGCCAT TTCAGGAGGC GGCTATCGTG CCCTCATGAA CGGCGCCGGC      7380

TTCGTTGCTG CTGCGGATAA CCGAATTCAA AATACCACGG GCGCAGGTGG TATTGGAGGC      7440

TTGTTGCAGT CCAGCACATA TTTGTATGTA AAGTGGTTCT TCTTATCTCG TTTTCGAGTG      7500

TCAACTGCGC CAGTTCAGAG TTGGGCGGCT GTGGACGACC TTGCTGGTGA ACATGTCTTG      7560

GACTCCATGC CCCTTCTTCG TTTCCTCAAA TCAAGAAGTC GAGGACCGTG ACCGTAAATC      7620

GCTAACGCAA CTCTAGGGCC GGACTTTCTG GTGGTGGCTG GCTTGTCGGC AGTTTGTTCT      7680

CCAACAACTT CAGCAGCATT GAGACCCTGC TGAGCGAGAA CAAAGTCTGG GACTTTGAGA      7740

ACTCCATCTT TAAAGGGCCC AAGGAGGCTG GCCTTAGTAC TGTCAACCGC ATTCAGTACT      7800

GGTCCGAAGT GGCAAAGGAA GTTGCCAAGA AGAAGGATGC TGGCTTCGAG ACAAGTATAA      7860

CAGACTACTG GGGCCGAGCA TTGAGTTACC AACTGATCGG AGCCGATATG GGCGGCCCGG      7920

CTTACACCTT CTCCAGCATT GCCCAGACCG ACAACTTCCA GAAGGCCGAA ACGCCGTTCC      7980

CTATTCTGGT AGCTGACGGC CGCGCGCCTG GAGACACCAT CATCTCCCTC AATGCTACCA      8040

ACTACGAGTT CAACCCGTTC GAGACGGGTA GCTGGGACCC GACCGTCTAT GGCTTTGCGC      8100

CGACCAAGTA CCTCGGCGCC AACTTCAGCA ACGGCGTGAT CCCATCGGGA GGCAAGTGCG      8160

TTGAGGGTCT CGACCAAGCC GGCTTCGTCA TGGGCACCAG CAGCACGCTC TTCAACCAGT      8220

TCCTTTTGGC CAACATCTCC AGCTACGACG GTGTTGCCCG ACGTGCTCAT CGAAGCCGTG      8280

ACTTCTGTCC TCAAGGAAAT CGGCGCCAAG AGGACGACGT CTCCCAAATC ATCCCTAATC      8340

CGTTCCTGGA CTGGAACAAC CGGACCAACC CCAACGCCGA CACGCTCGAG CTCGACCTGG      8400

TCGACGGCGG CGAAGATCTG CAGAATATTC CGCTCAACCC GCTCACCCAA CCCGTGCGCG      8460

CCGTGGACGT CATCTTCGCT GTCGACTCGT CCGCCGACGT GACAAACTGG CCCAATGGCA      8520

CCGCCCTGCG AGCCACCTAC GAGCGCACTT TCGGCTCTAT TTCCAACGGG ACACTCTTCC      8580

CCTCGATCCC CGACGACTGG ACGTTTATAA ACCTAGGCCT CAACAACCGC CCCTCTTTCT      8640

TCGGCTGCGA TGTTAAGAAC TTTACCTTGA ACGCCAACCA AAAGGTTCCC CCCTTAATCG      8700
```

-continued

```
TCTATGTCCC CAACGCGCCC TATACCGCGC TGAGCAACGT GTCCACCTTC GATCCGTCAT    8760

ACACCATGTC TCAGCGCAAC GACATCATCG GCAACGGATG GAACTCAGCC ACGCAGGGAA    8820

ACGGCACGCT GGATTCGGAG TGGCCCACTT GCGTCGCCTG CGCGGTTATC AGCAGGAGCT    8880

TAGATCGGTT GGGCAGGCAG ACGCCAGCCG CGTGCAAGAC TTGCTTTGAG AGGTATTGCT    8940

GGAATGGCAC AGTGAACTCA AAAGATACAG GGGTTTACAT GCCTGAGTTC AAGATTGCGG    9000

ATGCGCATGC CCTGGACTCG GGTGCTGTTG CTATCGGAAA GATGGTGAAT GTCTGGTCGT    9060

CGGTTGTGGT GGGAGTTGTG GCGGCTACTT TGTTGTTGTA GGGGTAGGGG AGACGTGATG    9120

ATATTCCAGT CTGATGAAGT TGAGACTGGA CTGGAGATCG CCAAGGATGC GGAGGGAAAG    9180

GAATGCGTGG TGTTAATGTC ATGATGGATG AAGGGTCATG GATCATGGAA CGACGGGGCG    9240

GGGATATTGG ATGATGGATA TACCACACTG CATGCATGCT CTATTGATAA TATGCTTTGG    9300

CATTTACGTT TAACAATCAA TTGCTCCATC CTGATGTTCT ATCTTTCGAC ACTGGATTGA    9360

TACTACTCCT GTTGCTTCCC TCTTGAAGTT GGAAGGACTT GAGGTTGGAA GGACTTGAGG    9420

TTGTTTGTTC TGAGGGAGGT TATCGAAGTA TCATCTGTGC TGATGCCGAT CGATAGACTG    9480

CCCTCTTCTT CGAGGCAACG AACGGTCGGA TGAGCCTCTA ATCATGATGC TCAGTGCCAC    9540

AAAAAGGCTC CAGCACAGCT GCCCACACCT TTTTTGCCTC GTCGCTCCTT CCTTTTTTTC    9600

CCCCCCTTTC TTCCTTTCCA TCTCATCCCG TACCAGAGTG CCCACCGGGT ATATATATTA    9660

CCTCCTTGGC CGTTCTCCTT TGACCAATAA ATCGCTTGGT CGAGTGGCGT AACCGTTTAC    9720

CGTCTACACT TATCACTCAA ACCAAACCAA ACCATCGAAG AAGTTACCTA TCGGTTCGAG    9780

GGAACGGTGA TGTTCTTACG TTCAAGTTAA CCCAAAGAGC GTTCCACATC GTTGAACCGT    9840

CTCCTCCAGT TCTTGGATCT GTTTAACTTC CGCAGCGACT GAAGAAGTAA TCACTTTTTT    9900

TTTTTTTGGT TCCAAAAAAA AAAAAAAAAA TTAC                                9934
```

REAGENTS AND METHODS FOR DIVERSIFICATION OF DNA

FIELD OF THE INVENTION

The present invention relates to the field of molecular biology and a method and reagents for the diversification of DNA sequences. The present invention allows the generation of variant DNA sequences, which can provide variants of sequences that regulate gene expression, code for proteins, control the export of gene products from cells and the localization of gene products within cells. In particular, the present invention provides a method and reagents for efficiently generating new variant sequences in heterologous DNA (DNA foreign to the cell) by placing two sequences, that differ at multiple sites, into the same cell at a location that permits the expression of the new variant sequence after diversification and which provides for the generation of new variants as a result of the exchange of parts of the two sequences within the living cell.

BACKGROUND OF THE INVENTION

Diversification of DNA molecules provides a way to generate new proteins with properties not found in nature. This can be achieved in vitro (by manipulation outside living cells) by a variety of methods such as the insertion of specific novel and random sequence oligonucleotides (Gold, L et al 1997 Proceedings of the National Academy of Science, 94:59–97) in selected regions of genes, or the cleavage of variant DNA molecules (two sequences that have similar functions but differ in one or more sites) and reassembly of the fragments in new combinations (Stemmer, WPC 1994 Proceedings of the National Academy of Science, 91: 10747–10751), or by amplification of DNA by the polymerase chain reaction under conditions where the polymerase is error prone (Leung, D W et al 1989 Technique 1: 11–15). Screening for desired properties of any protein coded by the resultant novel nucleotide sequence requires transcription and translation of the sequence to yield the corresponding peptide and the appropriate post-translational modification. In these cases, this is usually achieved by introducing each new construct into a cell by transfection or electroporation (hereafter both processes will be covered by the term transfection) to form a transformed cell, a complex and time consuming procedure since it is necessary to check each construct to ensure it is correctly inserted and is complete. This difficulty is compounded where the new construct codes for one component of a multimeric protein since the procedure must be done twice for each new combination. That problem can be reduced by the use of fungal heterokaryons to lower the number of transfections required to one per component of a combinatorial array (U.S. Pat. No. 5,643,745, to Stuart, issued Jul. 1, 1997). However, the number of transfections required is still large and each must be checked to ensure the DNA insert is correctly placed and complete.

Genetic recombination

Genetic recombination in eukaryotes, higher organisms that have a true nucleus, occurs during the prophase of the reduction division that converts a diploid cell having two complete sets of homologous chromosomes to a tetrad (or sometimes an octad) of haploid cells each with one complete set of chromosomes. Two manifestations of recombination events are recognized: crossing over in which genes located at different sites (loci) on the same chromosome are recombined by reciprocal exchange of chromosome sections between a pair of homologous chromosomes and gene conversion in which the number of copies of a pair of allelic genes, ie genes that occupy the same locus on homologous chromosomes, is unequal in the tetrad or octad. Instead of a two:two segregation of the parental alleles, the tetrad comprises three haploid cells carrying one of the parental versions of the gene and one carrying the other parental version of the gene. Crossing over was first discovered in the fruit-fly Drosophila (Morgan Proc. Soc. Exp. Biol. Med. 8:17 1910) and gene conversion in the fungus Neurospora (M B Mitchell Proc. Natl. Acad. Sci. USA 41: 216–220 1955). There is now evidence that both crossing over and gene conversion occur universally in species that reproduce sexually and that a process having similar outcomes occurs in bacteria and their viruses and plasmids.

Genetic recombination in eukaryotes occurs in diploid cells (cells that contain two complete sets of homologous chromosomes) that are undergoing meiosis. Prior to the division, each of the two chromosome sets is replicated, generating two pairs of identical sister chromatids. The process of genetic recombination involves the establishment of joints between two homologous but not necessarily identical DNA sequences, one located on one chromatid of one sister pair and the other in a homologous chromatid which is a member of the other sister pair. The joints establish regions in one or both chromatids where one strand of the DNA duplex has the sequence of one homologue and the second strand has the sequence of the other homologue. Where the DNA sequences of the homologues differ, bases will be in mismatched pairs, that is pairs which are not A:T or G:C (A=deoxyadenine, T=deoxythymine, C=deoxycytidine and G=deoxyguanine). Enzymatic machinery corrects mismatched base pairs and the joints between the molecules are resolved, separating the two chromatids once more. For each site of mismatch, in half of the cases, the base pair present in one chromatid is now replaced by the base pair originally present in the other homologous chromatid. This accounts for gene conversion. In some cases the joints between molecules are resolved such that there is a reciprocal exchange of the regions each side of the joint. This process is called crossing over and also leads to novel combinations of DNA sequence information by which the parental homologues differed. Each chromatid is incorporated into one of the haploid cells (cells having only one set of chromosomes) that arise from meiosis, becoming a member of the complete set of chromosomes present in each cell.

The molecular processes of crossing over and gene conversion are yet to be fully understood. In the most widely accepted model for the molecular events of recombination (FIG. 3) (H Sun et al Cell 64: 1155–1161, 1991) it is supposed that one of the two homologous chromatids suffers a break in both strands of the DNA molecule and that the strands that end with a 5' phosphate are resected, leaving a single strand tail of several hundred bases that ends with a 3' hydroxyl group. It is proposed that the single strand tail pairs with the complementary strand of the unbroken chromosome to initiate the joint. The joint is thought to be completed by DNA synthesis from the 3' ends to provide a replacement strand for the DNA lost in the initial resection followed by rejoining of the breaks. This will form a double junction between the molecules in the manner shown in FIG. 3. Each junction is free to move. This leads to strand exchange between the two DNA molecules forming heteroduplex DNA. It is supposed that recombination is completed by scission of the junctions and correction of mispaired bases. Scission of the junctions can occur by breaks in either the "inner" or "outer" strands with equal probability (FIG.

3). Due to the limitations of a two dimensional representation of the junctions, the expectation of an equal frequency of these two modes of scission is not self evident. However in reality, the two pairs of complementary strands, both the inner and outer pair, are identically juxtaposed. If the resolution of both junctions occurs in the inner strands or alternatively in the outer strands, only gene conversion can occur. If the resolution of one junction is by scission of the inner strands and the other junction by scission of the outer strands, the flanking regions are reciprocally exchanged and there is both a crossover event and also the possibility of gene conversion.

There is direct evidence that recombination is initiated by two strand breaks in the yeast *Saccharomyces cereviseae* (A Schwacha and N Kleckner, Cell 83: 1–20 1995). However, the exact series of events by which these are processed to complete a recombination event is not clear. Indeed, Bowring and Catcheside working with the fungus *Neurospora crassa* (Genetics 143: 129–136 1996) have shown that most of the crossing over events previously thought to be associated with gene conversion are several hundred kilobases away, too far to be directly associated, suggesting that gene conversion and crossing over can be catalyzed by different recombination pathways.

Biological processes including recombination are error prone. M K Watters and D R Stadler (Genetics 139, 137–145 1995) examined the spectrum of spontaneous mutations (changes in the sequence of DNA bases in a gene, from that present in wild-type cells, that render it defective) in the mtr gene of *Neurospora crassa*. Watters and Stadler found that the spectrum of mutations which occur during the sexual phase that includes meiosis and recombination is distinct from those that occur during asexual reproduction by normal vegetative growth. Error prone recombination is a source of sequence diversification in vivo additional to that obtainable by the generation of new combinations of multiple sequence differences that distinguish homologous DNA sequences.

Genetic recombination in eukaryotes occurs in diploid cells that contain two complete sets of chromosomes and thus two complete sets of genes. The diploid state is established by the fusion of two haploid cells, usually of different parentage. This can be achieved by the fusion of gametes, as in the fusion of eggs and sperm in humans and other animals or of pollen cells with ovules in plants, or by fusion of two strains in the fungi where ability to fuse is usually controlled by mating type genes that ensure those strains that fuse are of different mating type and thus not genetically identical. In plants and animals, the fusion of haploid gametes establishes a clone of diploid cells which normally develops into an individual adult member of the species where genetic recombination occurs in specialist diploid cells in those parts of adults that give rise either to eggs or sperm. In the fungi, fusion of haploid strains usually gives rise to a dikaryon (a cell having haploid nuclei of two types, each with the genetic composition of one of the two strains, in a common cytoplasm). The dikaryon can form the main phase of the life cycle, as in the macrofungi ("mushrooms" and "toadstools"), or can be transient and give rise to diploid cells, immediately or after a limited number of mitotic cell divisions, that then undergo meiosis.

Genetic recombination in eukaryotes occurs during meiosis, the reduction division in which a diploid nucleus gives rise to four haploid nuclei each having only one set of chromosomes. During this process, the genetic information in the two sets of chromosomes present in the nucleus of the diploid cell is recombined. New gene combinations can be generated by reassortment of chromosomes between the sets present in the two haploid cells that contributed to the diploid cell undergoing meiosis and also by crossing over and gene conversion which generate new combinations of the sequence information present in pairs of homologous chromosomes. In prokaryotes, genetic recombination can occur between DNA sequences present in the chromosome and those carried by plasmids such as the fertility factor F of *Eschericia coli* or bacteriophage such as phage λ (lambda) and between two phage molecules, two plasmids or any combination thereof.

The methods and compositions to cross together two genetically distinct individuals or strains of a living organism in order to obtain individuals with new gene combinations by reassortment, crossing over and gene conversion varies from species to species and for most species is within the common art of the biological sciences. Some species are better characterized genetically than are others, as a result of their being of particular economic importance, particular ecological or aesthetic importance or are species that are particularly favorable for research into the fundamental processes of biology. The best characterized species include the bacterium *Escherichia coli,* the plants *Arabidopsis thaliana* and *Oryza sativa,* the insect *Drosophila melanogaster,* the mammal *Mus musculus,* the nematode *Cenorhabditis elegans,* the slime mould *Dictyostelium discoideum* and the fungi *Saccharomyces cereviseae, Aspergillus nidulans* and *Neurospora crassa.* In each case there are compendia of standard methods for their growth and for conducting crosses. For example for *Neurospora crassa,* these include D D Perkins et al (Microbiol. Rev. 46:426–570 1982) R H Davis and F J deSerres (Methods in Enzymol. 17A: 79–143 1970). The following details of methods and compositions for genetic recombination in the fungi are given as examples and are not intended to limit the application of the invention for in vivo diversification of DNA sequences to these species. Nevertheless, bacteria are in general not suitable for the purpose of diversifying and expressing eukaryote sequences due to the lack of the correct processing pathways for proper gene expression and modification of any protein product. Amongst the eukaryotes, only in the fungi has understanding of the relevant molecular processes reached the level required for practical application of the present invention.

Recombination Hotspots

Crossing over and gene conversion during meiosis do not occur at random positions within chromosomes. Recombination is particularly frequent in regions called recombination hotspots. Recombination hotspots are also called recombinators. Recombination hotspots typically occur at several locations on a chromosome, frequently, but not always being in the regulatory region 5' of the coding sequence of a gene. They have been directly demonstrated in several species including the yeasts, *Schizosaccharomyces pombe* at the ade6 gene and *Saccharomyces cerevisiae* at the arg4 and his4 loci (M Lichten and A S H Goldman Ann. Rev. Genet. 29: 423–444 1995) and in the filamentous fungi in the Ascomycete *N. crassa* at cog (D G Catcheside & T Angel Aust. J. Biol. Sci 27: 219–229 1974) and at the am and his-3 loci and in the Basidiomycete *Schizophilum commune* (G Simchen and J Stamberg Heredity 24: 369–381 1969) at mating type loci . Recombination hotspots that have been studied include the arg4 and his4 hotspots in yeast. The ability of yeast recombinators to diversify heterologous DNA has not been demonstrated, and further, unlike cog and other recombinators in Neurospora, the yeast recombinators have not been shown to be regulated.

There is indirect evidence that recombination hotspots are widely distributed in higher eukaryotes including *Homo*

*sapiens* (K F Lindahi Trends. Genet. 7: 273–276 1991) and plants including *Zea mays* (L Civardi et al Proc. Nat. Acad. Sci. USA 91: 8268–8272 1994). Recombination hotspots in bacteria include χ (chi) (R S Myers and F W Stahl, Ann. Rev. Genet. 28: 49–70 1995) which stimulates recombination between any pair of bacterial chromosomes, phages or plasmids and site specific recombinators such as att which stimulate insertion and excision of phage such as phage λ (lambda).

In the case of the filamentous fungi, it is known that at least some of the recombination hotspots are subject to regulatory genes that turn them off. The genetic systems that regulate hotspot activity are well known only in Neurospora where the genes rec-1, rec-2 and rec-3 each turn off a different subset of hotspots scattered in the *Neurospora* genome. rec-1 blocks recombination at the nit-2 and his-1 loci. rec-2 blocks recombination at the his-3 locus and also in the chromosomal regions between the his-3 and ad-3, arg-3 and sn and pyr-3 and his-5 loci. rec-3 blocks recombination at the am and his-2 loci. Control of recombination by rec genes in *N. crassa* has been reviewed by DEA Catcheside (Genetical Research, 47: 157–165 1986).

There remains a need for an effective reagents for and methods employing the process of recombination and recombination hot spots to introduce sequence variation into, to diversify, heterologous DNA.

SUMMARY OF THE INVENTION

The present invention relates to fungal cells, reagents, methods, and the like for diversification of DNA. Preferably the DNA to be diversified is heterologous DNA introduced into a plasmid and/or a fungal cell. The fungal cell of the invention can be either a diploid or a haploid fungal cell having a recombinant genome. A haploid fungal cell of the invention includes heterologous DNA functionally coupled to a recombination hot spot or recombinator. The haploid cell can be converted to a diploid cell, and the heterologous DNA can undergo recombination in the diploid cell. A diploid fungal cell of the invention includes a first and second heterologous DNA, each of which is functionally coupled to a first and second recombination hot spot, respectively. The first and second heterologous DNA can recombine.

A plasmid of the invention is suitable for replication of heterologous DNA in a fungal cell. A preferred plasmid includes a truncated *N. crassa* his-3 gene and a *N. crassa* recombination hot spot, both of which are functionally coupled to a heterologous DNA. A preferred plasmid also includes a multiple cloning site 3' to the his-3 gene and a marker gene. Advantageously, the plasmid can transfect an *N. crassa* cell. The plasmid can be incorporated in a fungal cell.

Diversified DNA can be prepared by using one or more of a plasmid of the invention or a fungal cell of the invention in a method of the invention. The method of the invention provides for introducing heterologous DNA into a fungal cell for recombination, crossing over, and/or conversion. This results in diversification of the heterologous DNA. A preferred method includes the steps of constructing strains of a fungus including heterologous DNA to be diversified with each heterologous DNA coupled to a corresponding recombination hot spot. This preferred method includes mating the strains to form a dikaryon, establishing a diploid cell line from the dikaryon, and inducing meiosis. Advantageously, meiosis includes one or more of gene conversion, crossing over, errors in recombination. This results in diversifying the heterologous DNA. The invention also includes a kit for carrying out the method.

A strain of fungus, preferably a strain useful for producing diversified DNA, can be formed by another method of the invention. This method requires making a diploid fungal cell containing non-complementary alleles of a gene providing an auxotrophic mutation, which gene is functionally coupled to, adjacent to, or juxtaposed to the heterologous DNA to be diversified. This diploid allows enrichment for cells containing diversified DNA. Preferably, a first fungal cell having a first allele of the gene providing an auxotrophic mutation is transfected with a plasmid including a first heterologous DNA and a second allele of the gene providing an auxotrophic mutation. Advantageously, each of the first and second alleles encode a defective gene but are complementary alleles. The presence of the first and second allele of a gene following transfection of the first fungal cell establishes a first heterokaryon, which is grown to provide a first homokaryon containing the second allele of the gene and the first heterologous DNA.

Preferably, a second fungal cell having a third allele of the gene providing an auxotrophic mutation is transfected with a plasmid including a second heterologous DNA and a fourth allele of the gene providing an auxotrophic mutation. Advantageously, each of the third and fourth alleles encode a defective gene but are complementary alleles. The presence of the third and fourth allele of the gene providing an auxotrophic mutation following transfection of the second fungal cell establishes a second heterokaryon, which is grown to provide a second homokaryon containing the fourth allele of a gene and the second heterologous DNA. In a preferred embodiment, the first allele and the third allele are the same allele. The desired fungal strain is established by crossing the first and second homokaryons.

BRIEF DESCRIPTION OF THE DRAWINGS

FIGS. 2A–C illustrate methods for diversification of DNA sequences coding subunits of heteropolymeric proteins and testing for variants.

FIG. 3 illustrates a modified double strand break repair model for meiotic recombination.

FIG. 5 illustrates a map of the his-3, cog, lpl region of linkage group 1 of *Neurospora crassa*.

FIG. 6 illustrates discontinuity in the parental origin of DNA sequences and progeny from crosses between pairs of his-3 alleles.

FIG. 7 illustrates the nucleotide sequence of the his-3 $cog^L$ lpl region of linkage group 1 of the Lindegren wild type strain of *Neurospora crassa* (SEQ. ID NO:1).

FIG. 8 shows the nucleotide sequence of the his-3 $cog^E$ lpl region of linkage group 1 of the St Lawrence wild type strain of *Neurospora crassa* (SEQ. ID NO:2).

FIG. 9 illustrates construction of the components of a sequence diversification cross.

FIG. 10 illustrates construction of parent strains for crossing.

FIG. 12 illustrates conversion frequency of am markers. Data are for $am^6$ convertants and were extrapolated to include progeny for which molecular markers were not scored. A' is the conversion frequency of A excluding events associated with discontinuous tracts.

DETAILED DESCRIPTION OF THE INVENTION

Methods for Diversification of DNA

Figure 1A:
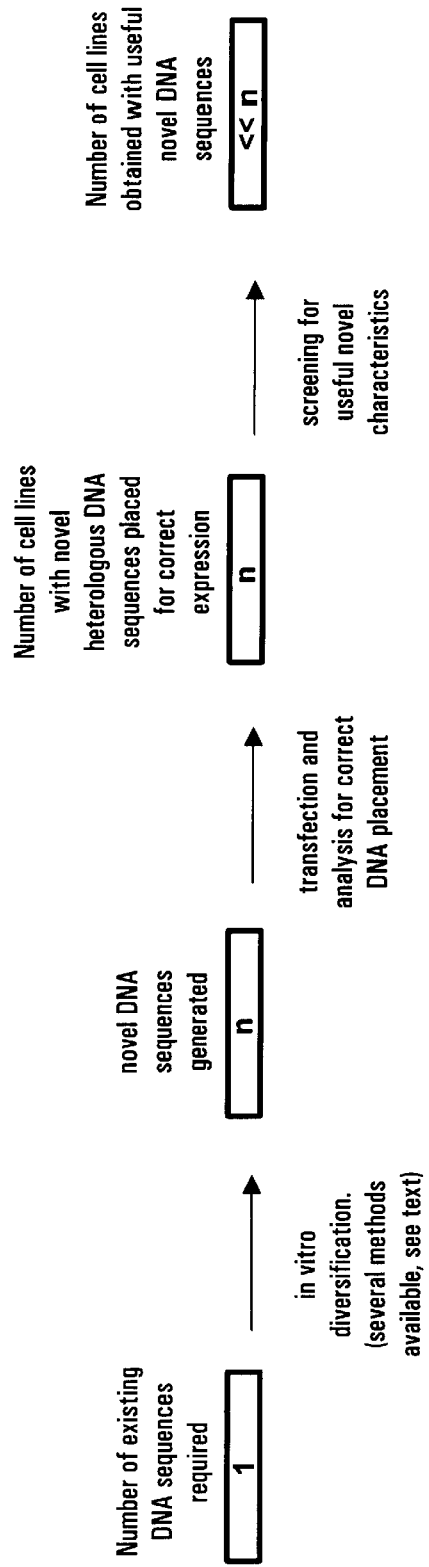
FIGS. 1A–B illustrate methods for diversification of DNA sequences and testing for variants.

This invention provides a means to diversify heterologous DNA sequences in vivo to yield strains able to stably express the diversified genes directly. As used herein diversification refers to introducing sequence variation or new sequences into a DNA molecule or segment using the processes of recombination, crossing over, and/or conversion. In a preferred embodiment, the invention employs cog, a particularly active recombination hotspot in *N. crassa*, which generates discontinuous conversion tracts at high frequency. In consequence, nearby sites of sequence mismatch in the parent molecules are often not co-converted (see FIG. 6) and the sequence of bases in the DNA of their progeny often has a new combination of the sequence differences that distinguished the parent molecules. The high frequency of discontinuous conversion tracts allow relatively infrequent events to be selected as a source of new variant sequences.

Diversified sequences are generated by constructing two interfertile (fertile) strains, parent (variant 1) and parent (variant 2), each having a different version of the gene or other foreign DNA sequence to be diversified juxtaposed to a recombination hotspot. The two strains are mated and the foreign sequences are diversified as a result of gene conversion, crossing over and/or errors in recombination that occur during meiosis as a result of the activity of the recombination hotspot. The foreign or heterologous DNA sequence is functionally coupled to the recombination hot spot. That is, the DNA sequence is in a position subject to recombination, crossing over, and/or conversion in the presence of the recombination hot spot. Where it is advantageous, the high frequency of discontinuous conversion tracts enhances of the yield of recombinants by selecting for progeny that have experienced a recombination event in a gene more distant from the recombinator than the foreign DNA to be diversified, ensuring that the whole of the foreign DNA sequence was covered by a conversion tract.

Where needed for the expression of heteromeric proteins, such as but not limited to immunoglobulins, these strains are also able to be combined in pairwise or other combinations to form a panel of heterokaryons each of which stably express one of the possible combinations of the in vivo diversified foreign sequences.

The present invention provides a method for diversification of heterologous DNA molecules in vivo to generate new sequences that is advantageous and economical compared to previous methods. Diversification in vivo refers to diversification of foreign sequences after they have been introduced into living cells. This method significantly reduces the number of transfections that need to be performed and the number of genetically altered cells that must be checked for proper sequence insertion. The method of the invention generates a panel of different sequence variants, each being correctly integrated in the DNA of the host cell and thus able to be correctly expressed.

Figure 1B:
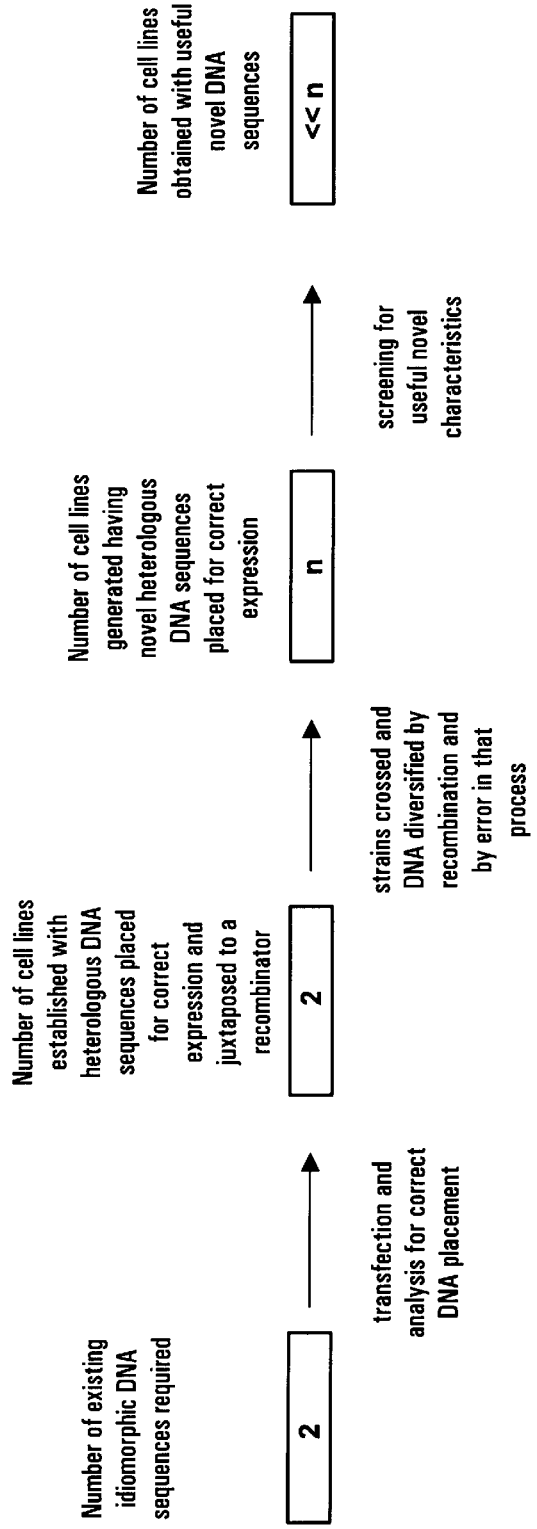

The reduction in the number of transfections required can be dramatic, particularly for monomeric or homomultimeric proteins. For example, if it is desired to generate 1024 new variant genes each coding for a version of a specific protein, in vitro diversification methods require 1024 transfections. Then each of the 1024 resultant transformed cells must be checked for correct insertion of the DNA (FIG. 1A). However, if the 1024 new variants are generated using the present invention, only two transfections are required. This is a dramatic and advantageous reduction, a 512-fold reduction, in both the number of transfections that must be done and the number of transformants that must be checked for correct insertion of the heterologous DNA (FIG. 1B).

The present invention can also yield a dramatic reduction in the number of transfections required for heteromultimeric proteins such as immunoglobulins. For example, new immunoglobulin variants can be generated by diversifying the immunoglobulin heavy chain gene, the immunoglobulin light chain gene, or both, and then combining them in pairwise combinations of a single heavy chain gene and a single light chain gene in a cell line able to express the genes correctly. 1024 new combinations of heavy and light chain genes can be obtained by combining 32 heavy chain variants with 32 light chain variants in all pairwise combinations. To generate the 1024 combinations using in vitro generated variant DNA sequences requires two transfections and checking the transformed cells for correct insertion of both a heavy chain variant and a light chain variant in each of 1024 cells (FIG. 2A). This requires 2048 sets of complex manipulations. This is a large number of complex manipulations.

Compared to in vitro methods, the number of transfections and manipulations can be reduced by using the heterokaryon technology described in U.S. Pat. No. 5,643,745, issued to W. D. Stewart on Jul. 1 1997. The Stewart method combines nuclei from a cell line expressing a heavy chain variant with nuclei from a cell line expressing a light chain variant to form a cell line containing nuclei of both types. In the Stewart method, it is necessary only to establish 32 cell lines carrying heavy chain gene variants and 32 cell lines carrying light chain gene variants to permit fusion of the cell lines into the 1024 different heterokaryotic cell lines having all possible pairwise combinations of one heavy chain gene with one light chain gene (FIG. 2B). That approach requires only 64 transfections and subsequent checking for correct insertion of the variant DNA, a 32-fold reduction in the number of transfections and construct checking required, compared to previous in vitro methods.

The present invention provides a further sixteen fold reduction in the number of transfections that need to be done and constructs that need to be checked for correct insertion of the DNA compared to the Stewart method. The present invention requires only four transfections and only four constructs need to be checked for insertion to generate 32 new variants of light chain genes and 32 new variants of heavy chain genes required to test 1024 combinations (FIG. 2C).

The larger the panel of variants to be tested, the greater the advantage of the present invention for in vivo diversification of DNA sequences. The limitation of new combinations that can be generated by the present invention is determined by the number of sequence differences between the DNA sequences recombined. It is known that 3.5% sequence difference over 3,000 bp is tolerated by the recombination mechanism. This is sufficient to generate about $10^{166}$ new variants from a single pair of sequences by recombination alone and an indeterminate large number more if errors occur in the recombination event. By using additional pairs of homologous DNA sequences (DNA sequences having substantial similarity but differing in one or more positions), an essentially unlimited variety of new sequence variants can efficiently be generated.

Conducting and Measuring Genetic Recombination Employing Fungi

The principal phase of the life cycle of fungi is haploid, making them advantageous for the study of recombination and for the generation of new genes or DNA sequences by the process of recombination or by errors in that process. Many fungi are known in the art to be suitable hosts for diversification of DNA, and filamentous fungi are preferred fungi. The invention includes fungal cells, either diploid or haploid and either as individual cells or as part of a larger assembly or organism, such as in macrofungi, and the like. Preferred strains of fungi used in in vivo diversification have several advantageous characteristics. Diversification is accomplished by mating a pair of haploid strains to create diploid parents, which then are crossed and cause in vivo diversification.

The haploid strains used to make the parents are of different and complimentary mating types. For example, a preferred pair of mating types is mating type A. *N. crassa* and mating type a. *N. crassa*. Fungi suitable for the invention also have other genetic characteristics required for heterokaryon compatibility. In *N. crassa* there are about eleven known loci that determine heterokaryon compatibility, het-c, het-d, het-e, het-i, het-5, het-6, het-7, het-8, het-9, het-10 and mating type. Preferred *N. crassa* carry the same allele of each of these loci except for mating types where one must have A mating type and the other a mating type. Preferably, fungi of the invention carry the same allele at each of the heterokaryon compatibility loci, except for mating type, to allow progeny of crosses to form heterokaryons in any combination of like mating type. Advantageously, a pair of fungi are used which include genetic features suppressing heterokaryon incompatibility between strains of different mating type. Such a genetic trait allows all combinations of progeny to form heterokaryons. Preferred *N. crassa* strains carry the mutation tol, which has been described by D. L. Newmeyer in Can. J. Genet. Cytol. 12:914–926 (1970).

Fungi of the invention can also include a forcing marker for the heterokaryon, such as one or more auxotrophic mutations. Forcing markers are preferred when the heterologous DNA codes for a component of a protein with more than one subunit. Preferably, if the multisubunit protein is made of different subunits, each parent will include the same forcing marker. If the multimeric protein has identical subunits, preferably, each parent has a different forcing marker. Preferred forcing markers include mutations that inactivate one of the following genes: trp-2, pan-2, thi, or arg. Inactivation of these genes leads to a requirement for tryptophan, pantothenic acid, thiamine, or arginine, respectively.

For diversifying heterologous DNA, the heterologous sequence is inserted into the fungal genome between a recombinator (recombination hotspot) and a detectable gene, to create a recombinant fungal genome. Preferably, each of the parent strains carries an auxotrophic mutation. Preferably, when selection for recombination at the detectable gene is used to enhance yield of heterologous sequences diversified by recombination, the detectable genes in each parent strain will be alleles that do not complement to ensure that any rare aneuploid progeny (progeny having two copies of the chromosome carrying the detectable gene) cannot give rise to a heterokaryon carrying both alleles that will no longer be auxotrophic for the trait of the detectable gene and thereby falsely mimic the desired recombinants. *N. crassa* employed in the present invention preferably carry an auxotrophic mutant of the his-3 gene. Preferably, each allele chosen has a mutation toward the 3' end of the his-3 gene. A suitable non complementing allele pair is K26 and K480. Suitable complementing pairs of his-3 alleles are K26 and K458 or K480 and K458. Suitable methods for selection of auxotrophic strains are described hereinbelow.

Advantageously, recombination at his-3 can be used to select for progeny in which the yield of recombinants is enhanced by ensuring that the whole of the heterologous DNA sequence was covered by a conversion tract. Typically, such recombination can be carried out with the a and the A strains each carrying a different his-3 allele and the SC medium will contain histidine in addition to any other required supplement. Preferably, the his-3 alleles chosen are a non-complementing pair, for example, one will be K26 and the other K480 (FIG. 10). This ensures that rare heterokaryons arising by the breakdown of anuploids containing two copies of chromosome 1 that form when there is failure of chromosome disjunction in meiosis, will not mimic his$^+$ recombinants. If the alleles were a complementing pair such as K26 and K458 or K480 and K458, the resulting heterokaryon would grow on medium lacking histidine, mimicking a his$^+$ recombinant. Suitable methods for selection of auxotrophic strains are described hereinbelow.

The strain is also chosen with characteristics that provide an active recombinator after insertion of the heterologous DNA into the strain. Preferably, each parent strain has a recombinator sequence and sequences surrounding the region in which heterologous DNA is inserted that have maximum homology to those regions on the plasmid. In preferred *N. crassa* parent strains, both cog$^L$ and lpl sequences are from the Lindegren strain. Preferred fungi also include a regulator of the recombinator or recombination hot spots that allows or activates the recombination hot spot, which directs recombination to a particular locus on the gene. Preferred *N. crassa* strains carry rec-2, which directs cog$^L$ to cause recombination in his-3 and the inserted heterologous DNA.

Typically, each parent strain contains one or more genes conferring resistance to an agent used to select against the presence of the whole plasmid. Preferably, each strain includes the mtr gene which confers sensitivity to p-flurophenylalanine as a negative selective agent. The parent fungal strains can also include a genetic characteristic that limits their growth on plating media. Preferred *N. crassa* include the mutation cot-1 C102t to limit growth on plating media. This strain can also include genetic characteristics such as mutations for additional sequences as required for enhance production and secretion of proteins produced by the heterologous gene or DNA sequence that is to be diversified. Some such genetic characteristics are described in U.S. Pat. No. 5,643,745.

Figure 4:
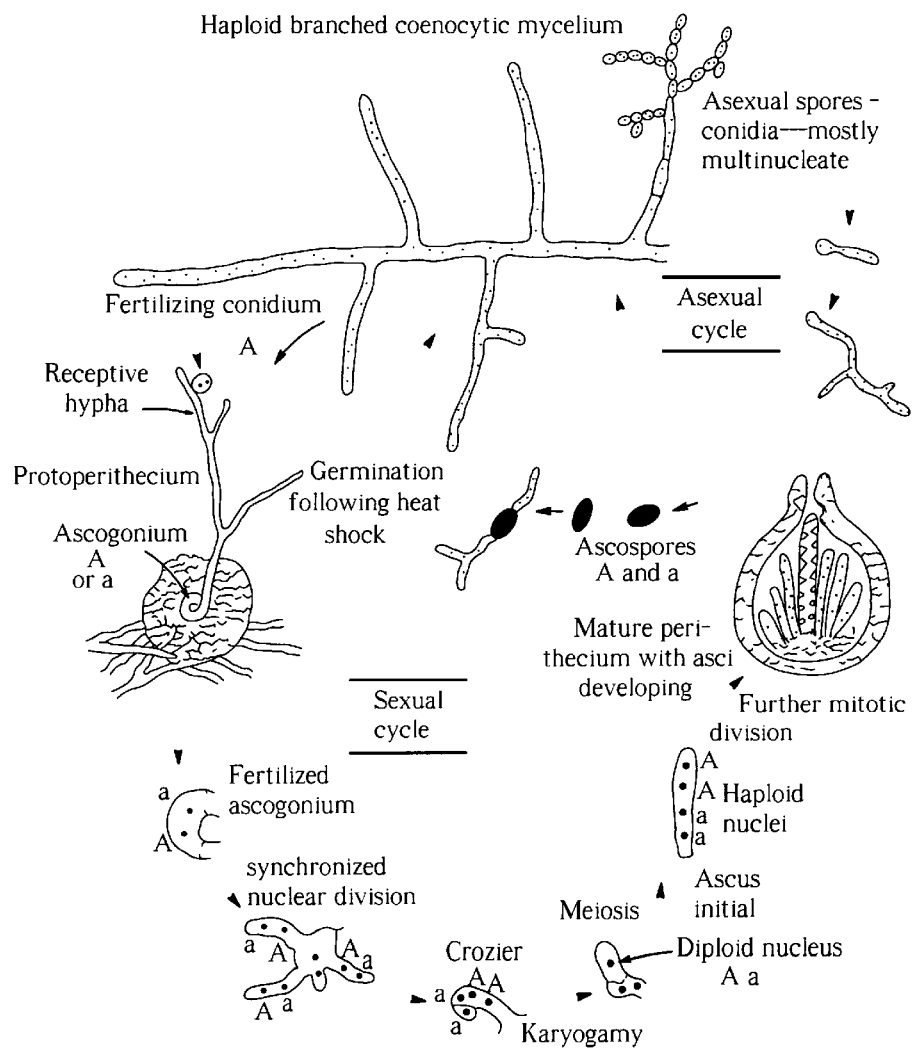
FIG. 4 illustrates the lifecycle of *Neurospora crassa*.

The life cycle of the filamentous fungus *Neurospora crassa* is outlined in FIG. 4 (see also J R S Fincham, Genetics, Wright 1983). Two strains can form a dikaryon providing they have a different mating type. Mating type in fungal species is conferred by one or more types of mating type loci that carry short sections of idiomorphic DNA (NP Beatty et al Mycological Res. 98:1309–1316 1994). When two strains of different mating type are mixed together on an appropriate medium and incubated under appropriate conditions, dikaryons are formed and a developmental process is initiated that establishes a diploid cell that then undergoes meiosis, with the accompanying genetic recombination. The haploid products of meiosis are spores, each containing one of the four products of a meiotic division or in eight spored fungi such as *N. crassa*, four spore pairs each formed as a result of meiosis being followed by a mitotic division prior to spore formation.

Strains of *N. crassa* can be cultured on any medium suitable for this type of filamentous fungus containing a suitable carbon source, any required vitamins, and any nutritional requirements, for example, such as for an auxotrophic mutant. One such medium is that described by H. J. Vogel in American Naturalist 98:435–446 (1964). The growth medium is solidified with agar when required. Typical *N. crassa* strains can be grown at temperatures between 20° C. and 36° C. Typical temperature sensitive mutants are grown at either 25° C. or 34° C. depending on the type of growth preferred.

The *N. crassa* is cultured until asexual spores called conidia are produced on the aerial hyphae (FIG. 4). The conidia are collected and used to propagate genetically identical cultures. Any suitable aconidiate mutants can be propagated by transfer of mycelial fragments to fresh medium.

Crosses of *N. crassa* are made by coinoculation of two strains of different mating type in a suitable medium for mating. Media suitable for mating include that of Westergaard and Mitchell (Am. J. Bot. 34:573–557 1947) or SC medium (Davis et al. Methods in Enzymol. 17A:79–143 1970), or Cornmeal medium. The crossing medium includes any specific nutrients required by the strains. The crossing medium is then incubated at a temperature suitable for the sexual cycle of *N. crassa*, typically 25° C. Crosses of *N. crassa* can also be made by inducing a single strain to develop protoperithecia such as by incubation on low nitrogen medium for a suitable time and at a suitable temperature. Protoperithecia are fertilized by conidia of the second strain.

Fertilization leads to formation of a dikaryon, karyogamy, formation of diploid cells, meiosis and formation of ascospores. Typically, a convenient laboratory scale cross yields at least about 5×10⁷ ascospores, or enough material to yield about $10^2$ to about $10^5$ or more, variants of heterologous DNA. Progeny from a cross are grown from ascospore by any appropriate method and individual progeny are recovered.

When one parent of a cross carries an auxotrophic mutation, ie a mutation requiring specific supplements to be added to the growth medium to compensate for their inability to synthesize the substance, half of the progeny of the cross will carry that mutation and will be unable to grow unless the growth medium is suitably supplemented. If both parents carry different auxotrophic mutations, only those progeny where the mutant genes are recombined will be able to grow if no supplement is added to the medium. When the auxotrophic mutations are alleles (mutant forms of the same gene) and the differences from the wild-type are not at the same place in the sequence of bases that make-up the gene, prototrophic recombinant progeny (recombinants having the DNA sequence of the wild-type and thus able to grow without the supplement required by the mutants) occur at a low frequency, typically 0.001% to 1.0% of the total progeny and sometimes more, depending upon the gene, the distance apart of the sites of mutation and proximity to a recombination hotspot.

Neurospora Recombination Hotspot cog

The recombination hotspot cog in Neurospora is particularly suitable for in vivo diversification of foreign sequences. It is located approximately 4 kilobases distal of the his-3 gene in which it stimulates recombination during meiosis (P J Yeadon and DEA Catcheside Cur. Genet. 28: 155–163 1995). This strongly active hotspot, cog, has been located on the *N. crassa* genome, cloned (P J Yeadon and DEA Catcheside Current Genetics, 28: 155–163 1995) and sequenced.

The relative placement of cog and his-3 varies to some extent in natural strains (Yeadon and Catcheside ibid). The multiple sequence differences that distinguish two strains of *N. crassa* were used to map the location of cog with respect to the flanking genes his-3 and lpl (FIG. 5) and the position of exchange points of recombination events initiated by cog. The cog recombination hotspot is approximately 4 kb 3' of the his-3 gene in the regulatory region of the lpl gene. In crosses between two different his-3 alleles, the alleles are recombined in up to 1% of progeny. Such recombinants acquire tracts of sequence information from a homologous chromosome that can stretch at least 6 kb back to cog. These tracts are frequently interrupted (FIG. 6). As a result, most progeny that experienced a recombination event initiated by cog have novel combinations of the polymorphic DNA sequences that distinguish the parents in the region between his-3 and cog.

Recombination is easily measured in crosses between his-3 mutants since those mutants require histidine for growth and recombination events that re-establish prototrophy (his⁺) permit the resulting strain to grow on media that do not contain histidine (T Angel et al Aust. J. Biol. Sci. 23: 1229–1240 1970). Selection of prototrophs by their ability to grow without the addition of histidine to the medium allows the isolation of a subset of the progeny of the cross in which the DNA located between his-3 and cog has experienced involvement in the intermolecular exchanges between homologous chromosomes that constitute a meiotic recombination event. Where the his-3 mutants each had juxtaposed, between them and cog, different versions of a heterologous gene or other DNA sequence that differ at two or more sites, each his⁺ recombinant will have a high probability of having a novel variant DNA sequence for the heterologous DNA due to recombination or to mutation, if errors occurred in repairing the DNA strands broken during recombination.

cog is an advantageous recombination hotspot for the purpose of in vivo diversification of heterologous DNA. This is because it catalyses a high frequency of recombination, generates long conversion tracts that are frequently interrupted, recombination in its vicinity is known to be tolerant of high levels of DNA sequence polymorphism, and the nearby his-3 gene has complementing alleles allowing the targeting of constructs into the his-3 gene without loss of a his-3 mutant marker required for enrichment of progeny in which the juxtaposed heterologous DNA has been diversified by recombination. Heterologous DNA to be diversified is functionally coupled, or juxtaposed, to the recombination hot spot. That is, the heterologous DNA is in a position in the genome, plasmid, or other DNA sequence subject to recombination in the presence of the recombinator or recombination hot spot. The degree of divergence in normal chromosomal sequence that has been used to study recombination in yeast is more than an order of magnitude less than the 3.5% sequence divergence in the 3' flank of his-3 used as markers in the study of recombination catalyzed by cog (FIG. 5, FIG. 6). Elimination of heterology in the 3' flank of cog led to less than two fold increase in gene conversion in his-3 , demonstrating that the Neurospora cog recombinator is tolerant of the high levels of sequence heterology required for efficient sequence diversification in vivo by recombination of homologous DNA having many sequence differences. Two alleles of cog are known. $cog^L$, present in the Lindegren laboratory strain, is a preferred recombinator. $cog^E$, present in the Emerson and St Lawrence 74A laboratory strains, yields recombination frequencies an order of magnitude lower than does $cog^L$.

The Neurospora cog hotspot is preferred due to advantageous characteristics such as a high frequency of interrupted conversion tracts, suitable marker genes for targeting plasmid constructs and enhancing the yield of recombinant forms of heterologous DNA, and promoters suitable for expressing the diversified sequences and secreting any protein product. The cog locus is a particularly preferred recombination hot spot. However other hot spots with advantageous characteristics of the cog locus are also preferred.

Other recombination hotspots in Neurospora and in other species are also suitable for in vivo diversification. Indeed, recombination hotspots can be expected in all genomes of those eukaryotes that reproduce sexually and also in the genomes of bacteria and other prokaryotes and their plasmid and viral parasites that are able to exchange genes. Such recombination hotspots include ones 5' of his-3 and 5' of am in *N. crassa*, 5' of each of his4, arg4, his2, and cys3 in *S. cerevisiae,* both within and 5' of ade6 and in *S. pombe,* and the like. Additional suitable hot spots include hotspots that affect recombination at his-1 and nit-2, near pyr-3, near sn, and near his-2 in Neurospora crassa and hotspots known to exist in the fungi *Aspergillus nidulans, Schizophillum commune,* and at other locations, including HOT1 in the genome of *Saccharomyces cereviseae.* Among these other suitable hot spots, ones 3' of his-3 and 3' of am in *N. crassa*, 3' of his4 and 3' of arg4 in *S. cerevisiae,* within ade6 in *S. pombe,* and the like, are believed to be more suitable.

Hot spots are also found in plants, such as maize. Mammalian hot spots include those in mouse (*Mus musculus*), where recombination hotspots are known close to the major histocompatibility locus, in human (*Homo sapiens*) and Chimpanzee, where hotspots are known near the gamma globulin loci, and, in humans, also near the retinoic acid alpha receptor gene and in the region of the repeat sequences associated with Charcot-Marie-Tooth neuropathy. There are also suitable recombination hot spots in diverse species.

Replacement of Sections of Chromosomes with Altered or Heterologous DNA

DNA sequences in fungal chromosomes can be altered by incorporating sequences that have been engineered in vitro in place of those in the chromosome. The engineered sequences can contain heterologous DNA in addition to altered forms of sections of the chromosomal DNA and can be additional to or a replacement for sections of chromosomal DNA sequences. The means of making these manipulations utilize the methods known in the art for DNA manipulation including: oligonucleotide synthesis, PCR amplification of DNA, restriction enzyme digestion, cloning in appropriate phage or plasmid vectors using suitable hosts species such as *Eschericia coli* as outlined in standard methods manuals (for example J Sambrook et al "Molecular Cloning" Cold Spring Harbor 1989), and the like.

The in vivo constructs can be introduced into fungal cells by a variety of procedures, referred to herein as transfection, that are known in the field of DNA manipulation (J Sambrook et al 1989, F J Bowring and DEA Catcheside Current Genetics 23: 496–500 1993) such that the in vitro modified DNA takes the place of the normal chromosomal sequence. Precise replacement requires that the DNA is incorporated in exactly the correct position by a breakage of the chromosomal DNA and insertion of the in vitro construct. In many species, exactly homologous insertion events are rare and selection of correct insertions is required to avoid DNA insertion at ectopic sites with limited or no DNA sequence homology. Correctly targeted insertions can be achieved by repair of a chromosomal mutation. Transplacement can be achieved as follows.

A DNA construct is prepared containing a shortened version of the his-3 gene from *Neurospora crassa* truncated at the 5' end and extending some distance 3' of the gene. The heterologous or in vitro modified DNA sequence to be targeted into the recipient cells inserted into this DNA at some point 3' of the his-3 gene. The exact junction for the point of insertion of the heterologous DNA can vary from construct to construct and be effected at a multiple cloning site built into the sequences 3' of the terminus of the his-3 gene, or whatever other gene is being targeted. The requirement is that the junction is not in DNA sequences coding for an essential cellular function.

Suitable plasmids include pBM60 (Margolin et al Fungal Genet. Newsl. 44:34–35 1997), pRAUW122 (R Aracano and R L Metzenberg Fungal Genet. Newsl. 43:9–13 1995), and pFJB1 (F J Bowring and DEA Catcheside Current Genet. 23: 496–500 1993), which are capable of replicating in *Escherichia coli* cells. Such a plasmid typically contains a truncated his-3 gene of *N. crassa*, sequences 3' of his-3 into which have been inserted a selectable marker, such as the hph gene coupled to a promoter that permits expression in *N. crassa*. The marker gene thus confers resistance to the antibiotic hygrornycin. The plasmid also contains a multiple cloning site for insertion of heterologous genes. The plasmids typically also contain a selectable marker such as bla, which confers ampicillin resistance to *E. coli* cells containing the plasmid. The plasmid also typically contains an *E. coli* DNA replication origin, permitting selection for cells containing the plasmid and cloning in *E. coli* of plasmid DNA into which heterologous sequences have been inserted into the multiple cloning site. To be suitable for the present invention, the plasmid lacks substantial sequence differences in the his-3 gene from that in the Neuropsora strain into which it is to be targeted and preferably contains the high frequency recombinator $cog^L$.

A suitable plasmid can be constructed using methods, in the art for DNA manipulation. A preferred plasmid includes a series of DNA sequences in the following order. First, the preferred plasmid has a sequence including the majority of the his-3 gene, but lacking a portion of the 5' end of the gene.

Preferably, the his-3 gene lacks a short portion of the sequence of the 5' end including the start codon. Preferably, the excluded sequence includes about 300 nucleotides from a position not less than about 687, preferably to about position 1000 in the sequence shown in FIG. 7. This first sequence preferably terminates beyond the stop codon of the his-3 gene. Preferably, the first sequence is a sequence from a his-3$^+$ strain of *N. crassa*, preferably the St. Lawrence 74A wild type, the Lindegren wild type, mutant K26 derived from Lindegren, or K458 mutant derived from Emerson A wild type.

Second, is an optional sequence including a promoter that is functional in *N. crassa*. Preferably, the second sequence is included when no such promoter is found in other DNA in the plasmid. Preferably the optional promoter sequence is functionally coupled to the expression and control of expression of a heterologous sequence.

Third, comes another optional sequence. The third sequence can be present when the heterologous or foreign sequence codes for a messenger RNA. When such a messenger RNA is produced, the fourth sequence can tag the messenger RNA for export of the protein product. Preferably, the third sequence is included when such export is desired and when no suitable tagging sequences are present elsewhere in the plasmid, such as in the heterologous or foreign DNA insert.

Fourth, is a sequence including a cloning site having cleavage sites for one or more restriction enzymes. This cloning site can be any suitable site for insertion of a heterologous gene or DNA sequence, preferably a gene or sequence not present elsewhere in the plasmid.

Fifth, is a recombination hotspot, or recombinator, sequence. Preferably this is a cog sequence, preferably a cog$^L$ allele. A preferred cog allele is from the 3' of the Lindegren wild type, preferably from about nucleotide 5412 to about nucleotide 6831.

Sixth, comes a sequence that provides homology downstream of cog. Preferably the sixth sequence includes sequences from the lpl gene, preferably from position about 6831 and in the 3' direction for about several hundred base pairs in the sequence shown in FIG. 7.

Seventh, is a sequence providing a marker gene providing for either positive or negative selection for the presence of the plasmid in *N. crassa*. A preferred marker gene for positive selection is hph$^R$ or another gene conferring hygromycin resistance. A preferred negative selection gene is mtr$^+$, conferring sensitivity to p-flurophenylalanine. Additional suitable genes providing for negative selection include those conferring sensitivity to a toxic substance.

Eighth is a sequence that provides a maker gene for the presence of the plasmid in *E. coli*. A preferred eighth sequence includes the bla marker gene or another gene encoding ampicillin resistance. Additional suitable genes include those conferring resistance to another antibiotic.

Ninth is a sequence that provides for amplification of the plasmid in *E. coli*. Preferably the ninth sequence is a replication origin functional in *E. Coli*.

Variants of this preferred plasmid can be constructed as well. Such variants include a plasmid lacking the sixth sequence, but relying on another sequence for homology downstream of cog. Such homology can result from the cog$^L$ sequences, which are included in the fifth sequence.

The construct is introduced by methods such as transfection, transformation or electroporation into a *N. crassa* cell or protoplast or spheroplast that contains a mutation in the gene to be targeted. Typically the targeted gene is the his-3 gene and the mutation is located some distance 3' of the point of truncation of the his-3 sequences within the DNA construct. The mutation renders the gene product non-functional, requiring that growth conditions are modified to permit cell growth. Typically, by addition of an amino acid such as histidine or other supplement as is required to the growth medium.

In this embodiment, the recipient cells are placed on medium lacking histidine to select for those that have had the histidine gene restored to functionality by insertion of the DNA construct or by a mutation event restoring a functional his-3 gene. Cells in which mutation events rather than transplacement events occur can be rejected by incorporating a selectable marker such as the hph gene that confers resistance to the antibiotic hygromycin as part of the heterologous DNA, using recipient cells that are hygromycin sensitive, and culturing them on medium containing hygromycin as well as lacking histidine.

The specific selectable marker built into the in vitro modified DNA can vary and is not confined to hygromycin resistance, or, indeed, to antibiotics. Alternative markers include a gene for synthesis of an essential metabolite where the recipient cell has that essential gene deleted. Cells that are able to grow on the selective medium will include those where exchange between the in vitro modified DNA and the cellular DNA has occurred in the interval between the 5' terminus of the truncation of the his-3 DNA sequences and the site of the his-3 mutation in the chromosome. This will restore a complete active copy of the his-3 gene in the chromosome with all or part of the in vitro construct, including any heterologous DNA built into it, inserted into the chromosome specifically at the his-3 gene.

Where only a single reciprocal exchange event occurs, the heterologous DNA will be flanked each side by DNA sequences that are homologous to one another. Each of these two DNA sequences is a near duplicate of the other comprising the his-3 gene and flanking sequences from the in vitro construct and the corresponding chromosomal copy. These sequences will be reciprocally recombined in a manner determined by the precise location of the single reciprocal exchange event.

Where exchange events occur both in the region of homology within his-3 and in the region of homology in the 3' flank of his-3, there will be no duplication and a proportion of the in vitro construct DNA including the whole of the heterologous sequence will be inserted exactly in place of the normal chromosomal DNA sequence in this region. This is termed transplacement. Transplacement can be effected in one step or in two steps in which the first exchange leads to insertion and the generation of a duplication and the second exchange leads to resolution of the duplication leaving the in vitro construct in place of the excised normal chromosomal sequence. Confirmation of correct transplacement can be accomplished by standard methods of DNA manipulation using techniques such as southern transfer, or PCR amplification and restriction enzyme digestion, to test the architecture of the relevant chromosomal region of the selected cells.

Duplicated DNA in some organisms, including *N. crassa*, suffers extensive mutations as a result of conversion of cytosine bases to thymine in a process known as repeat induced point mutation (RIP) that occurs during the expansion of the dikaryotic tissue which precedes karyogamy and meiosis (E U Selker Ann. Rev. Genet. 24: 579–613 1990). The mutations are so extensive that genes within the duplication are usually inactivated, making it unsuitable as a gene diversification mechanism. It is therefore advantageous to avoid duplications of a size susceptible to RIP in any gene manipulation process that requires passage of DNA through meiosis.

Constructing Strains of Fungi

The invention also relates to a method of preparing a strain of a fungus. Advantageously such a strain of fungus can be used for producing diversified DNA sequences and the gene products of the diversified sequences. Such a strain can provide markers for the isolation of recombinant forms of heterologous DNA, and production and isolation of diversified DNA. This method requires making a diploid fungal cell containing non-complementary alleles of a gene providing an auxotrophic mutation, which gene is functionally coupled to, adjacent to, or juxtaposed to the heterologous DNA to be diversified. This diploid allows enrichment for cells containing diversified DNA. A typical method used for making such a strain of fungus includes several steps.

A first fungal cell having a first allele of the gene providing an auxotrophic mutation is transfected with a first heterologous DNA and a second allele of the gene providing an auxotrophic mutation. In this method transfection can be accomplished employing a suitable cloning vehicle such as a plasmid, a viral vector, another suitable vector, and the like that includes the heterologous DNA and the desired allele of the gene. Advantageously, each of the first and second alleles encode a defective gene but are complementary alleles. The presence of the first and second allele of a gene following transfection of the first fungal cell establishes a first heterokaryon, which is grown to provide a first homokaryon containing the second allele of the gene and the first heterologous DNA.

A second fungal cell having a third allele of the gene providing an auxotrophic mutation is transfected with a cloning vehicle including a second heterologous DNA and a fourth allele of the gene providing an auxotrophic mutation. Advantageously, each of the third and fourth alleles encode a defective gene but are complementary alleles. The presence of the third and fourth allele of the gene providing an auxotrophic mutation following transfection of the second fungal cell establishes a second heterokaryon, which is grown to provide a second homokaryon containing the fourth allele of a gene and the second heterologous DNA. In a preferred embodiment, the first allele and the third allele are the same allele and the second and fourth alleles of the gene are non-complementing alleles. The desired fungal strain is established by crossing the first and second homokaryons.

Advantageously, in this method, the fungus is *Neurospora crassa*. Preferably, in *Neurospora crassa* the auxotrophic mutant is a his-3 auxotrophic mutant. Preferred auxotrophic mutants include his-3 K26, his-3 K458, and his-3 K480. Preferably, these are used in combinations such that the first and second fungal cells each carry his-3 K458, and the first fungal cell is transfected with his-3 K26 and the second transfected fungal cell is transfected with his-3 K480. Advantageously, the non-complementing pair of alleles is K26 and K480, which results in production of a dikaryon carrying both alleles that is unable to grow on media lacking histidine.

More specifically, targeting plasmid DNA into a specific chromosomal location is achieved by transfection of an auxotrophic mutant with a plasmid carrying non mutant sequence leading to the restoration of a normal gene in the recipient chromosome (FIG. 9) or with a plasmid carrying a complementing mutant gene (FIG. 10). Transformants with the plasmid DNA correctly targeted are selected by their ability to grow on media not supplemented with the requirements of the auxotrophic mutation. Where the fraction of progeny from a cross that experienced conversion of heterologous DNA is too low to provide a good yield of diversified sequences, it is necessary to be able to enrich for those that did experience conversion to provide the panel of diversified sequences. This can be achieved if a his-3 mutation remains in the chromosome of the recipient cell after insertion of the heterologous DNA.

In *Neurospora crassa*, several auxotrophic markers can be used for isolation of desired heterologous DNA. One preferred marker is the his-3 gene. Complementing allelic mutations of the his-3 gene (D G Catcheside and T Angel Aust. J. Biol. Sci. 27:219–29 1974) provide a means of achieving transplacement at his-3 leaving a his-3 mutation conferring a requirement in the chromosome carrying the heterologous DNA. This is made possible because his-3 codes for a peptide that forms a heteromultimeric protein, which allows selection of strains producing different combinations of subunits. Certain combinations of subunits will be inactive, and others active. For example, an enzyme formed by subunits coded by his-3 K458 is inactive and a heteromultimer containing subunits coded by his-3 K26 and other subunits coded by his-3 K458 is enzymatically active. This allows selection of heterokaryons that contain both types of nuclei. The desired heterokaryon can be specifically selected by its ability to grow on media that contain no added histidine.

A homokaryon containing only the desired nuclear type, for example, carrying the desired his-3 mutation and preferably the juxtaposed heterologous DNA, is isolated by picking colonies to slopes of minimal medium, growing to conidia and isolating homokaryons by establishing new cultures on medium containing histidine from single conidia. The conidia frequently give rise to homokaryons. The homokaryon can then be used as one parent of a cross used to diversify the heterologous DNA (FIG. 10). A second homokaryon having a non-complementary allele of the gene providing auxotrophy is prepared analogously to the first homokaryon. This provides the second parent for crossing.

The present invention can be better understood with reference to the following examples. These examples are intended to be representative of specific embodiments of the invention, and are not intended as limiting the scope of the invention.

EXAMPLES

Example 1

Long, Interrupted Conversion Tracts by cog in *Neurospora crassa*

We have used 14 PCR products ranging from 330 to 540 bp in length each having easily detectable restriction site polymorphism (RSP) or sequence length polymorphism (SLP) to investigate the molecular outcome of conversion within his-3 and 3.8 kb distal of this gene. A HpaI RSP allowed extension of the analysis to 6 kb proximal of his-3. The RSPs and SLP s were used to determine the parental origin of each segment in 38 progeny prototrophic for histidine from crosses heteroallelic for cog and his-3. Progeny from diploids that were homozygous rec-2 and heterozygous rec-2/rec-2+ were examined to investigate differences in outcome due to the inactivation of the cog function by rec-2$^+$ and from diploids in which the his-3 mutation closer to cog was cis (K1201/K26 and K504/K26) or trans (K26/K874) to $cog^L$ to detect differences resulting from the bias for conversion to be initiated on the $cog^L$ chromosome. The large number of heterologies scored (16 in 6.9 kb, including the sequence variations responsible for the his-3 mutations) permits measurement of the length of conversion tracts and detection of discontinuity and location of crossovers between flanking markers arginine-1 (proximal of his-3) and ad-3 (distal), if they occur within the region surveyed.

Materials and Methods

Origin of Neurospora parental strains: K26 (Table 1) was isolated in a strain of Lindegren 25a origin (Catcheside and Angel 1974 Aust. J. Biol. Sci. 27: 219–229.); K1201, K504, K374, arg-1 K166 and ad-3 K118 in Emerson a (Catcheside and Angel 1974 ibid). T10988 and T10990 were generated by Steve Fitter and T10997 by Fred Bowring. F strains are from the collection of D. G. Catcheside.

Culture methods: Methods were those described by Bowring and Catcheside (1996 Genetics 143: 129–136.), except that crosses were supplemented with 200 μg/ml alanine, 500 μg/ml arginine and 200 μg/ml adenine. Vegetative cultures were supplemented with 500 μg/ml alanine, 500 μg/ml arginine, 200 μg/ml histidine, and 400 μg/ml adenosine as required.

Isolation of recombinant progeny: Ascospores were treated as described in Catcheside (1981 Genetics 98: 55–76) except that plates contained 0.05% of glucose and fructose in place of sucrose were supplemented with arginine, adenosine and alanine and incubated for 3 days at 34°. His$^+$ colonies were picked to slopes and grown at 25°. Cultures were streaked for single colonies and reisolated before further analysis. Flanking markers were determined by the ability of a prototroph to grow either without adenosine or without arginine.

T11245–T11320 (Table 1) are histidine prototrophs isolated for the purpose of conversion tract mapping. T11245–T11252 were derived from a cross between T10988 and T4393, 11253–T11260 from a cross between T10990 and F7446, and T11261–T11268 from across between T10990 and F7448. T11269–T11274, T11302–T11305 and T11320 were derived from three separate crosses between T10987 and T4398. T11275–T11277 and T11306–T11308 were from two independent crosses between T10990 and T10997.

Preparation of PCR templates: Quick template DNA was made from each progeny strain as described in Yeadon and Catcheside (1996 Fungal Genetics Newsletter 43: 71.). For the parental strains, genomic DNA was prepared as described by Yeadon and Catcheside (1995 Curr. Genet. 28: 155–163.).

PCR amplification: PCR was performed for 40 cycles (Saike, et al. 1988 Science 239: 487–491) using a PTC-100 Thermal Sequencer (M J Research Inc., supplied by Bresatec) and Taq DNA polymerase (BTQ-1; Bresatec) in a total reaction volume of 50 μl. Fifty nanograms of genomic DNA or 2 μl of quick template DNA was used as template in each reaction. Annealing was at 50° and MgCl$_2$ 2.5 mM.

PCR primers: his-3 primers were designed using the program PCRPRIM on ANGIS from the sequence of histidine-3 published by Legerton and Yanofsky (1985 Gene 39: 129–140) and corrected as necessary where sequence information conflicted with the published sequence. Primers distal of his-3 (FIG. 5) were designed using sequence previously obtained for the intergenic regions (Yeadon and Catcheside 1995 Curr. Genet. 28: 155–163). The P1 pair of primers (FIG. 5) was designed after a sequence walk proximal of his-3.

Restriction digests and electrophoresis: PCR products were digested with 3 units of the appropriate restriction enzyme (New England Biolabs) for 90 min. as described by the manufacturer and the products resolved by electrophoresis on 3% NuSieve 3:1 agarose (FMC Bioproducts) in TAE, 3 V/cm for 3 hr.

Detection of RSP and SLP in the Lindegren and Emerson parents: Genomic DNA from T10987 (Lindegren descent) and F7448 (Emerson descent) was used as template to amplify DNA segments (FIG. 5) predicted from the sequence to have RSPs or SLPs that differentiate each parent. PCR products were digested where necessary with appropriate restriction enzymes and fragments resolved by electrophoresis (data not shown). Each pair of PCR products yielded the expected distinguishable patterns, length polymorphisms in GAP(X) and C8, and a restriction site present in only one parent in the remainder. The polymorphism in C8 reflects the presence of the inverted repeat transposable element Guest in Emerson (Yeadon and Catcheside 1995 Mol. Gen. Genet. 247: 105–109) yielding a product 102 bp longer than that from Lindegren. The HpaI RSP 6 kb proximal of his-3, discovered during mapping of genomic DNA (Yeadon and Catcheside 1995 Curr. Genet. 28: 155–163, FIG. 5), assisted location of crossovers proximal of his-3 and was detected by Southern analysis as described in Yeadon and Catcheside (1995 Curr. Genet. 28: 155–163.). The probe was λJY25 (Yeadon and Catcheside (1995 Curr. Genet. 28: 155–163.).

Determination of the parental origin of sequence segments from recombinant progeny: Fourteen of the 15 segments (FIG. 5) were amplified by PCR from the 38 histidine prototropic progeny, and the parental origin of each identified from their restriction pattern or, in the case of C8, from the length polymorphism due to Guest. The segment labeled GAP(X) (FIG. 5) was not used since reliable sequence was difficult to obtain, impeding identification of RSPs and, since a single site could not be surveyed, the parental origin of segments different in length from that in either parent would be uncertain.

Results

Bias in the chromosome receiving information: Among the 23 progeny of crosses homozygous rec-2, four strains (T11247, T11265, T11266 and T11267) had exchanges with no detectable conversion (henceforth termed "simple crossovers") between the his-3 mutations. In two others, T11262 and T11264, there were alternate positions in which the crossover could have occurred, indicated by the symbol "X?" in FIG. 6. In 16 of these 23 progeny the Lindegren chromosome must be the recipient of information, and in T11261 alone was Emerson most probably the recipient of information. It is clear that the Lindegren chromosome, which carries the high frequency $cog^L$ allele, was converted more often than the Emerson chromosome. In contrast, in the 11 progeny from crosses in which rec-2$^+$ is present, the two chromosomes were equally likely to be converted: one has a simple crossover (T11269), there were four in which Emerson was converted (T11270, T11274, T11307 and T11320), three where Lindegren was converted (T11275, T11276, and T11306) and three (T11272, T11302 and T11304) where the recipient of information cannot be determined.

Positions of crossovers: Nine of the 23 progeny from rec-2/rec-2 crosses (39%) had at least one crossover between arg-1 and ad-3 (FIG. 6). Three of these were between arg-1 and the HpaI RSP (H) 6 kb proximal of his-3 (in T11264, T11266 and T11268), one was between H and his-3 (in T11252), seven were within his-3 (in T11245, T11247, T11262, T11264, T11265, T11266 and T11268) and one (T11261) was between cog and ad-3. Seven of the 11 progeny from crosses in which rec-$2^+$ was present (64%) had crossovers between the flanking markers (FIG. 6). Two of these were between arg-1 and H (T11276 and T11307), four were within the his-3 gene (T11269, T11272, T11302 and T11304) and one (T11275) between the C3 and C9 heterologies distal of cog.

Length of conversion tracts: Conversion tracts in prototrophs from crosses homozygous rec-2 vary in length (FIG. 6). All prototrophs, except those with simple crossovers and the two potential revertants, showed conversion of more than one marker. The longest continuous tracts were those in T11254 and T11259 that cover the region between the R1 and C9 heterologies, 5.6 kb apart. RSP typing distal of C9 showed that the tract in T11254 terminates <185 bp distal of the heterology in C9, and that in T11259 ends >300 bp and <1178 bp distal of the C9 heterology (data not shown). Thus the longest tract extended >5.9 kb.

The presence of rec-$2^+$ results in shorter conversion tracts that did not extend distal of his-3. The longest continuous conversion tracts in these progeny are in T11270 and T11274. The tracts cover R1, K504 and P1 were thus at least 940 bp long.

Discontinuity in conversion tracts: Among progeny from crosses homozygous rec-2, there were 17 that showed evidence of conversion (FIG. 6). Of these, conversion tracts were discontinuous in eight (47%). Ten of the 11 progeny from crosses including rec-$2^+$ (FIG. 6) showed evidence of conversion and in three of these the tracts were discontinuous (30%). The difference between discontinuity of tracts in crosses in which rec-$2^+$ was present or absent was not significant ($X^2=0.25$ with Yates' correction; $P>0.5$). In total, 11 of 27 (41%) conversion tracts were discontinuous.

Association of crossovers with conversion: At least one crossover between the flanking markers arg-1 and ad-3 occurred in 47% of the prototrophs (16 of 34; FIG. 6). Of the prototrophs from crosses homozygous rec-2, three of the crossovers (in T11264, T11266 and T11268) were between H and arg-1 and were likely to be too distant to be associated with conversion. Those crossovers in T11252 and T11261 are also sufficiently distant that their association with conversion is doubtful. This leaves seven crossovers that may be associated with conversion initiated by $cog^L$, although four of these are simple crossovers, with no evidence of conversion. Thus, ignoring simple crossovers, 16% of prototrophs (three of 19) from crosses homozygous rec-2 had crossovers apparently associated with conversion. If simple crossovers are included as potentially associated with conversion, then 30% of these prototrophs (seven of 23) had an associated crossover.

Five of the seven crossovers in progeny from crosses heterozygous rec-2/rec-$2^+$ were within the region surveyed; one was a simple crossover (T11269), one (T11275) was sufficiently distant that an association with conversion is doubtful, but three (in T11272, T11302 and T11304) were at ends of conversion tracts and thus may be associated with conversion. The two remaining crossovers (in T11276 and T11307) were >6 kb from the proximal end of his-3 and were unlikely to be associated with conversion at this locus. Of the 10 prototrophs from crosses heterozygous rec-2/rec-$2^+$ (cog inactive) that had evidence of conversion, three (30%) have crossovers that may be associated with conversion. If simple crossovers are included, 36% of these prototrophs (four of 11) had crossovers that may be associated with conversion. In total, 11 of 34 prototrophs (32%) had crossovers that may be associated with conversion. The presence or absence of rec-$2^+$ had no significant effect on the association between conversion and crossing over in prototrophic progeny ($X^2=0.31$ with Yates' correction; $P>0.5$).

Discussion

Regulation of recombination in the his-3 region of Neurospora by the unlinked gene rec-2, the dominant allele of which (rec-$2^+$) prevents the initiation of recombination at cog (Catcheside and Angel 1974 Aust. J. Biol. Sci. 27: 219–229.), allows separation of events at his-3 into those that are cog-related and those that are not. Apart from the additional aspect of local regulation of recombination in Neurospora, there are many similarities between cog and yeast hotspots that suggest a common mode of activity.

Convertants at his-3 manifest a bias in the direction of information transfer. Of the 23 prototrophs from crosses lacking rec-$2^+$, in only one was Emerson, almost certainly the recipient of information (FIG. 6). Likewise in both budding and fission yeasts, where a hotspot has alleles that differ in activity such as the ade6 M26 hotspot of *S. pombe* (Gutz 1971 Genetics 69: 317–337) or the promoter deletion that removes hotspot activity at ARG4 of *S. cerevisias* (Nicholas, et al. 1989 Nature 338: 35–39), the chromosome on which recombination is initiated is the recipient of information.

Conversion tracts at different hotspots vary in length, dependent both on the locus and the mode of selection of progeny. The length of conversion tracts at his-3 in Neurospora is within the range of those measured in yeast at several loci. Conversion tracts at his-3 can be over 5.9 kb long (FIG. 6), but the distance between the recombinator and the gene may select for a subset enriched for the longest tracts in prototrophic progeny. The degree of discontinuity of conversion tracts appears to vary between loci as well as between species. Forty-one percent of conversion tracts in this study are discontinuous (FIG. 6). The discontinuities of conversion tracts occur within the intergenic and divergent sequences between his-3 and cog, that have no known cellular function, further diversifying these sequences. This shows that any pair of homologous but divergent foreign DNA sequences inserted into this region will also be diversified.

Example 2

Analysis of Conversion Tracts Associated with Recombination Events at the am Locus of *Neurospora crassa*

Introduction

The incidence of crossing over between flanking markers is enhanced when gene conversion is observed at an intervening locus and this is taken as evidence that gene conversion and crossing over are intimately associated. This view was strengthened when Hurst .et al, (Hurst D, Fogel S, Mortimer R (1972) Conversion associated recombination in yeast Proc Natl Acad Sci USA 69: 101–105) reported that in *Saccharomyces cerevisiae*, half of conversion events enjoyed an associated crossover. However, these data were not corrected for incidental exchanges in the regions flanking the converted loci (Stadler D R (1973) The Mechanism of intragenic recombination Ann Rev Genet 7: 113–127) and when that correction was made, approximately 35% (r=0.35) of conversion events were found to have an associated crossover (Fogel S, Mortimer R, Lusnak K, Tavares F (1979) Meiotic gene conversion: a signal of the basic recombination event in yeast Cold Spring Harbor Symp Quant Biol 43: 1325–1341). The level of association between conversion and crossing over reported for Neurospora is similar to that in *S. cerevisiae* (Neurospora r=0.33)

and the Neurospora am locus is not extraordinary in this respect (am, r=0.26; Perkins D D, Lande R, Stahl F W (1993) Estimates of the proportion of recombination intermediates that are resolved with crossing over in *Neurospora crassa* Genetics 133: 690–691).

Restriction site polymorphisms (RSPs) either side of and tightly linked to the Neurospora am locus, were used to examine the association between gene conversion and crossing over (Bowring and Catcheside, 1996). Analysis of prototrophs from a repulsion phase cross heteroallelic for the mutations $am^1$ and $am^6$ (cross B163) revealed that the majority of crossovers between conventional flanking markers were outside of the region bounded by RSPs and thus, that these events were remote from am and the event that generated a prototroph. It was concluded that a maximum of 7% ($r \leq 0.07$) of am conversions enjoyed an associated crossover.

am and flanking regions in the B163 parents were sequenced which revealed nine sequence polymorphisms. Five of these, together with the two mutant alleles have been used to investigate the nature of recombination events in B163 prototrophs in more detail.

Materials and methods.

Crossing methods, prototroph isolation, DNA preparation and classification of flanking markers were described in Bowring and Catcheside (1996)(Genetics 143: 129–136.) B163 is a cross between F11089 and F6325. F11089 (A, rec-3, cot-1 C102(t); sp B132, $am^1$) and F6325 (a, rec-3; cot-1 C102(t); $am^6$, his-1 K627) are D R Smyth and D G Catcheside stocks respectively. Among 205 am prototrophs from B163 selected at random, 145 were $sp^+$ his-1, 14 were sp his-$1^+$, 16 were $sp^+$ his-$1^+$ and 30 were sp his1. 84 of these (27 $sp^+$ his-1 randomly selected, all of the $sp^+$ his-$1^+$ progeny, all but 1 of the sp his-$1^+$ and 2 of the sp his-1 progeny lost during processing) were assayed for molecular markers (Bowring and Catcheside, 1996, ibid).

Primers (FIG. 11) were designed using the program "PCRPRIM" on ANGIS and the am sequence data of Kuinaird and Fincham (1983). Primer OL, the upstream end of which is located 188 bp beyond the upstream extent of Kiimaird and Fincham's sequence, was designed using sequence data obtained from J. A. Kinsey. PCR was carried out in a Corbett FTS-1 cycler. $MgCl_2$ was included at a final concentration of 2.5 mM. TAQ polymerase was from Bresatec (Adelaide, South Australia). A five minute denaturation step was followed by 30 cycles with 1 min. at 94 C., 1 min. at 50 C. and 1 min. at 72 C.

PCR products were purified (Wizard, Promega) and sequenced on an Applied BioSystems automated sequencer using both forward and reverse primers. Digestion of PCR amplified fragments with the appropriate restriction enzyme was used to determine the alleles carried by prototrophs isolated from cross B163: the F polymorphism by digesting the PCR product amplified with the OL-1R primers with FokI; Bd and Bp by digesting the fragment amplified with 1L-2R with MboI, S, by digesting the sequence amplified with 1L-2R with MseI and A, by digesting the fragment amplified with 2L-3R with BsmA1. Primer OL was used with 1R in the F determination since the polymorphic FokI cleavage site was very close to primer 1L. In all determinations except S, the amplified fragment had at least one non-polymorphic site for the appropriate restriction enzyme allowing for detection of false negatives. While this was not possible for S, because the same PCR product was digested with MboII for the determination of Bp and Bd and MseI for the determination of S, and as none of the products were refractory to MLboII digestion (data not shown), it seems unlikely that any progeny were misclassified for S. Digestions were carried out according to the suppliers suggested protocol. MboII was from Promega and all other restriction enzymes from New England Biolabs.

Results

Figure 11:
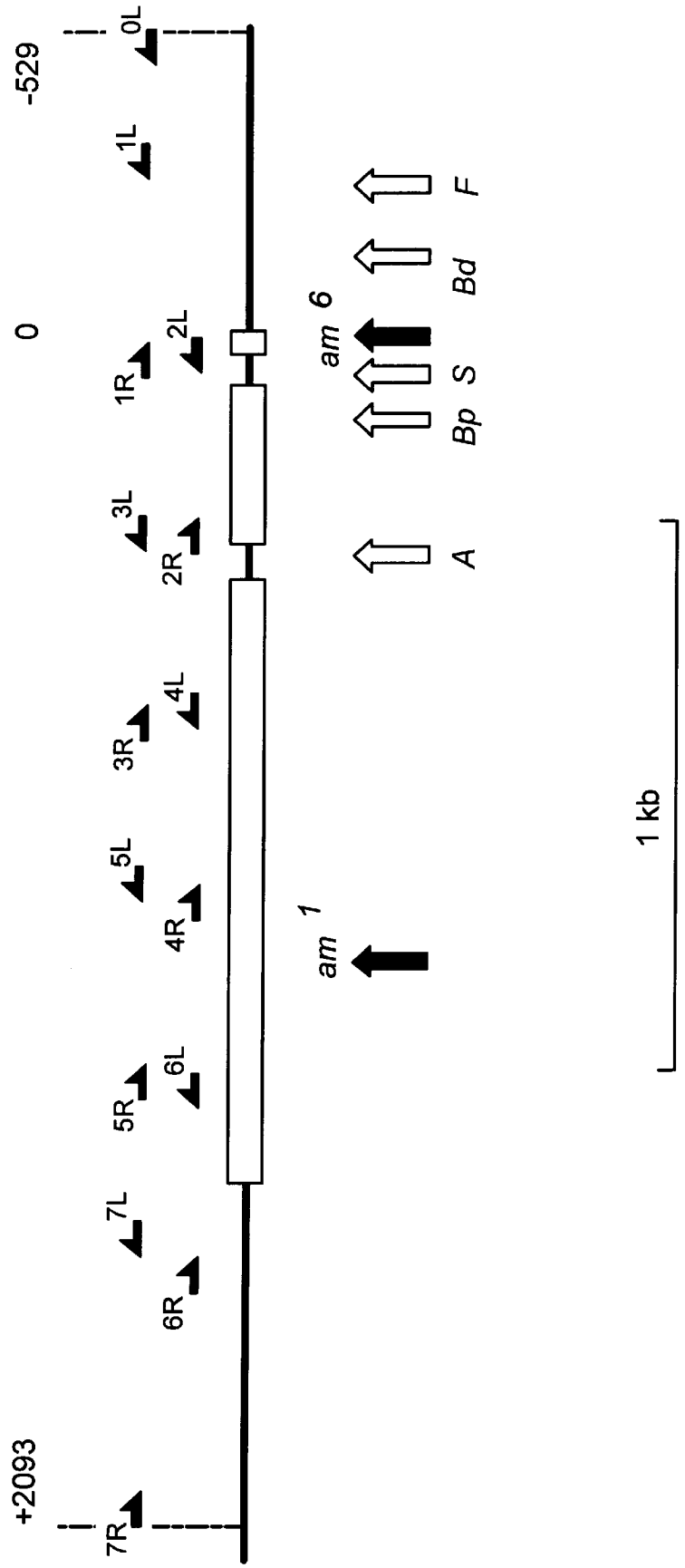
FIG. 11 illustrates sequence polymorphism between F11089 and F6325 at am and PCR primer sets used in sequencing and genotype determinations.

Sequence polymorphism in B163 parents at the am locus. The position of crossovers in the am region of Neurospora linkage group V has been determined in 84 prototrophs from a cross heteroallelic $am^1$ $am^6$, using both the conventional flanking gene markers sp ≈6cM proximal and his-1 ≈3cM distal and also close polymorphic restriction sites HP 8.3 kb proximal and HD 5.7 kb distal (Cross B163: Bowring and Catcheside, 1996 ibid). To obtain additional markers to map conversion tracts, the am coding region together with 311 bp upstream and 582 bp downstream (in total, 2381 bp) were sequenced in the B163 parents using seven PCR primer pairs (FIG. 11).

Of the nine natural polymorphisms, three are in the 311 bp upstream of am, one in intron I, a conservative base substitution in exon II, and three in intron II. No natural polymorphism was detected beyond intron II in the 1043 bp of am coding sequences in exon III and only one in the 582 bp of sequences downstream of the am stop codon.

Five of the nine sequence polymorphisms resulted in restriction site differences. These five sites, together with the $am^1$ and $am^6$ alleles provide seven readily detectable points of difference in the 1437 bp from 302 bp upstream to 1134 bp into the am coding region.

Segregation of markers in B163 prototrophs. The location of markers is shown in FIG. 11. The genetic constitution of the parents of cross B163, F6325 and F11089, together with the distribution of markers amongst their prototrophic progeny is detailed in FIG. 14.

Figure 14:
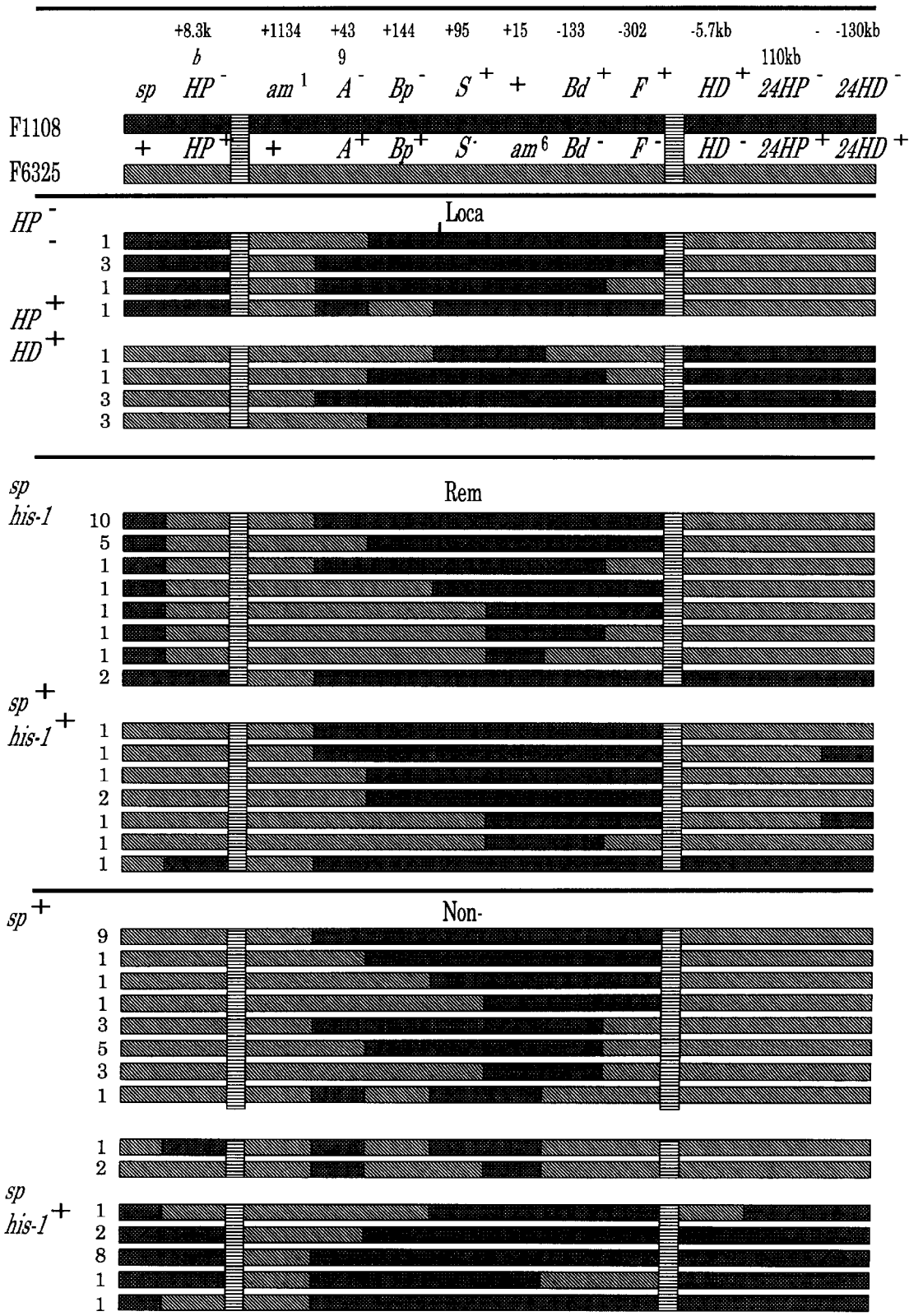
FIG. 14 illustrates the constitution of B163 parents and prototrophic offspring. Data for A, HP, HD, 24HP, 24HD1, and his-1 are from (Bowring and Catcheside, 1996). Positions of markers relative to the first base of the first am codon, in basepairs unless otherwise indicated, are shown above marker designations. All markers except sp, $am^1$, $am^6$ and his-1 are restriction site differences and a superscripted + indicates the presence of that site. The observed number of each prototroph type is shown to the left of the bars. The Local Crossover group have an exchange between HP and HD while the Remote Crossover group have an exchange in either the sp to HP or HD to his-1 intervals. The Parental group have a parental association of sp and his-1.

The composition of the local crossover group. As reported previously (Bowring and Catcheside, 1996 ibid) 14 B163 prototrophs had a crossover close enough to be considered associated with the conversion event at am. Eight of these 14 have a crossover point which appears separated from the converted region by a non-converted segment while in the remaining six there is an apparently uninterrupted transition from F6325 to F11089 DNA in am (FIG. 14).

Relative proportion of $am^6$ and $am^1$ conversions. Those am prototrophs with the F6325 and F11089 association of HP and HD (the remote crossover and non-crossover groups, FIG. 14) represent conversion of the 5' allele $am^6$ and the 3' allele $am^1$ respectively. Extrapolation of the data from the 27 of 145 $sp^{30}$ his-1 progeny analyzed at the DNA level and correction for the fact that only 13 of the 14 sp his-$1^+$ and 28 of the 30 sp his-1 prototrophs were available for such analysis (Bowring and Catcheside, 1996), suggests that 17.2 (9%) and 173.8 (91%) out of the total of 191 progeny that either experienced no crossover or a crossover remote from am were due to conversion of $am^1$ and $am^6$ respectively.

Figure 12:
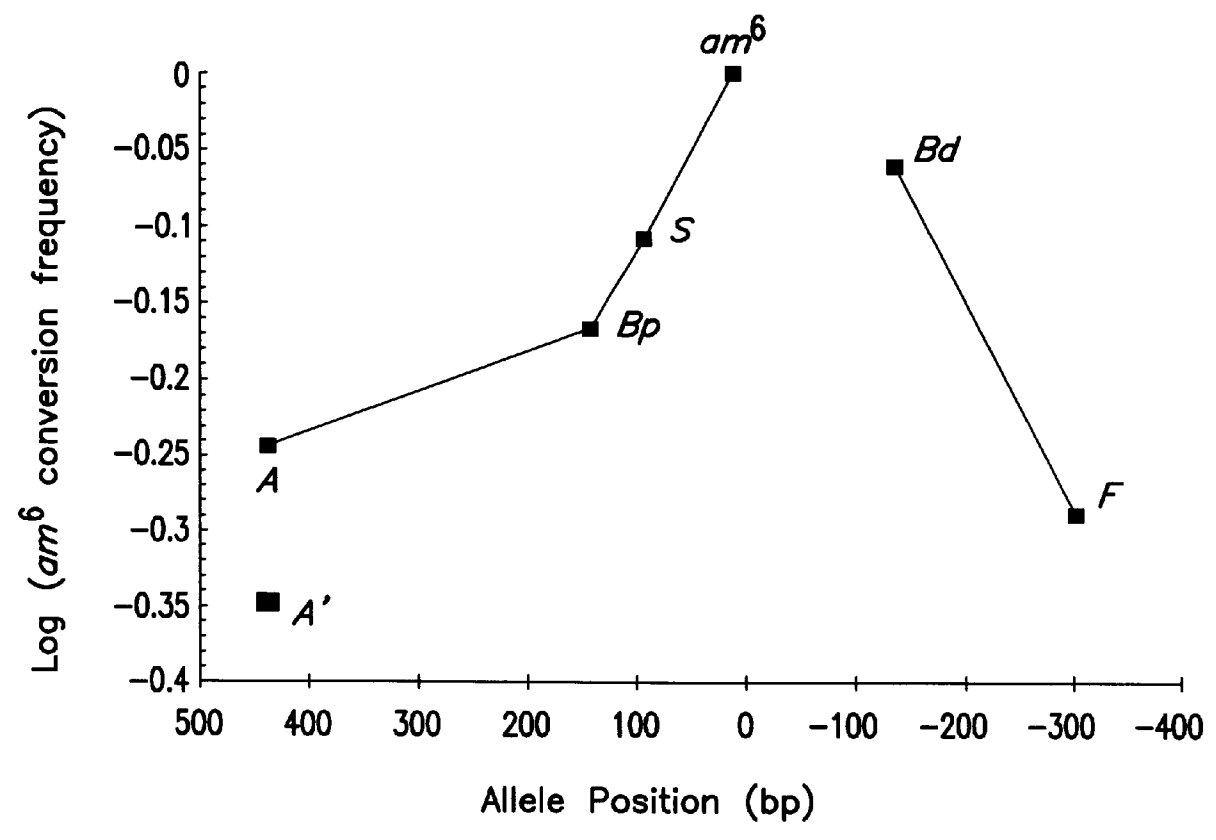

Polarity of conversion within am. The conversion frequency of each of the seven B163 alleles among $am^6$convertants is shown in FIG. 12. Data for progeny not analyzed at the molecular level were extrapolated as above. Conversion frequency peaks between $am^6$ and Bd and declines either side. 87% of $am^6$ convertants experienced co-conversion of Bd.

Figure 13:
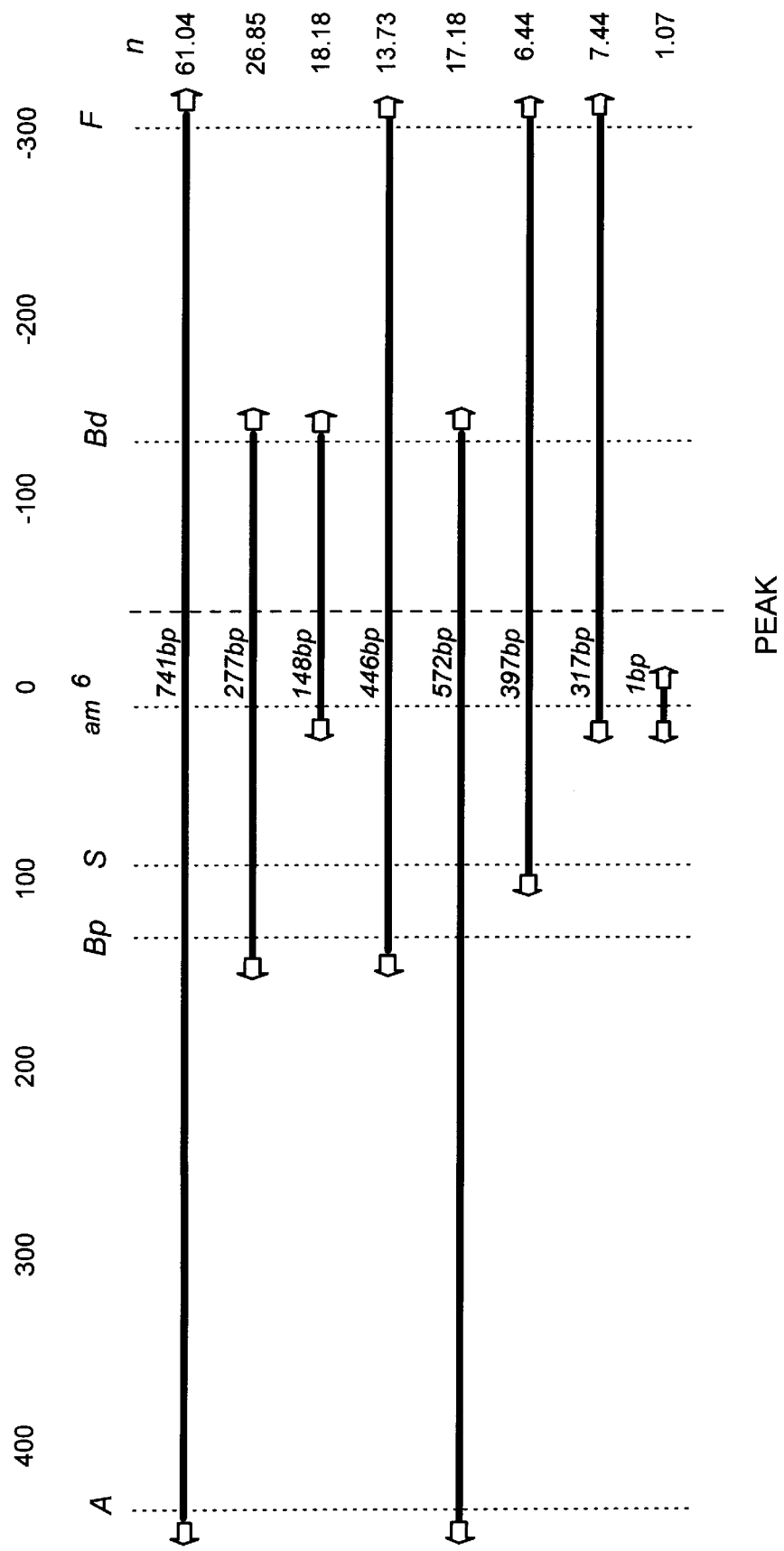
FIG. 13 illustrates minimum conversion tract coverage. Data are for $am^6$ convertants and were extrapolated to include progeny for which molecular markers were not scored (see hereinbelow). Position relative to the first base of the first am codon is shown in basepairs at the top. Peak is the position of the inferred peak of conversion events. Each estimate is a minimum since the spacing of markers does not allow for exact positioning of tract ends.

Conversion tract length. For $am^6$ conversions which form the larger class, markers either side of am make an estimate of minimum tract length possible. Each estimate is necessarily a minimum since exact positioning of tract termination points is not possible and many tracts end distal of F but proximal of HD which is 5.4 kb away from F. The estimate must also be made with the caveat that selection for am prototrophs may select against longer tracts under some circumstances. For instance, an excision tract that covers the position of both mutant alleles on a given homologue will not yield a prototroph if initiation occurs to one side of the allele pair. The most frequent minimum length of conversion tracts among prototrophs is 741 bp (FIG. 13) although 60% of the tracts had a minimum length shorter than this and half of these had a maximum length shorter than 741 bp. By extrapolation, 12% of conversion tracts at am excluding those with an apparently associated crossover, were discontinuous.

Discussion

The segregation of sequence polymorphisms among protorophs from cross B163 reveals information about the meiotic recombination event at am. The majority of events involved conversion of the $am^6$ allele and the conversion frequency of unselected alleles among such convertants suggests a peak of events immediately 5' of this allele. Conversion tracts with a minimum length up to 741 bp were detectable with the available markers. Although 40% were this length or more, at least 30% of tracts were shorter.

Smyth (Smyth D R (1970) Genetic control of recombination in the amination-1 region of *Neurospora crassa*, PhD Thesis, Australian National University) concluded, on the basis of data from more than 60 repulsion phase crosses of strains harboring various pairs of am alleles, that there is polarity across am with decreasing conversion frequency from 5' to 3'. Our data on the relative conversion frequency of seven am alleles among $am^6$ convertants in cross B163 (FIG. 12) confirm that conversion is most frequent at the 5' end of the gene and in addition provides evidence that the incidence of conversion peaks 5' of am and declines in frequency in both directions. A gradient of decreasing conversion frequency was also observed either side of the ARG4 initiation site in *S. cerevisiae* (Nicolas A, Treco D, Schultes N P, Szostak J W (1989) An initiation site for meiotic gene conversion in the yeast *Saccharomyces cerevisiae* Nature 338: 35–39; Schultes N P, Szostak J W (1990) Decreasing gradients of gene conversion on both sides of the initiation site for meiotic recombination at the ARG4 locus in yeast Genetics 126:813–822). The inferred conversion peak between $am^6$ and Bd suggests that conversion events are initiated in this interval, although the relative conversion frequency of these two alleles could also reflect variability in the position of initiation centered around Bd. The high frequency of $am^6$/Bd co-conversion (87%) is, however, consistent with initiation between these markers. Schultes and Szostak (1990) reported that markers either side of the ARG4 initiation site co-converted at a frequency of between 64 and 91%.

A poorly repaired mismatch in am? In *S. cerevisiae*, the segregation of alleles that generate poorly repaired mismatches (PMS alleles) at HIS4 (Detloff P, White M A, Petes T D (1992) Analysis of a gene conversion gradient at the HIS4 locus in *Saccharomyces cerevisiae* Genetics 132: 113–123) and of usually well repaired mismatches in mismatch repair deficient strains at this locus (Reenan R A G, Kolodner R D (1992b) Characterization of insertion mutations in the *Saccharomyces cervisiae* MSH1 and MSH2 genes: evidence for separate mitochondrial and nuclear functions Genetics 132: 975–985; Alani E, Reenan R A G, Kolodner R D (1994) Interaction between mismatch repair and genetic recombination in *Saccharomyces cervisiae* Genetics 137: 19–39) and at ARG4 (Alani et al., 1994) suggests an influence of mismatch repair on gene conversion. In either case, polarity gradients are less steep. C/C pairings are among those mismatches that are poorly repaired in *S. cerevisiae* (Petes T D, Malone R E, Symington L S (1991) Recombination in yeast. In: Broach J R, Jones E W, Pringle J R (eds) The Molecular and Cellular Biology of the Yeast Saccharomyces, volume 1, Cold Spring Harbor Laboratory, Cold Spring Harbor, N.Y.). In cross B163, a C/C mismatch results from pairing of the non-transcribed strand of F11089 and the transcribed strand of F6325 at the A_site. If, as is the case in *S. cerevisiae,* C/C mismatches are poorly repaired in Neurospora, this might explain two related observations on the segregation of A in B163 progeny. Firstly, where there is discontinuity in conversion tracts among $am^6$ convertants, the A site is always involved. Secondly, the conversion gradient from Bp to A appears shallower than either that from $am^6$ to Bp or that from Bd to F on the other, distal, side of the inferred conversion peak. A lies above the line describing the $am^6$ to Bp gradient but approaches it more closely when A conversions associated with discontinuous tracts are excluded (FIG. 12).

The relationship between conversion and crossing over. The objective was to determine if there was anything unusual about conversion tracts at am that might explain the low level of association between conversion and crossing over at this locus. Tracts at am appear similar to those reported for *S. cerevisiae* and *S. pombe*. While some of the $am^6$ conversion tracts are at least 741 bp long, it is possible that the average tract length exceeds this. As am prototrophs were selected for, longer tracts that extend proximal of $am^6$ and cover $am^1$, would not be recovered. Irrespective of this, the conversion tract lengths observed at am are not grossly different from those seen in *S. cerevisiae* (e.g. ~1.5 kb, Borts R H, Haber J E (1987) Meiotic recombination in yeast: alteration by multiple heterozygosities Science 237: 1459–1465; Borts R H, Haber J E (1989) Length and distribution of meiotic gene conversion tracts and crossovers in *Saccharomyces cervisiae* Genetics 123: 69–80) or for selected tracts among *S. pombe* ADE6 prototrophs (~1 kb, Grimm C, Baler J, Kohli J(1994) M26 recombinational hotspot and physical conversion tract analysis in the ade6 gene of *Schizosaccharomyces pombe* Genetics 135: 41–51) where about half of events were reported to be associated with flanker exchange.

The demonstration that discontinuous conversion tracts are found not only in those recombination events initiated at cog but also in recombination events initiated by the hotspot 5' of am shows that any DNA juxtaposed to any recombination hotspot is likely to be diversified.

Methods and formulations for adaptation and use of the his-3 cog system of *Neurospora crassa* for in vivo diversification of heterologous DNA Example 3

Culturing and Crossing Strains of *Neurospora crassa*

Strains of *N. crassa* can be cultured on a mineral medium, for example that of H J Vogel (Am Naturalist 98: 435–446 1964), containing a carbon source (usually 2% sucrose), the vitamin biotin, and supplemented with any nutritional requirements imposed by the specific mutations present in the strains to be grown (D D Perkins et al Microbiol. Rev. 46:426–570 1982). Growth is at a temperature between 20° C. and 36° C., commonly 25° C. or 34° C., depending on the presence of temperature sensitive mutants such as cot-1 which confers colonial morphology at 34° C. but normal growth at 25° C. The medium is usually solidified with agar such as Difco Bacto agar (2%) and dispensed into culture tubes closed with a gas permeable plug such as non-absorbent cotton. Following growth for 2 to 6 days, conidia, the asexual spores, are produced on the aerial hyphae (FIG. 4). These can be collected with an inoculation loop and used to establish further genetically identical cultures. Aconidiate mutants are propagated by the transfer of mycelial fragments to fresh medium. *Neurospora crassa* has two mating types, A and a, determined by the idiomorphs mat A and mat a respectively (NL Glass and C Staben Fung. Genet. Newsl. 44:64, 1997). Crosses are made by co-inoculation of two strains, one of mating type A and the other of mating type a onto a medium formulated to have a low ratio of nitrogen to carbon source, such as that of M Westergaard and HK Mitchell (Am. J. Bot. 34:573–577 1947), SC medium (R H Davis and F J de Serres Methods in Enzymol. 17A: 79–143 1970), or corn-meal medium. The crossing medium is supplemented with any specific nutritional requirements of the strains that result from the presence of specific mutations in one or both of the strains. Cross tubes are incubated at 25° C. as the sexual cycle is not completed at higher temperatures in most laboratory strains of Neurospora as they contain a temperature sensitive tyrosinase. Crosses can also be made by inoculation of a single strain onto low nitrogen medium which is then incubated for 5 to 7 days at 25° C. to permit the development of protoperithecia by one parent (FIG. 4). The protoperithecia are then fertilised by inoculating the culture with the second parent by dusting the mycelium with conidia or flooding with a suspension of conidia in water. The culture is then returned to 25° C. for incubation.

Fertilization, leading to the formation a dikaryon, and the subsequent events: karyogamy of pairs of nuclei of opposite mating type to form diploid cells, meiosis and the formation of octads of ascospores that are shot onto the wall of the culture tube, occur over a period of 14 to 40 days depending on the specific cross being made. A cross made in 4 ml of medium in a 15×150 mm pyrex tube normally yields about $5 \times 10^7$ ascospores, the products of ~$6.10^6$ separate meiosis. Using the present invention, this is sufficient to yield between $10^2$ and $10^5$ variants of heterologous DNA depending upon the degree of difference between the two homologous sequences recombined, the recombinator employed and the selection method used to isolate recombinants.

Growing progeny from a cross are obtained as follows. Individual ascospore are isolated into tubes of appropriately supplemented Vogel's minimal medium containing 2% sucrose or another suitable carbon source, heat shocked at 60° C. for 30 minutes to break ascospore dormancy and kill any conidia present, and germinated at between 25 and 34° C. Alternatively, samples of ascospores are spread onto plates of appropriately supplemented Vogel's medium containing a carbon source designed to limit growth to compact colonies. This can be achieved with 1% sorbose and 0.1% sucrose or 1% sorbose and 0.05% glucose and 0.05% fructose. The spread ascospores are heat shocked and then incubated at 25° C. or, where both parents contain the cot-1 mutation, incubated for 18 hours at 25° C. then at 34° C. until colonies are visible. The use of cot-1 permits plating densities up to about $10/cm^2$, which is about ten-fold higher than practicable when sorbose alone is used limit colony size. Individual progeny can be recovered from such plates by picking pieces of a colony aseptically onto an agar slope of appropriately supplemented Vogel's medium containing 2% sucrose or another suitable carbon source and incubating, at 25° C. if cot-1 is present, or up to 34° C. otherwise.

When one parent of a cross carries an auxotrophic mutation, ie a mutation requiring specific supplements to be added to the growth medium to compensate for their inability to synthesize the substance, half of the progeny of the cross will carry that mutation and will require suitably supplemented growth medium. If both parents carry different auxotrophic mutations, progeny having the mutant genes are recombined are the only ones that will grow in the absence of supplement added to the medium.

The frequency of prototrophic recombinants amongst the progeny of a cross can be estimated by preparing an ascospore suspension from the cross tube, plating aliquots of suitable dilutions of the suspension on both selective and fully supplemented medium and counting the colonies that grow following incubation of the plates at the appropriate temperature.

Example 4

Formulation of Plasmid Vectors

A plasmid can be constructed using methods common in the art for DNA manipulation, some of which are described above. One plasmid according to the invention includes the following DNA sequences in the following order:

1) The first included sequence is a sequence including the majority of the his-3 gene, but lacking a portion of the sequence at the 5' end of the gene, typically a short portion of the sequence of about 30 to about 300 nucleotides, such that the start codon (starting at nucleotide 687 in FIG. 7) is excluded from the plasmid. The first included sequence will terminate beyond the stop codon of the his-3 gene (ending at position 3362 in FIG. 7).

This first included DNA sequence can be derived either from a his-3$^+$ strain of *N. crassa* such as the St Lawrence 74A wild type (FIG. 8), from the Lindegren wild type (FIG. 7) which has a his-3 gene that differs at 14 nucleotide positions from the sequence of St Lawrence 74A, or from one of a pair of complementing his-3 mutants such as K26 derived from Lindegren and K458 derived from the Emerson a wild type that has a his-3 gene identical in sequence to that of St Lawrence 74A.

2) The second included sequence is optional. This sequence includes a promoter for the expression and control of expression of heterologous sequences that is functional in *Neurospora crassa*. This second included sequence is not required in certain circumstances, such as when this type of promoter is introduced as part of the heterologous DNA 3) The third included sequence is optional. This sequence, when the heterologous or foreign sequence codes for a messenger RNA, tags the messenger RNA transcribed from the heterologous DNA for export of the protein product. The third included sequence is present when such export is desired and when such a sequence is not already part of the heterologous DNA insert.

4) The fourth included sequence includes a cloning site having cleavage sites for one or more restriction enzymes. The presence of this sequence provides a site for insertion of heterologous genes and DNA sequences that are not present elsewhere in the plasmid.

5) The fifth included sequence is the cog$^L$ allele of the cog recombinator. This sequence is typically from the 3' flank of the Lindegren wild type from nucleotide 5412 to 6831 (FIG. 7) (preceding the start codon of lpl)

6) The sixth included sequence includes sequences within the lpl gene to provide homology downstream of cog. Such a sequence is typically from the sequence shown in FIG. 7, from position 6831 and 3' for about several hundred base pairs.

7) The seventh included sequence provides a marker gene allowing either positive selection (for example hph$^R$ which confers hygromycin resistance) or negative selection (for example mtr+ which confers p-fluorophenylalanine sensitivity) for the presence of the whole plasmid in Neurospora.

8) The eighth included sequence provides a selectable marker for the presence of the plasmid in *Escherichia coli*, for example amp$^R$.

9) The ninth included sequence provides a replication origin functional in *E. coli* to permit amplification of the plasmid in this species The plasmid vector can also be constructed without one of more of the included sequences. For example, simpler variants of this plasmid design include ones that omit lpl sequences and rely on cog$^L$ sequences for correct register of the recombinational events (as explained hereinbelow) required to establish transplacement of chromosomal sequences with the desired construct which is: heterologous DNA flanked by an active cog allele and either his-3+ or one of a complementing pair of his-3 alleles such as K26 and K458.

Example 5

Cloning of Variants of Sequences to be Diversified

Two or more functional variants of the DNA to be diversified, each differing in sequence at multiple sites, are separately inserted into the multiple cloning site to form a panel of two or more plasmids that are identical except for the DNA incorporated into the multiple cloning site (FIG. 9). The DNA can be inserted using methods known in the art. The foreign DNA variants can be derived from a variety of sources by methods known in the art. For example, the DNA variants can be derived from the genes of different species having homologous genes that produce proteins with equivalent function but differing properties such as pH tolerance, thermostability, substrate range, and the like, or, for example, from differently derived cell lines coding for monoclonal antibodies reacting to the same antigen, or incorporating sequences diversified by in vitro methods.

Example 6

Targeted insertion of heterologous DNA adjacent to cog$^L$
The Strains

The pair of strains used to derive the parents to be crossed together to effect in vivo diversification of heterologous sequences have the following characteristics:

1) The first characteristic is that one is of mating type A and the other mating type a, which allows mating.

2) The second characteristic is that both carry the same allele of each of the other ten known loci that determine heterokaryon compatibility, het-c, -d, -e, -i, and het-5 to het-10. This allows the progeny of crosses to form heterokaryons in any combination of like mating type.

3) The third characteristic is that, when the heterokaryons are to be used to test some or all possible combinations of in vivo diversified DNA, each strain will carry forcing markers for the heterokaryon, such as one or more auxotrophic mutations. This will be applicable where the heterologous DNA codes for a component of a protein having more than one subunit. If the protein is a heteromultimer, it will usually be appropriate to have the same forcing marker present in both parents and the two or more components of the heteromultimer will be diversified in separate crosses to yield the two or more panels of diversified sequences for use in combinatorial trials. If the protein is a homomultimer, there is the option of making two panels of diversified sequences in the same cross by making the parents heterozygous for the forcing markers. Suitable forcing markers include but are not limited to mutations that inactivate one of the following genes: trp-2, pan-2, thi, or arg leading to a requirement respectively for tryptophan, pantothenic acid, thiamine, or arginine.

4) The fourth characteristic is that the pair of strains can carry the mutation tol (D L Newmeyer Can. J. Genet. Cytol. 12:914–926 1970) which suppresses heterokaryon incompatibility between strains of different mating type to allow all combinations of progeny to form heterokaryons.

5) The fifth characteristic is that both strains carry an auxotrophic mutation of the his-3 gene for selection of insertion of heterologous DNA between the his-3 locus and cog$^L$. The allele chosen will be located towards the 3' end of the gene. Where selection for recombination at his-3 will be used to enhance the yield of heterologous sequences diversified by recombination (see hereinbelow), the his-3 alleles will not complement to ensure that any rare aneuploid progeny (progeny having two copies of the chromosome carrying the detectable gene) cannot give rise to a heterokaryon carrying both alleles that will no longer be auxotrophic for the trait of the detectable gene and thereby falsely mimic the desired recombinants. A suitable non complementing allele pair is K26 and K480. Suitable complementing pairs of his-3 alleles are K26 and K458 or K480and K458.

6) The sixth characteristic is that both carry Cog$^L$ and lpl sequences from the Lindegren strain to maximize homology with plasmid sequences and ensure that following insertion of heterologous DNA the strain has an active cog$^L$ recombinator.

7) The seventh characteristic is that both carry rec-2 to permit cog$^L$ to cause recombination in his-3 and the heterologous DNA.

8) The eighth characteristic is that both contain genes conferring resistance to any agent that is to be used to select against the presence of the whole plasmid. For example mtr if p-flurophenylalanine is to be used as the negative selective agent.

9) The ninth characteristic is that both will contain the mutation cot-1 C102t where this is to be used to limit growth on plating media.

10) The tenth characteristic is that both contain such mutations and such additional sequences as can be required for optimum production and optimum secretion of the protein products of the heterologous genes or DNA sequences that are to be diversified.

Targeted Insertion

A plasmid construct carrying a different one of the two variants of the DNA sequence to be diversified is introduced into each member of a pair of parental strains by transfection of spheroplasts or electroporation of conidia by methods known in the art. The detectable genes in each parent strain are alleles that do not complement to ensure that any rare aneuploid progeny (progeny having two copies of the chromosome carrying the detectable gene) do not give rise to a heterokaryon carrying both alleles that will no longer be auxotrophic for the trait of the detectable gene and thereby falsely mimic the desired recombinants. *N. crassa* employed in the present invention preferably carry an auxotrophic mutant of the his-3 gene. Typically, each allele chosen has a mutation toward the 3' end of the his-3 gene. A suitable non complementing allele pair is K26 and K480. Suitable complementing pairs of his-3 alleles are K26 and K458 or K480 and K458.

The plasmid is introduced so that the plasmid sequences replace those present in the chromosome (FIG. 9 and FIG.

10). The chromosome will have, in order: his-3$^+$ (or one of a complementing pair of his-3 alleles such as K26 and K458 or K480 and K458), a variant of the DNA to be diversified, cog$^L$ and the sequences proximal of his-3 and distal of cog$^L$ unchanged.

The transplacement can be achieved in one step by two reciprocal exchange events, one in the sequences between the 3' end of the his-3 sequences in the plasmid and the location of the his-3 mutation in the recipient strain (region 1) and one 3' of the heterologous DNA contained in the plasmid and the 3' terminus of homology in the plasmid (region 2).

Alternatively, the transplacement can be achieved in two steps. First by an exchange in region 1, leading to insertion of the plasmid into the chromosome creating a duplication of those sequences shared by the plasmid and chromosome. This insertion can be selected for by plating the recipient cells on media selective for the positive selection marker (for example where the plasmid carries hph$^R$ by the addition of hygromycin to the growth medium) as well as for the his$^+$ phenotype. Selection for the second event is effected by growing the cells on media without the positive selective agent, hygromycin where the plasmid carries hph$^R$, and screening for the absence of hph$^R$ or by plating cells on media containing the negative selection agent, for example p-fluorophenylalanine if the plasmid carries the Neurospora mtr$^+$ gene which is dominant to mtr in vegetative cells carrying both alleles. Candidate strains are cultured individually in tubes of Vogel's mineral medium supplemented as required.

Correct transplacement of the sequences between the 5' end of his-3 to distal of cog$^L$, including the heterologous sequences to be diversified is checked in each strain by the methods of southern transfer or PCR amplification and analysis of the position of sites sensitive to digestion by restriction enzymes or by PCR amplification and DNA sequencing.

Example 7

In vivo diversification of heterologous genes and DNA sequences

Parent variant 1 and Parent variant 2, being strains of different mating type, one a the other A, each carrying a different variant of the gene or DNA sequence to be diversified are co-inoculated into crossing tubes containing appropriately supplemented SC medium or another medium appropriate for the sexual stage in the life cycle. Where recombination at his-3 is to be used to select for progeny in which the yield of recombinants is enhanced by ensuring that the whole of the heterologous DNA sequence was covered by a conversion tract, the a and the A strains will each carry a different his-3 allele and the SC medium will contain histidine in addition to any other required supplement. The his-3 alleles chosen will usually be a non-complementing pair, for example one will be K26 and the other K480 (FIG. 10), to ensure that rare heterokaryons arising by the breakdown of anuploids containing two copies of chromosome 1 that form when there is failure of chromosome disjunction in meiosis, will not mimic his$^+$ recombinants. If the alleles were a complementing pair such as K26 and K458 or K480 and K458, the resulting heterokaryon would grow on medium lacking histidine, mimicing a his$^+$ recombinant. Such complementing pairs are used to provide selection for transplacement of one his-3 mutant with another in the process of inserting the heterologous DNA adjacent to cog. This preserves the presence of a his-3 mutation when this is required for enhanced frequency of diversification of juxtaposed heterologous DNA.

Crossing tubes are incubated at 25° C. until ascospores are shot onto the wall of the tube and the ascospores matured by incubating for a further 7 days at 25° C. or for 48 hr. at 30° C.

Strains in which the heterologous sequences have been diversified in vivo during meiosis are recovered by transferring individual ascospores to slopes of appropriately supplemented Vogel's N medium containing an appropriate carbon source such as 2% sucrose, heat shocking at 60° C. for 30 minutes to allow germination, and growing at 25° C. for 3 to 5 days. Where it is desired to enrich for diversified sequences by selecting only those progeny where a conversion tract extended from cog$^L$ through the heterologous DNA into the his-3 gene, ascospores are suspended in water, heat shocked at 60° C. for 30 min., spread on the surface of plates containing VM medium with 2% sorbose, 0.05% fructose and 0.05% glucose as carbon source and supplemented as is necessary for all auxotrophic mutants present excepting his-3 (no histidine is added to the medium), and incubated for 18 hr at 25° C. followed by 24 hr at 34° C., or where cot-1 is absent, at 25° C. for 48 hr. Colonies are transferred individually to appropriately supplemented slopes of Vogel's minimal medium containing 2% sucrose or another suitable carbon source and grown at 25° C. to yield a panel of strains enriched for in vivo diversified heterologous DNA sequences.

Example 8

Use of Strains Containing In Vivo Diversified Heterologous DNA and Screening for New Variants Having Desirable Properties Strains containing diversified heterologous sequences are used directly for expression of the variant gene or are combined in pairwise or higher order combinations in heterokaryons where a heteromeric protein such as an immunoglobulin is the product. Conditions and tests as needed for each specific case are used to screen for variants with the desired new combination of properties. Where (tol is present in both parents of the cross used to diversify the heterologous sequences, all combinations of progeny can be combined in pairwise or in higher order combinations in heterokaryons. Where tol is absent from the parents, it is necessary to divide the progeny into two groups, those of mating type a and those of mating type A, and combine only those strains of like mating type in pairwise or higher order combinations.

The test for mating type can be effected by determining the mating reaction with tester strains one of A and one of a mating type R H Davis and F J deSerres (Methods in Enzymol. 17A: 79–143 1970). In this method, strains of known mating type are inoculated onto SC medium and grown at 25° C. until protoperithecia are formed then inoculated with conidia of strains of unknown mating type. Mating type can be scored within 24–48 hours by the development of perithecia in tubes inoculated with conidia of the opposite mating type.

Example 9

Provision of markers for the isolation of recombinant forms of heterologous DNA

Targeting plasmid DNA into a specific chromosomal location is achieved by transfection of an auxotrophic mutant with a plasmid carrying non mutant sequence leading to the restoration of a normal gene in the recipient chromosome (FIG. 9). Transformants with the plasmid DNA correctly targeted are selected by their ability to grow on media not supplemented with the requirements of the auxotrophic mutation. Where the fraction of progeny from a cross that experienced conversion of heterologous DNA is too low to provide a good yield of diversified sequences, it is necessary to be able to enrich for those that did experience conversion to provide the panel of diversified sequences. This can be achieved if a his-3 mutation remains in the chromosome of the recipient cell after insertion of the heterologous DNA.

Complementing allelic mutations of the his-3 gene (DG Catcheside and T Angel Aust. J. Biol. Sci. 27:219–29 1974) provide a means of achieving transplacement at his-3 leaving a his-3 mutation conferring a requirement in the chromosome carrying the heterologous DNA. This is made possible because his-3 codes for a peptide that forms a homomultimeric protein. Although the homomultimer formed of subunits coded by his-3 K26 and the homomultimer formed by subunits coded by his-3 K458 are both inactive, a heteromultimer containing subunits coded by his-3 K26 and other subunits coded by his-3 K458 is enzymatically active. As a result, a heterokaryon containing nuclei having the his-3 K26 mutation and also nuclei having the his-3 K458 mutation is able to grow on media that do not contain histidine. Since K26 is located 3' of K458 and since Neurospora cells are usually multinucleate, transfection of strain carrying the his-3 K458 mutation (and having a mating type and such other genetic markers as can be required for screening of the DNA following diversification) with a targeting plasmid carrying heterologous DNA and the his-3 K26 sequence, instead of the his-3 wild type sequence, will establish a heterokaryon with two sorts of nuclei. One nuclear type will carry the his-3 K458 mutation and the other type will carry the heterologous DNA juxtaposed to the his-3 K26 mutation. The heterokaryon can be specifically selected by its ability to grow on media that contain no added histidine.

A homokaryon containing only the nuclear type carrying the his-3 K26 mutation and the juxtaposed heterologous DNA is isolated by picking colonies to slopes of minimal medium, growing to conidia and isolating homokaryons by establishing new cultures on medium containing histidine from single conidia. Random assortment of the two nuclear types into the conidia frequently gives rise to homokaryons. This can be made more efficient by forcing the production of microconidia having only a single nucleus by growing the heterokaryon on media supplemented with iodoacetate (D Ebbole and MS Sachs Fun. Genet. Newsl. 37:17–18 1990).

The homokaryon can then be used as one parent [parent (variant 1)] of the cross used to diversify the heterologous DNA (FIG. 10). A second homokaryon containing the his-3 K480 mutation and foreign variant 2 of the heterologous DNA can be isolated in a similar way (FIG. 10) by transfecting a his-3 K458 strain, of opposite mating type to that used to construct parent (variant 1) (and with such other genetic markers as can be needed for subsequent screening of the DNA following diversification). The plasmid used for transfection will carry a homolog of the DNA to be diversified, different to that used for construction of parent (variant 1), juxtaposed to the DNA sequences from the his-3 gene from a his-3 K480 strain. Since his-3 K480 is located 3' of his-3 K458 and they are a complementing pair, a heterokaryon with two sorts of nuclei can be selected on minimal medium. One nuclear type will carry the his-3 K458 mutation and the other type will carry the variant 2 DNA juxtaposed to the his-3 K480 mutation. Parent (variant 2) for the DNA diversification cross which carries variant 2 DNA juxtaposed to his-3 K480 can be recovered from the heterokaryon in the same manner as that used to establish parent (variant 1).

The his-3 alleles used for the construction of parent (variant 1) and parent (variant 2) are dictated by (1) the plasmid sequence should carry the most 3' his-3 allele (2) the pair used for the establishment of the heterokaryon must be a complementing pair and (3) the pair used for parent (variant 1) and parent (variant 2) should be non complementing. K26 and K480 do not complement. Dictate (1) to ensure his-3+ chromosomes are not established, dictate (2) to provide for the selection of chromosomes carrying a his-3 mutant juxtaposed to the heterologous DNA to be diversified and dictate (3) to eliminate the selection of his-3+ recombinants from the diversification cross which are aneuploid. (aberrant cells carrying two copies of the section of chromosome bearing the his-3 gene).

The invention has been described with reference to various specific and preferred embodiments and techniques. However, it should be understood that many variations and modifications can be made while remaining within the spirit and scope of the invention.

All publications and patent applications in this specification are indicative of the level of ordinary skill in the art to which this invention pertains. All publications and patent applications are herein incorporated by reference to the same extent as if each individual publication or patent application was specifically and individually indicated by reference.

What is claimed is:

1. A haploid fungal cell comprising:
a recombinant genome, the recombinant genome comprising a heterologous DNA functionally coupled to a recombination hotspot;
the recombination hot spot being *Neurospora crassa* cog, 3' of his-3 and 3' of am in *Neurospora crassa*, 3' of his4 and 3' of arg4 in *S. cerevisiae*, or within ade6 in *S. pombe*;
the haploid fungal cell being capable of being converted to a diploid fungal cell;
the heterologous DNA being adapted and configured within the recombinant genome for recombination in the diploid fungal cell.

2. The haploid fungal cell of claim 1, wherein the fungal cell is *Neurospora crassa*, *S. cerevisiae*, or *S. pombe*.

3. The haploid fungal cell of claim 1, wherein the haploid cell is a cell of a filamentous fungus, of a conidium or other asexual spore, an ascospore, zygospore, basidiospore or other sexual spore, mycelium, heterokaryon, dikaryon or homokaryon, or is a yeast cell.

4. The haploid fungal cell of claim 1, wherein the recombination hot spot is an allele of *Neurospora crassa* cog.

5. The haploid fungal cell of claim 4, wherein the recombination hot spot is *Neurospora crassa* $cog^L$.

6. The haploid fungal cell of claim 4, wherein the heterologous DNA is located between the his-3 gene and cog.

7. The haploid fungal cell of claim 1, wherein the heterologous DNA is a promoter, is a regulatory sequence, is a noncoding sequence, encodes all or part of a subunit of an immunoglobulin, all or part of a heteromultimeric protein, all or part of a homomultimeric protein, all or part of a monomeric protein, all or part of a non-transcribed DNA sequence, all or part of a sequence that regulates the activity of a gene, all or part of a sequence transcribed into an RNA molecule lacking catalytic activity, all or part of a sequence transcribed into an RNA molecule having catalytic activity, or a combination thereof.

8. The haploid fungal cell of claim 1, wherein the fungal cell is *Neurospora crassa* of mating type A or type a.

9. A pair of haploid fungal cells according to claim 1, wherein each cell carries the same allele of the genetic loci that determine heterokaryon compatibility, whereby the progeny of crosses of the pair of cells can form heterokaryons in any combination of like mating type.

10. The pair of cells of claim 9, wherein each fungal cell is *Neurospora crassa* and each cell carries the same allele of the genetic loci het-c, het-d, het-e, het-i, het-5, het-6, het-7, het-8, het-9, and het-10.

11. The haploid fungal cell of claim 1, wherein the fungal cell comprises a forcing marker for a heterokaryon formed from the haploid cell.

12. The haploid fungal cell of claim 11, wherein the forcing marker comprises one or more auxotrophic mutations.

13. The haploid fungal cell of claim 12, wherein the forcing marker leads to a requirement for tryptophan, pantothenic acid, thiamine, or arginine.

14. The haploid fungal cell of claim 13, wherein the fungal cell is *Neurospora crassa* and the forcing marker is a mutation that inactivates a trp-2 gene, a pan-2 gene, a thi gene, or an arg gene.

15. The haploid fungal cell of claim 11, wherein the heterologous DNA codes for a subunit of a multisubunit protein.

16. A pair of haploid fungal cells according to claim 15, wherein each cell comprises a forcing marker for a heterokaryon formed from the haploid cell, and each forcing marker is the same.

17. The pair of haploid cells of claim 16, wherein the heterologous DNA encodes subunits of a protein having a more than one type of subunit.

18. A pair of haploid fungal cells according to claim 17, wherein each cell comprises a forcing marker for a heterokaryon formed from the haploid cell, and the forcing markers are different.

19. The pair of haploid cells of claim 18, wherein the heterologous DNA encodes subunits of a protein having a single type of subunit.

20. The haploid fungal cell of claim 1, wherein the fungal cell comprises a genetic characteristic that suppresses heterokaryon incompatibility between strains of different mating type to allow all combinations of progeny to form heterokaryons.

21. The haploid fungal cell of claim 20, wherein the fungal cell is Neurospora crassa and the cell carries the mutation tol, whereby heterokaryon incompatibility between strains of different mating type is suppressed.

22. The haploid fungal cell of claim 1, wherein the fungal cell is Neurospora crassa and the recombinant genome comprises an auxotrophic mutation in the his-3.

23. A pair of haploid fungal cells according to claim 1, wherein each fungal cell is Neurospora crassa and the pair cells comprise a non-complementing pair of his-3 alleles.

24. The pair of haploid cells of claim 23, wherein the non-complementing pair is K26 and K480 whereby a heterokaryon carrying both alleles fails to grow on media lacking histidine.

25. The pair of haploid fungal cells of claim 23, wherein the fungal cell is Neurospora crassa and the cell carries $cog^L$ and lpl sequences from the Lindegren strain.

26. The pair of haploid fungal cells of claim 23, wherein the fungal cell is Neurospora crassa and the cell carries rec-2.

27. The haploid fungal cell of claim 1, wherein the fungal cell is Neurospora crassa comprising a gene conferring resistance to an agent for selecting against the presence of the recombinant genome.

28. The haploid fungal cell of claim 27 wherein the agent is p-flurophenylalanine.

29. The haploid cell of claim 27, wherein the gene conferring resistance is mtr.

30. The haploid fungal cell of claim 1, wherein the fungal cell is Neurospora crassa comprising a mutant gene to limit growth on plating media.

31. The haploid fungal cell of claim 30, wherein the mutant gene is cot-1 C102t.

32. The haploid fungal cell of claim 1, wherein the recombinant genome comprises DNA sequences to enhance production, secretion, or both of a protein encoded by the heterologous sequence.

33. A diploid fungal cell comprising:
a recombinant genome, the recombinant genome comprising a first heterologous DNA functionally coupled to a first recombination hotspot and a second heterologous DNA functionally coupled to a second recombination hotspot;

the first and second recombination hotspots independently being Neurospora crassa cog, 3' of his-3 and 3' of am in Neurospora crassa, 3' of his4 and 3' of arg4 in S. cerevisiae, or within ade6 in S. pombe;

the first heterologous DNA and second heterologous DNA being adapted and configured within the recombinant genome for recombination.

34. The diploid fungal cell of claim 33, wherein the fungal cell is Neurospora crassa, S. cerevisiae, or S. pombe.

35. The diploid fungal cell of claim 33, wherein the diploid cell is a cell of a filamentous fungus, or a yeast cell, following karyogamy.

36. The diploid fungal cell of claim 33, wherein the first and second recombination hot spots are alleles of the Neurospora crassa cog recombination hotspot.

37. The diploid fungal cell of claim 36, wherein either or both of the first and second recombination hot spots are Neurospora crassa $cog^L$.

38. The diploid fungal cell of claim 36, wherein the heterologous DNA is located between the his-3 gene and cog.

39. The diploid fungal cell of claim 38, wherein either the first or the second heterologous DNA is located between an inactive mutant of a his-3 gene and cog.

40. The diploid fungal cell of claim 33, wherein the heterologous DNA is a promoter, is a regulatory sequence, is a noncoding sequence, encodes all or part of a subunit of an immunoglobulin, all or part of a heteromultimeric protein, all or part of a homomultimeric protein, all or part of a monomeric protein, all or part of a non-transcribed DNA sequence, all or part of a sequence that regulates the activity of a gene, all or part of a sequence transcribed into an RNA molecule lacking catalytic activity, all or part of a sequence transcribed into an RNA molecule having catalytic activity, or a combination thereof.

41. A haploid cell derived from the diploid fungal cell of claim 33, the haploid cell arising by meiosis and recombination, wherein the recombinant genome comprises a new sequence combination resulting from a crossover, a discontinuous conversion tract, or an error in recombination.

42. The diploid fungal cell of claim 33, wherein the fungal cell is Neurospora crassa of mating type A or type a.

43. The diploid fungal cell of claim 33, wherein the cell carries pairs of alleles of genetic loci that determines heterokaryon compatibility, whereby progeny of crosses of the cell can form heterokaryons in any combination of like mating type.

44. The diploid cell of claim 43, wherein the fungal cell is Neurospora crassa and each cell carries the same allele of the genetic loci het-c, het-d, het-e, het-i, het-5, het-6, het-7, het-8, het-9, and het-10.

45. The diploid fungal cell of claim 33, wherein the fungal cell comprises a forcing marker for a heterokaryon formed from the diploid cell.

46. The diploid fungal cell of claim 45, wherein the forcing marker comprises one or more auxotrophic mutations.

47. The diploid fungal cell of claim 46, wherein the forcing marker instills to a requirement for tryptophan, pantothenic acid, thiamine, or arginine.

48. The diploid fungal cell of claim 46, wherein the fungal cell is Neurospora crassa and the forcing marker is a mutation that inactivates a trp-2 gene, a pan-2 gene, a thi gene, or an arg gene.

49. The diploid fungal cell of claim 45, wherein the heterologous DNA codes for a subunit of a multisubunit protein.

50. The diploid fungal cell of claim 45, wherein the cell comprises two of a forcing marker for a heterokaryon formed from the cell.

51. The diploid fungal cell of claim 50, wherein the heterologous DNA encodes subunits of a protein having a more than one type of subunit.

52. The diploid fungal cell of claim 45, wherein the cell comprises two distinct forcing markers for a heterokaryon formed from the cell.

53. The diploid fungal cell of claim 52, wherein the heterologous DNA encodes subunits of a protein having a single type of subunit.

54. The diploid fungal cell of claim 33, wherein the fungal cell comprises a genetic characteristic that suppresses heterokaryon incompatibility between strains of different mating type, whereby all combinations of progeny can form heterokaryons.

55. The diploid fungal cell of claim 54, wherein the fungal cell is *Neurospora crassa* and the cell carries the mutation tol, whereby heterokaryon incompatibility between strains of different mating type is suppressed.

56. The diploid fungal cell of claim 33, wherein the fungal cell is *Neurospora crassa* and the recombinant genome comprises an auxotrophic mutation in the his-3 gene.

57. The diploid fungal cell of claim 56, wherein the auxotrophic mutation is located towards the 3' end of the gene.

58. The diploid fungal cell of claim 56, wherein the fungal cell is *Neurospora crassa* and comprises a non-complementing pair of his-3 alleles.

59. The pair of diploid cells of claim 58, wherein the non-complementing pair is K26 and K480, whereby a heterokaryon carrying both alleles is unable to grow on media lacking histidine.

60. The diploid fungal cell of claim 56, wherein the fungal cell is *Neurospora crassa* and the cell carries $cog^L$ and lpl sequences from the Lindegren strain.

61. The diploid fungal cell of claim 56, wherein the fungal cell is *Neurospora crassa* and the cell carries rec-2 in both chromosome sets.

62. The diploid fungal cell of claim 33, wherein the fungal cell is *Neurospora crassa* and comprises a gene conferring resistance to an agent for selecting against the presence of the whole plasmid.

63. The diploid fungal cell of claim 62, wherein the agent is p-flurophenylalanine.

64. The diploid fungal cell of claim 62, wherein the gene conferring resistance is mtr.

65. The diploid fungal cell of claim 33, wherein the fungal cell is *Neurospora crassa* and comprises a mutant gene to limit growth on plating media.

66. The diploid fungal cell of claim 65, wherein the mutant gene is cot-1 C102t.

67. The diploid fungal cell of claim 33, wherein the recombinant genome comprises DNA sequences to enhance production, secretion, or both of a protein encoded by the heterologous sequence.

68. A haploid fungal cell comprising a recombinant genome, the recombinant genome comprising a heterologous DNA functionally coupled to a fungal recombination hotspot; the haploid fungal cell being capable of being converted to a diploid fungal cell; the heterologous DNA being adapted and configured within the recombinant genome for recombination in the diploid fungal cell.

69. A diploid fungal cell comprising a recombinant genome, the recombinant genome comprising a first heterologous DNA functionally coupled to a first fungal recombination hotspot and a second heterologous DNA functionally coupled to a second fungal recombination hotspot; the first heterologous DNA and second heterologous DNA being adapted and configured within the recombinant genome for recombination.

* * * * *